US012788463B2

(12) United States Patent
O'Brien et al.

(10) Patent No.: US 12,788,463 B2
(45) Date of Patent: Nov. 10, 2026

(54) CONTROLLED LESION AND IMMUNE RESPONSE TO PULSED ELECTRIC FIELD THERAPY

(71) Applicant: Galvanize Therapeutics, Inc., Redwood City, CA (US)

(72) Inventors: Timothy J. O'Brien, Santa Clara, CA (US); William S. Krimsky, Forest Hill, MD (US); Matthew T. Silvestrini, San Francisco, CA (US); Chiara Pastori, Hayward, CA (US); Robert E. Neal, II, Redwood City, CA (US); Jonathan R. Waldstreicher, West Orange, NJ (US); Ebtesam Nafie, Belmont, CA (US); Mukta S Wagh, Sunnyvale, CA (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 205 days.

(21) Appl. No.: 18/416,809

(22) Filed: Jan. 18, 2024

(65) Prior Publication Data

US 2024/0350185 A1 Oct. 24, 2024

Related U.S. Application Data

(63) Continuation-in-part of application No. PCT/US2022/044021, filed on Sep. 19, 2022.

(Continued)

(51) Int. Cl.

| | |
|---|---|
| ***A61B 18/12*** | (2006.01) |
| ***A61B 18/00*** | (2006.01) |

(52) U.S. Cl.

CPC .... *A61B 18/00* (2013.01); *A61B 2018/00577* (2013.01); *A61B 2018/00732* (2013.01);

(Continued)

(58) Field of Classification Search

CPC ................ A61B 18/00; A61B 18/1492; A61B 2018/00577; A61B 2018/00589;

(Continued)

(56) References Cited

U.S. PATENT DOCUMENTS

| | | | |
|---|---|---|---|
| 874,178 | A | 12/1907 | Forest |
| 4,249,541 | A | 2/1981 | Pratt |

(Continued)

FOREIGN PATENT DOCUMENTS

| | | | |
|---|---|---|---|
| AT | 306859 | B | 4/1973 |
| AU | 200048007 | | 11/2000 |

(Continued)

OTHER PUBLICATIONS

A. Valipour et al. Bronchial Rheoplasty Treatment for Chronic Bronchitis Using the Rheox System, 2020 American Thoracic Society, Abstract, Aug. 5, 2020.

(Continued)

*Primary Examiner* — Daniel W Fowler

(74) *Attorney, Agent, or Firm* — Greenberg Traurig, LLP; Christopher C. Bolten; Emma Hawley

(57) ABSTRACT

Treatment of damaged, diseased, abnormal, obstructive, cancerous or undesired tissue (e.g. a tumor, a benign tumor, a malignant tumor, a cyst, or an area of diseased tissue, etc.) is provided by delivering specialized pulsed electric field (PEF) energy to target tissue areas in a specific dose so as to obtain a superior outcome. The PEF energy and delivery has been optimized to provide advanced treatment of target tissue areas, including destruction of undesired tissue and generation of improved inflammatory and immune responses. These various types of treatment are controlled by a variety of factors including the electrode geometry, the dose of PEF energy delivered, the time the energy is delivered over, and the waveform of the PEF energy itself.

(Continued)

The PEF energy is delivered in the form a dose which is considered to be one application of the specialized energy. Each dose creates a lesion in the target tissue area.

25 Claims, 39 Drawing Sheets

Related U.S. Application Data

(60) Provisional application No. 63/480,468, filed on Jan. 18, 2023, provisional application No. 63/488,304, filed on Mar. 3, 2023, provisional application No. 63/246,239, filed on Sep. 20, 2021, provisional application No. 63/290,529, filed on Dec. 16, 2021, provisional application No. 63/322,319, filed on Mar. 22, 2022, provisional application No. 63/351,562, filed on Jun. 13, 2022.

(52) U.S. Cl.
CPC ............... *A61B 2018/00761* (2013.01); *A61B 2018/00767* (2013.01)

(58) Field of Classification Search
CPC ........... A61B 2018/00732; A61B 2018/00761; A61B 2018/00767; A61B 2018/1425; A61B 2018/143; A61B 2018/1475
See application file for complete search history.

(56) References Cited

U.S. PATENT DOCUMENTS

| | | | |
|---|---|---|---|
| 4,822,470 | A | 4/1989 | Chang |
| 5,232,856 | A | 8/1993 | Firth |
| 5,304,120 | A | 4/1994 | Crandell et al. |
| 5,383,874 | A | 1/1995 | Jackson et al. |
| 5,386,837 | A | 2/1995 | Sterzer |
| 5,507,724 | A | 4/1996 | Hofmann et al. |
| 5,601,588 | A | 2/1997 | Tonomura et al. |
| 5,683,384 | A | 11/1997 | Gough et al. |
| 5,704,908 | A | 1/1998 | Hofmann et al. |
| 5,833,710 | A | 11/1998 | Jacobson |
| 5,906,609 | A | 5/1999 | Assa et al. |
| 5,972,026 | A | 10/1999 | Laufer et al. |
| 6,009,347 | A | 12/1999 | Hofmann |
| 6,038,478 | A | 3/2000 | Yuen et al. |
| 6,041,252 | A | 3/2000 | Walker et al. |
| 6,078,490 | A | 6/2000 | Walters |
| 6,083,255 | A | 7/2000 | Laufer et al. |
| 6,107,699 | A | 8/2000 | Swanson |
| 6,120,493 | A | 9/2000 | Hofmann |
| 6,200,333 | B1 | 3/2001 | Laufer |
| 6,219,577 | B1 | 4/2001 | Brown, III et al. |
| 6,233,482 | B1 | 5/2001 | Hofmann et al. |
| 6,248,056 | B1 | 6/2001 | Persson |
| 6,261,831 | B1 | 7/2001 | Agee |
| 6,273,907 | B1 | 8/2001 | Laufer |
| 6,283,988 | B1 | 9/2001 | Laufer et al. |
| 6,283,989 | B1 | 9/2001 | Laufer et al. |
| 6,299,633 | B1 | 10/2001 | Laufer |
| 6,326,177 | B1 | 12/2001 | Schoenbach et al. |
| 6,366,808 | B1 | 4/2002 | Schroeppel et al. |
| 6,391,024 | B1 | 5/2002 | Sun et al. |
| 6,411,852 | B1 | 6/2002 | Danek et al. |
| 6,488,673 | B1 | 12/2002 | Laufer et al. |
| 6,520,950 | B1 | 2/2003 | Hofmann et al. |
| 6,569,149 | B2 | 5/2003 | Dev et al. |
| 6,634,363 | B1 | 10/2003 | Danek et al. |
| 6,678,558 | B1 | 1/2004 | Dimmer et al. |
| 6,697,670 | B2 | 2/2004 | Chomenky et al. |
| 6,733,485 | B1 | 5/2004 | Whitehurst et al. |
| 6,738,663 | B2 | 5/2004 | Schroeppel et al. |
| 6,770,070 | B1 | 8/2004 | Balbierz |
| 6,795,728 | B2 | 9/2004 | Chornenky et al. |
| 6,892,099 | B2 | 5/2005 | Jaafar et al. |
| 6,994,706 | B2 | 2/2006 | Chornenky et al. |
| 7,027,869 | B2 | 4/2006 | Danek et al. |
| 7,054,685 | B2 | 5/2006 | Dimmer et al. |
| 7,104,987 | B2 | 9/2006 | Biggs et al. |
| 7,130,697 | B2 | 10/2006 | Chornenky et al. |
| 7,171,263 | B2 | 1/2007 | Darvish |
| 7,198,635 | B2 | 4/2007 | Danek et al. |
| 7,200,445 | B1 | 4/2007 | Dalbec et al. |
| 7,211,083 | B2 | 5/2007 | Chornenky et al. |
| 7,255,693 | B1 | 8/2007 | Johnston et al. |
| 7,264,002 | B2 | 9/2007 | Danek et al. |
| 7,273,055 | B2 | 9/2007 | Danek et al. |
| 7,344,533 | B2 | 3/2008 | Pearson et al. |
| 7,395,112 | B2 | 7/2008 | Keisari et al. |
| 7,412,284 | B2 | 8/2008 | Hofmann |
| 7,412,285 | B2 | 8/2008 | Schroeppel et al. |
| 7,425,212 | B1 | 9/2008 | Danek et al. |
| 7,445,618 | B2 | 11/2008 | Eggers et al. |
| 7,542,802 | B2 | 6/2009 | Danek et al. |
| 7,556,624 | B2 | 7/2009 | Laufer et al. |
| 7,565,205 | B2 | 7/2009 | Palti |
| 7,565,206 | B2 | 7/2009 | Palti |
| 7,594,925 | B2 | 9/2009 | Danek et al. |
| 7,599,745 | B2 | 10/2009 | Palti |
| 7,599,746 | B2 | 10/2009 | Palti |
| 7,620,451 | B2 | 11/2009 | Demarais et al. |
| 7,655,004 | B2 | 2/2010 | Long |
| 7,680,543 | B2 | 3/2010 | Azure |
| 7,708,768 | B2 | 5/2010 | Danek et al. |
| 7,713,740 | B2 | 5/2010 | Jaroszeski et al. |
| 7,722,606 | B2 | 5/2010 | Azure |
| 7,740,017 | B2 | 6/2010 | Danek et al. |
| 7,742,811 | B2 | 6/2010 | Schroeppel et al. |
| 7,756,583 | B2 | 7/2010 | Demarais et al. |
| 7,765,010 | B2 | 7/2010 | Chornenky et al. |
| 7,770,584 | B2 | 8/2010 | Danek et al. |
| 7,805,201 | B2 | 9/2010 | Palti |
| 7,819,908 | B2 | 10/2010 | Ingenito |
| 7,824,870 | B2 | 11/2010 | Kovalcheck et al. |
| 7,837,679 | B2 | 11/2010 | Biggs et al. |
| RE42,016 | E | 12/2010 | Chornenky et al. |
| 7,853,331 | B2 | 12/2010 | Kaplan et al. |
| 7,853,333 | B2 | 12/2010 | Demarais |
| 7,854,734 | B2 | 12/2010 | Biggs et al. |
| 7,879,610 | B1 | 2/2011 | Heller et al. |
| 7,906,124 | B2 | 3/2011 | Laufer et al. |
| 7,917,227 | B2 | 3/2011 | Palti |
| RE42,277 | E | 4/2011 | Jaafar et al. |
| 7,921,855 | B2 | 4/2011 | Danek et al. |
| 7,931,647 | B2 | 4/2011 | Wizeman et al. |
| 7,937,143 | B2 | 5/2011 | Demarais et al. |
| 7,938,123 | B2 | 5/2011 | Danek et al. |
| 7,938,824 | B2 | 5/2011 | Chornenky et al. |
| 7,949,407 | B2 | 5/2011 | Kaplan et al. |
| 7,959,628 | B2 | 6/2011 | Schaer et al. |
| 7,992,572 | B2 | 8/2011 | Danek et al. |
| 8,007,496 | B2 | 8/2011 | Rioux et al. |
| 8,014,854 | B2 | 9/2011 | Schroeppel et al. |
| 8,019,414 | B2 | 9/2011 | Palti |
| 8,024,048 | B2 | 9/2011 | Schroeppel et al. |
| 8,026,223 | B1 | 9/2011 | Heller et al. |
| RE42,835 | E | 10/2011 | Chornenky et al. |
| 8,048,067 | B2 | 11/2011 | Davalos et al. |
| RE43,009 | E | 12/2011 | Chornenky et al. |
| 8,105,324 | B2 | 1/2012 | Palanker et al. |
| 8,109,926 | B2 | 2/2012 | Azure |
| 8,114,070 | B2 | 2/2012 | Rubinsky et al. |
| 8,120,207 | B2 | 2/2012 | Sanders et al. |
| 8,131,371 | B2 | 3/2012 | Demarals et al. |
| 8,145,316 | B2 | 3/2012 | Deem et al. |
| 8,145,317 | B2 | 3/2012 | Demarais et al. |
| 8,150,519 | B2 | 4/2012 | Demarais et al. |
| 8,150,520 | B2 | 4/2012 | Demarais et al. |
| 8,161,978 | B2 | 4/2012 | Danek et al. |
| 8,181,656 | B2 | 5/2012 | Danek et al. |
| 8,221,411 | B2 | 7/2012 | Francischelli et al. |
| 8,231,603 | B2 | 7/2012 | Hobbs et al. |

(56) References Cited

U.S. PATENT DOCUMENTS 8,235,983 B2 8/2012 Webster et al.
8,244,345 B2 8/2012 Palti
8,251,070 B2 8/2012 Danek et al.
8,251,986 B2 8/2012 Chornenky et al.
8,257,413 B2 9/2012 Danek et al.
8,267,094 B2 9/2012 Danek et al.
8,282,631 B2 10/2012 Davalos et al.
8,292,882 B2 10/2012 Danek et al.
8,298,222 B2 10/2012 Rubinsky et al.
8,298,224 B2 10/2012 Danek et al.
8,406,870 B2 3/2013 Palti
8,425,505 B2 4/2013 Long
8,428,710 B2 4/2013 Kuriyama et al.
8,443,810 B2 5/2013 Danek et al.
8,449,538 B2 5/2013 Long
8,459,268 B2 6/2013 Danek et al.
8,464,723 B2 6/2013 Danek et al.
8,465,484 B2 6/2013 Davalos et al.
8,465,486 B2 6/2013 Danek et al.
8,480,667 B2 7/2013 Kaplan et al.
8,500,713 B2 8/2013 Ferek-Petric
8,504,147 B2 8/2013 Deem et al.
8,512,334 B2 8/2013 Nuccitelli et al.
8,521,274 B2 8/2013 Gutsol et al.
8,534,291 B2 9/2013 Danek et al.
8,540,710 B2 9/2013 Johnson et al.
8,562,588 B2 10/2013 Hobbs et al.
8,568,403 B2 10/2013 Soltesz et al.
8,579,888 B2 11/2013 Hoey et al.
8,584,681 B2 11/2013 Danek et al.
8,600,494 B2 12/2013 Schroeppel et al.
8,603,087 B2 12/2013 Rubinsky et al.
8,620,423 B2 12/2013 Demarais et al.
8,632,534 B2 1/2014 Pearson et al.
8,634,929 B2 1/2014 Chornenky et al.
8,636,726 B1 1/2014 Wells et al.
8,640,711 B2 2/2014 Danek et al.
8,647,338 B2 2/2014 Chornenky et al.
8,652,130 B2 2/2014 Kreindel
8,676,309 B2 3/2014 Deem et al.
8,721,632 B2 5/2014 Hoey et al.
8,733,367 B2 5/2014 Danek et al.
8,740,895 B2 6/2014 Mayse et al.
8,753,335 B2 6/2014 Moshe et al.
8,774,922 B2 7/2014 Zarins et al.
8,777,943 B2 7/2014 Mayse et al.
8,802,643 B1 8/2014 Heller et al.
8,814,860 B2 8/2014 Davalos et al.
8,828,945 B2 9/2014 Laufer et al.
8,888,769 B2 11/2014 Biggs et al.
8,903,488 B2 12/2014 Callas et al.
8,906,006 B2 12/2014 Chornenky et al.
8,911,430 B2 12/2014 Hoey et al.
8,911,439 B2 12/2014 Mayse et al.
8,920,413 B2 12/2014 Danek et al.
8,926,606 B2 1/2015 Davalos et al.
8,927,518 B1 1/2015 Heller et al.
8,944,071 B2 2/2015 Loomas et al.
8,968,210 B2 3/2015 Mugan et al.
8,974,417 B2 3/2015 Kimura et al.
8,992,513 B2 3/2015 Delaney
8,992,517 B2 3/2015 Davalos et al.
9,005,189 B2 4/2015 Davalos et al.
9,017,324 B2 4/2015 Mayse et al.
9,027,564 B2 5/2015 Danek et al.
9,033,976 B2 5/2015 Danek et al.
9,037,230 B2 5/2015 Goldfarb et al.
9,078,665 B2 7/2015 Moss et al.
9,095,323 B2 8/2015 Chu et al.
9,101,764 B2 8/2015 Nuccitelli et al.
9,108,052 B2 8/2015 Jarrard
9,125,666 B2 9/2015 Steinke et al.
9,144,449 B2 9/2015 Burr et al.
9,168,373 B2 10/2015 Nuccitelli et al.
9,173,704 B2 11/2015 Hobbs et al.
9,186,128 B2 11/2015 Mugan et al.
9,198,733 B2 12/2015 Neal et al.
9,199,091 B2 12/2015 Danek et al.
9,211,155 B2 12/2015 Fruland et al.
9,242,041 B2 1/2016 Kosik et al.
9,259,235 B2 2/2016 Chierchia et al.
9,265,563 B2 2/2016 Racz et al.
9,272,132 B2 3/2016 Laufer et al.
9,277,957 B2 3/2016 Long et al.
9,283,374 B2 3/2016 Hollett et al.
9,289,606 B2 3/2016 Paul et al.
9,295,516 B2 3/2016 Pearson et al.
9,301,796 B2 4/2016 Burr et al.
9,308,043 B2 4/2016 Zarins et al.
9,308,044 B2 4/2016 Zarins et al.
9,314,620 B2 4/2016 Long et al.
9,327,122 B2 5/2016 Zarins et al.
9,332,973 B2 5/2016 McWeeney et al.
9,339,328 B2 5/2016 Ortiz et al.
9,339,618 B2 5/2016 Deem et al.
9,358,024 B2 6/2016 Danek et al.
9,375,268 B2 6/2016 Long
9,414,881 B2 8/2016 Callas et al.
9,439,726 B2 9/2016 Zarins et al.
9,486,266 B2 11/2016 Soltesz et al.
9,510,888 B2 12/2016 Lalonde
9,526,568 B2 12/2016 Ohri et al.
9,572,619 B2 2/2017 Laufer et al.
9,598,691 B2 3/2017 Davalos
9,610,067 B2 4/2017 Sekikawa
9,610,364 B1 4/2017 Heller et al.
9,629,912 B2 4/2017 Soikum et al.
9,649,153 B2 5/2017 Mayse et al.
9,649,154 B2 5/2017 Mayse et al.
9,655,669 B2 5/2017 Palti et al.
9,656,055 B2 5/2017 Weissberg et al.
9,656,066 B2 5/2017 Nuccitelli et al.
9,668,809 B2 6/2017 Mayse et al.
9,675,406 B2 6/2017 Moss et al.
9,675,412 B2 6/2017 Mayse et al.
9,681,909 B2 6/2017 Bhargav et al.
9,700,368 B2 7/2017 Callas et al.
9,717,552 B2 8/2017 Cosman
9,724,155 B2 8/2017 Nuccitelli et al.
9,788,707 B2 10/2017 Tinkham et al.
9,789,331 B2 10/2017 Danek et al.
9,820,724 B2 11/2017 Mamiya
9,820,797 B2 11/2017 Burr et al.
9,833,617 B2 12/2017 Travers et al.
9,867,648 B2 1/2018 Mulcahey et al.
9,867,652 B2 1/2018 Sano et al.
9,877,708 B2 1/2018 McWeeney et al.
9,888,956 B2 2/2018 Model et al.
9,895,189 B2 2/2018 Pearson
9,931,161 B2 4/2018 Willis
9,931,163 B2 4/2018 Danek et al.
9,943,684 B2 4/2018 Nuccitelli et al.
9,956,391 B2 5/2018 Weissberg et al.
9,974,609 B2 5/2018 Hollett et al.
9,987,081 B1 6/2018 Bowers et al.
9,993,296 B2 6/2018 Ladtkow et al.
9,999,465 B2 6/2018 Long et al.
10,010,666 B2 7/2018 Rubinsky et al.
10,016,232 B1 7/2018 Bowers et al.
D831,199 S 10/2018 Holton et al.
D832,426 S 10/2018 Holton et al.
10,130,423 B1 11/2018 Viswanathan et al.
10,136,943 B1 11/2018 Cosman, Jr. et al.
10,143,512 B2 12/2018 Rubinsky et al.
10,143,759 B1 12/2018 Heller et al.
10,149,714 B2 12/2018 Mayse et al.
10,154,869 B2 12/2018 Onik et al.
10,154,874 B2 12/2018 Davalos et al.
10,166,071 B2 1/2019 Sherman et al.
10,172,673 B2 1/2019 Viswanathan et al.
10,238,447 B2 3/2019 Neal et al.
10,245,105 B2 4/2019 Davalos et al.
10,271,893 B2 4/2019 Stewart et al.
10,292,755 B2 5/2019 Arena et al.

(56) References Cited

U.S. PATENT DOCUMENTS 10,322,286 B2 6/2019 Viswanathan et al.
10,391,125 B2 8/2019 Nuccitelli et al.
10,426,847 B2 10/2019 Pierce et al.
10,433,908 B2 10/2019 Viswanathan et al.
10,448,989 B2 10/2019 Arena et al.
10,471,254 B2 11/2019 Sano et al.
10,499,980 B2 12/2019 Shuman et al.
10,617,867 B2 4/2020 Viswanathan et al.
10,639,098 B2 5/2020 Cosman
10,688,300 B2 6/2020 Paul et al.
10,694,972 B2 6/2020 Davalos et al.
10,702,337 B2 7/2020 Waldstreicher et al.
10,722,322 B2 7/2020 Vazales
10,779,887 B2 9/2020 Deem et al.
10,813,688 B2 10/2020 Pearson et al.
10,849,678 B2 12/2020 Onik et al.
10,874,451 B2 12/2020 Athos et al.
10,939,958 B2 3/2021 Waldstreicher et al.
10,945,714 B2 3/2021 Ralph
11,039,819 B2 6/2021 Gonzalez
11,051,871 B2 7/2021 Nuccitelli et al.
11,052,246 B2 7/2021 Stewart et al.
11,065,372 B2 7/2021 Stender et al.
11,071,530 B2 7/2021 Wang et al.
11,167,095 B2 11/2021 Ralph et al.
11,278,349 B2 3/2022 Stewart et al.
11,324,543 B2 5/2022 Waldstreicher et al.
11,369,433 B2 6/2022 Waldstreicher et al.
11,382,681 B2 7/2022 Arena et al.
11,471,208 B2 10/2022 Waldstreicher et al.
11,547,851 B2 1/2023 Krimsky et al.
11,612,335 B2 3/2023 Mosesov et al.
11,638,603 B2 5/2023 Sano et al.
11,696,797 B2 7/2023 Onik
11,723,712 B2 8/2023 Athos et al.
11,733,230 B2 8/2023 Liu et al.
11,737,810 B2 8/2023 Davalos et al.
11,903,690 B2 2/2024 Davalos et al.
11,938,317 B2 3/2024 Krimsky et al.
11,952,568 B2 4/2024 Neal, II et al.
12,059,197 B2 8/2024 Davalos et al.
12,150,700 B2 11/2024 Stewart et al.
12,173,280 B2 12/2024 Neal, II et al.
12,178,496 B2 12/2024 Jauregui Johnston et al.
12,201,349 B2 1/2025 Pearson et al.
12,207,866 B2 1/2025 Stewart et al.
12,349,967 B2 7/2025 Waldstreicher et al.
12,390,272 B2 8/2025 Mickelsen
12,402,942 B2 9/2025 Stewart et al.
12,403,305 B2 9/2025 Waldstreicher et al.
12,458,433 B2 11/2025 Akagane et al.
12,458,434 B2 11/2025 O'Brien et al.
12,575,879 B2 3/2026 Waldstreicher et al.
12,599,432 B2 4/2026 Gleiman et al.
12,685,578 B2 7/2026 Castellvi et al.
12,691,281 B2 7/2026 Neal, II et al.
2001/0008016 A1 7/2001 Kotani et al.
2001/0020166 A1 9/2001 Daly et al.
2002/0010491 A1 1/2002 Schoenbach et al.
2002/0022839 A1 2/2002 Stewart et al.
2002/0103483 A1 8/2002 Edwards
2002/0104318 A1 8/2002 Jaafar et al.
2002/0115991 A1 8/2002 Edwards
2002/0188242 A1 12/2002 Wu
2002/0198567 A1 12/2002 Keisari et al.
2003/0130711 A1* 7/2003 Pearson ............. A61B 18/1477
607/101
2003/0158477 A1 8/2003 Panescu
2003/0170898 A1 9/2003 Gundersen et al.
2003/0199050 A1 10/2003 Mangano et al.
2004/0029240 A1 2/2004 Acker
2004/0044338 A1 3/2004 Lennox et al.
2004/0047855 A1 3/2004 Ingenito
2004/0068296 A1 4/2004 Palti
2004/0102818 A1 5/2004 Hakky et al.
2004/0158288 A1 8/2004 Keisari et al.
2004/0176804 A1 9/2004 Palti
2005/0010270 A1 1/2005 Laufer
2005/0049542 A1 3/2005 Sigg et al.
2005/0096584 A1 5/2005 Ferek-Petric
2005/0096644 A1 5/2005 Hall et al.
2005/0096647 A1 5/2005 Steinke et al.
2005/0170510 A1 8/2005 Huang et al.
2005/0171523 A1 8/2005 Rubinsky et al.
2005/0171574 A1 8/2005 Rubinsky et al.
2005/0171575 A1 8/2005 Dev et al.
2005/0177150 A1 8/2005 Amoah et al.
2005/0222646 A1 10/2005 Kroll et al.
2005/0288730 A1 12/2005 Deem et al.
2006/0008808 A1* 1/2006 Yang ................ G01N 33/56972
435/6.16
2006/0162731 A1 7/2006 Wondka et al.
2006/0264752 A1 11/2006 Rubinsky et al.
2006/0269531 A1 11/2006 Beebe et al.
2006/0293725 A1 12/2006 Rubinsky et al.
2006/0293731 A1 12/2006 Rubinsky et al.
2007/0021803 A1 1/2007 Deem et al.
2007/0025919 A1 2/2007 Deem et al.
2007/0083239 A1 4/2007 Demarais et al.
2007/0093802 A1 4/2007 Danek et al.
2007/0106296 A1 5/2007 Laufer et al.
2007/0106348 A1 5/2007 Laufer
2007/0112349 A1 5/2007 Danek et al.
2007/0118184 A1 5/2007 Danek et al.
2007/0118190 A1 5/2007 Danek et al.
2007/0123958 A1 5/2007 Laufer
2007/0129720 A1 6/2007 Demarais et al.
2007/0156135 A1 7/2007 Rubinsky et al.
2007/0191904 A1 8/2007 Libbus et al.
2007/0239213 A1 10/2007 Palti
2008/0015571 A1 1/2008 Rubinsky et al.
2008/0071264 A1 3/2008 Azure
2008/0132884 A1 6/2008 Rubinsky et al.
2008/0132885 A1 6/2008 Rubinsky et al.
2008/0161801 A1 7/2008 Steinke et al.
2008/0195174 A1 8/2008 Walker et al.
2008/0200912 A1 8/2008 Long
2008/0231337 A1 9/2008 Krishnaswamy et al.
2008/0269586 A1 10/2008 Rubinsky et al.
2008/0306570 A1 12/2008 Rezai et al.
2008/0319372 A1 12/2008 Palti et al.
2009/0043301 A1 2/2009 Jarrard et al.
2009/0069797 A1 3/2009 Danek et al.
2009/0118726 A1 5/2009 Auth et al.
2009/0157002 A1 6/2009 Dumot et al.
2009/0192504 A1 7/2009 Askew
2009/0192505 A1 7/2009 Askew et al.
2009/0192508 A1 7/2009 Laufer et al.
2009/0247933 A1 10/2009 Maor et al.
2009/0281477 A1 11/2009 Mikus et al.
2009/0292342 A1 11/2009 Rubinsky et al.
2009/0306644 A1 12/2009 Mayse et al.
2009/0318914 A1 12/2009 Utley et al.
2010/0004623 A1 1/2010 Hamilton, Jr. et al.
2010/0023004 A1 1/2010 Francischelli et al.
2010/0030211 A1* 2/2010 Davalos ................. A61N 1/327
606/41
2010/0121270 A1 5/2010 Gunday et al.
2010/0130975 A1 5/2010 Long
2010/0147701 A1 6/2010 Field
2010/0152725 A1 6/2010 Pearson et al.
2010/0160906 A1 6/2010 Jarrard
2010/0179530 A1 7/2010 Long et al.
2010/0204688 A1 8/2010 Hoey et al.
2010/0228248 A1 9/2010 Griffin
2010/0240995 A1 9/2010 Nuccitelli et al.
2010/0250209 A1* 9/2010 Pearson ................. A61B 34/10
703/2
2010/0256628 A1 10/2010 Pearson et al.
2010/0256630 A1 10/2010 Hamilton, Jr. et al.
2010/0261994 A1 10/2010 Davalos et al.
2010/0274236 A1 10/2010 Krimsky
2010/0324616 A1 12/2010 Livnat et al.
2011/0105726 A1 5/2011 Rosen et al.

(56) References Cited

U.S. PATENT DOCUMENTS

2011/0112527 A1 5/2011 Hamilton, Jr. et al.
2011/0118732 A1 5/2011 Rubinsky et al.
2011/0152855 A1 6/2011 Mayse et al.
2011/0166565 A1 7/2011 Wizeman et al.
2011/0190662 A1 8/2011 Mcweeney
2011/0196288 A1 8/2011 Kaplan et al.
2011/0202052 A1 8/2011 Gelbart et al.
2011/0208166 A1 8/2011 Dumot et al.
2011/0288545 A1 11/2011 Beebe et al.
2012/0098351 A1 4/2012 Ross
2012/0109122 A1 5/2012 Arena et al.
2012/0143120 A1 6/2012 Goldfarb et al.
2012/0150172 A1 6/2012 Ortiz et al.
2012/0197243 A1 8/2012 Sherman et al.
2012/0220998 A1 8/2012 Long et al.
2012/0220999 A1 8/2012 Long
2012/0226101 A1 9/2012 Tinkham et al.
2012/0226271 A1 9/2012 Callas et al.
2012/0277741 A1 11/2012 Davalos et al.
2012/0310230 A1* 12/2012 Willis .................... A61N 1/327 606/41
2012/0310237 A1 12/2012 Swanson
2012/0315704 A1 12/2012 Beebe et al.
2012/0330299 A1 12/2012 Webster et al.
2012/0330306 A1 12/2012 Long et al.
2013/0006144 A1 1/2013 Clancy et al.
2013/0023873 A1 1/2013 Danek et al.
2013/0030425 A1 1/2013 Stewart et al.
2013/0030430 A1 1/2013 Stewart et al.
2013/0035747 A1 2/2013 Danek et al.
2013/0184702 A1 7/2013 Neal, II et al.
2013/0196441 A1 8/2013 Rubinsky et al.
2013/0211402 A1 8/2013 Danek et al.
2013/0218158 A1 8/2013 Danek et al.
2013/0225996 A1 8/2013 Dillard et al.
2013/0226167 A1 8/2013 Kaplan et al.
2013/0253415 A1 9/2013 Sano et al.
2013/0261389 A1 10/2013 Long
2013/0261683 A1 10/2013 Soikum et al.
2014/0018789 A1 1/2014 Kaplan et al.
2014/0018790 A1 1/2014 Kaplan et al.
2014/0025063 A1 1/2014 Kaplan et al.
2014/0039489 A1 2/2014 Davalos, V et al.
2014/0039491 A1 2/2014 Bakos et al.
2014/0046322 A1 2/2014 Callas et al.
2014/0052126 A1 2/2014 Long et al.
2014/0058294 A1 2/2014 Gross et al.
2014/0066913 A1 3/2014 Sherman
2014/0074078 A1 3/2014 Kumar et al.
2014/0081263 A1 3/2014 Mesallum
2014/0107478 A1 4/2014 Seward et al.
2014/0114378 A1 4/2014 Danek et al.
2014/0121663 A1 5/2014 Pearson et al.
2014/0128949 A1 5/2014 Hollett et al.
2014/0148635 A1 5/2014 Danek et al.
2014/0296844 A1 10/2014 Kevin et al.
2014/0324036 A1 10/2014 Sachs et al.
2014/0324037 A1 10/2014 Hoey et al.
2014/0330332 A1 11/2014 Danek et al.
2014/0341801 A1 11/2014 Laufer et al.
2014/0358066 A1* 12/2014 Nuccitelli ............. A61B 18/14 604/20
2014/0378964 A1 12/2014 Pearson
2015/0005766 A1 1/2015 Rioux et al.
2015/0025605 A1 1/2015 Kaplan et al.
2015/0038959 A1 2/2015 Biggs et al.
2015/0039059 A1 2/2015 Mokelke et al.
2015/0045788 A1 2/2015 Litscher et al.
2015/0066005 A1 3/2015 Fan et al.
2015/0066108 A1 3/2015 Shi et al.
2015/0080884 A1 3/2015 Zarins et al.
2015/0088120 A1 3/2015 Garcia et al.
2015/0105775 A1 4/2015 Wizeman et al.
2015/0112321 A1 4/2015 Cadouri
2015/0119879 A1 4/2015 Jameson et al.
2015/0141984 A1 5/2015 Loomas et al.
2015/0150618 A1 6/2015 Onik et al.
2015/0164584 A1 6/2015 Davalos et al.
2015/0173943 A1 6/2015 Loomas et al.
2015/0182282 A1 7/2015 Zemel et al.
2015/0182560 A1 7/2015 Calle et al.
2015/0201996 A1 7/2015 Rubinsky et al.
2015/0223879 A1 8/2015 Danek et al.
2015/0230855 A1 8/2015 Chornenky et al.
2015/0258352 A1 9/2015 Lin et al.
2015/0289923 A1 10/2015 Davalos et al.
2015/0305794 A1 10/2015 Danek et al.
2015/0313664 A1 11/2015 Jarrard
2015/0320478 A1 11/2015 Cosman, Jr. et al.
2015/0320479 A1 11/2015 Cosman, Jr. et al.
2015/0320999 A1 11/2015 Nuccitelli et al.
2015/0327944 A1 11/2015 Neal, II et al.
2015/0342669 A1 12/2015 Flanagan et al.
2016/0000499 A1 1/2016 Lennox et al.
2016/0008016 A1 1/2016 Cioanta et al.
2016/0008066 A1 1/2016 Kaplan et al.
2016/0022349 A1 1/2016 Woloszko et al.
2016/0030014 A1 2/2016 McWeeney et al.
2016/0030016 A1 2/2016 McWeeney et al.
2016/0038230 A1 2/2016 Danek et al.
2016/0058493 A1 3/2016 Neal, II et al.
2016/0066977 A1 3/2016 Neal, II et al.
2016/0066990 A1 3/2016 Kaplan et al.
2016/0074091 A1 3/2016 Amoah et al.
2016/0081745 A1 3/2016 Rajagopalan et al.
2016/0113703 A1 4/2016 Danek et al.
2016/0128767 A1 5/2016 Azamian et al.
2016/0166310 A1* 6/2016 Stewart .............. A61B 18/1492 606/34
2016/0199131 A1 7/2016 Allison et al.
2016/0206370 A1 7/2016 Fruland et al.
2016/0213922 A1 7/2016 Goldberg et al.
2016/0235974 A1 8/2016 Holochwost et al.
2016/0262601 A1 9/2016 Viebach et al.
2016/0262795 A1 9/2016 Urbanski et al.
2016/0287314 A1 10/2016 Arena et al.
2016/0296269 A1* 10/2016 Rubinsky .................. C25B 1/26
2016/0303293 A1 10/2016 Doyle et al.
2016/0310211 A1 10/2016 Long
2016/0324573 A1 11/2016 Mickelson et al.
2016/0331441 A1 11/2016 Konings
2016/0338758 A9 11/2016 Davalos et al.
2016/0354142 A1 12/2016 Pearson et al.
2016/0354145 A1 12/2016 Stern et al.
2016/0361109 A1 12/2016 Weaver et al.
2016/0367310 A1 12/2016 Onik et al.
2017/0000584 A1 1/2017 Blanco et al.
2017/0035499 A1 2/2017 Stewart et al.
2017/0049513 A1 2/2017 Cosman, Jr. et al.
2017/0065330 A1 3/2017 Mickelsen et al.
2017/0065339 A1 3/2017 Mickelsen
2017/0065340 A1 3/2017 Long
2017/0065343 A1 3/2017 Mickelsen
2017/0087224 A1 3/2017 Quake
2017/0105763 A1 4/2017 Karve et al.
2017/0105793 A1 4/2017 Cao et al.
2017/0117603 A1 4/2017 Kreis et al.
2017/0119465 A1 5/2017 Long et al.
2017/0135723 A1 5/2017 Zarembinski
2017/0156783 A1 6/2017 McKernon et al.
2017/0188793 A1 7/2017 OuYang et al.
2017/0189097 A1 7/2017 Viswanathan et al.
2017/0189579 A1 7/2017 Davalos
2017/0215939 A1 8/2017 Palti et al.
2017/0215953 A1 8/2017 Long et al.
2017/0216353 A1 8/2017 Nuccitelli et al.
2017/0216585 A1 8/2017 Goldfarb et al.
2017/0224363 A1 8/2017 Watanabe et al.
2017/0239480 A1 8/2017 Zarins et al.
2017/0246455 A1 8/2017 Athos et al.
2017/0252090 A1 9/2017 Smith et al.
2017/0266283 A1 9/2017 Soikum et al.
2017/0266438 A1 9/2017 Sano et al.
2017/0281934 A1 10/2017 Giladi et al.

(56) References Cited

U.S. PATENT DOCUMENTS

2017/0304002 A1 10/2017 Beebe et al.
2017/0311789 A1 11/2017 Mulcahey et al.
2017/0312021 A1 11/2017 Pilcher et al.
2017/0319843 A1 11/2017 Beebe et al.
2017/0319851 A1 11/2017 Athos et al.
2017/0325894 A1 11/2017 Krimsky
2017/0326361 A1 11/2017 Kreis et al.
2017/0333104 A1 11/2017 Forde et al.
2017/0333109 A1 11/2017 Gilbert
2017/0333112 A1 11/2017 Nuccitelli et al.
2017/0360326 A1 12/2017 Davalos et al.
2018/0000895 A1 1/2018 Pierce et al.
2018/0001056 A1 1/2018 Leeflang et al.
2018/0008127 A1 1/2018 Tinkham et al.
2018/0014868 A1 1/2018 O'Connor et al.
2018/0028250 A1 2/2018 O'Connor
2018/0028267 A1 2/2018 Onik et al.
2018/0036058 A1 2/2018 Fan et al.
2018/0042655 A1 2/2018 Burr et al.
2018/0042674 A1 2/2018 Mickelsen
2018/0042675 A1 2/2018 Long
2018/0043153 A1 2/2018 Viswanathan et al.
2018/0064488 A1 3/2018 Long et al.
2018/0071014 A1 3/2018 Neal et al.
2018/0078755 A1 3/2018 Kreis et al.
2018/0085160 A1 3/2018 Viswanathan et al.
2018/0085575 A1 3/2018 Travers et al.
2018/0104486 A1 4/2018 Yoon et al.
2018/0110557 A1 4/2018 Muratori et al.
2018/0110978 A1 4/2018 Beebe et al.
2018/0125565 A1 5/2018 Sano et al.
2018/0132922 A1 5/2018 Neal, II
2018/0153467 A1 6/2018 Lichtenstein et al.
2018/0153937 A1 6/2018 Nuccitelli et al.
2018/0154142 A1 6/2018 Guo et al.
2018/0161086 A1 6/2018 Davalos et al.
2018/0193082 A1 7/2018 Rubinsky et al.
2018/0193088 A1 7/2018 Sutton et al.
2018/0200510 A1 7/2018 Nuccitelli et al.
2018/0221078 A1 8/2018 Howard et al.
2018/0256240 A1 9/2018 Bloom et al.
2018/0263685 A1 9/2018 Onik et al.
2018/0289954 A1 10/2018 Hebb et al.
2018/0303543 A1 10/2018 Stewart et al.
2018/0311497 A1 11/2018 Viswanathan et al.
2018/0344378 A1 12/2018 Wolf et al.
2018/0360531 A1 12/2018 Holmes, Jr. et al.
2019/0022333 A1 1/2019 Baillargeon et al.
2019/0030328 A1 1/2019 Stewart et al.
2019/0038171 A1 2/2019 Howard
2019/0038895 A1 2/2019 Pianca et al.
2019/0046791 A1 2/2019 Ebbers et al.
2019/0059864 A1 2/2019 Gonzalez
2019/0069950 A1 3/2019 Viswanathan et al.
2019/0083169 A1 3/2019 Single et al.
2019/0099214 A1 4/2019 Rubinsky et al.
2019/0105408 A1 4/2019 Heller et al.
2019/0117963 A1 4/2019 Travers et al.
2019/0117969 A1 4/2019 Schmidt et al.
2019/0126037 A1 5/2019 Ivorra
2019/0151015 A1 5/2019 Viswanathan et al.
2019/0160283 A1 5/2019 Nuccitelli et al.
2019/0201089 A1 7/2019 Waldstreicher et al.
2019/0216899 A1 7/2019 Bright
2019/0223938 A1 7/2019 Arena et al.
2019/0223943 A1 7/2019 Forsyth et al.
2019/0232048 A1 8/2019 Latouche et al.
2019/0239949 A1 8/2019 Nuccitelli et al.
2019/0254735 A1 8/2019 Stewart et al.
2019/0269826 A1 9/2019 Peyman
2019/0269912 A1 9/2019 Viswanathan et al.
2019/0275260 A1 9/2019 Ralph et al.
2019/0282294 A1 9/2019 Davalos et al.
2019/0299019 A1 10/2019 Chornenky et al.
2019/0307781 A1 10/2019 Krex et al.
2019/0328445 A1 10/2019 Sano et al.
2019/0350971 A1 11/2019 Nuccitelli et al.
2019/0351224 A1 11/2019 Sano et al.
2019/0365362 A1 12/2019 Ralph
2020/0000938 A1 1/2020 Pierce et al.
2020/0009377 A1 1/2020 Chang et al.
2020/0016067 A1 1/2020 Gotlib et al.
2020/0038093 A1 2/2020 Onik
2020/0046423 A1 2/2020 Viswanathan et al.
2020/0046967 A1 2/2020 Ivey et al.
2020/0060754 A1 2/2020 Shuman et al.
2020/0060755 A1 2/2020 Shuman et al.
2020/0078047 A1 3/2020 Lambe et al.
2020/0129228 A1 4/2020 Henkes et al.
2020/0147371 A1 5/2020 Pakhomov et al.
2020/0260987 A1 8/2020 Davalos et al.
2020/0275973 A1 9/2020 O'Brien et al.
2020/0298008 A1 9/2020 Asirvatham
2020/0323583 A1* 10/2020 Qiao .................... A61B 18/149
2020/0398048 A1 12/2020 Krimsky et al.
2021/0022794 A1 1/2021 Viswanathan
2021/0023362 A1 1/2021 Lorenzo et al.
2021/0038280 A1 2/2021 Pikramenos
2021/0052822 A1 2/2021 Matsumoto et al.
2021/0052882 A1* 2/2021 Wasson ................ A61N 1/0412
2021/0085777 A1* 3/2021 Steinmetz ............... A61P 35/04
2021/0137410 A1 5/2021 O'Brien et al.
2021/0146126 A1 5/2021 Waldstreicher et al.
2021/0161582 A1 6/2021 Byrd et al.
2021/0212755 A1 7/2021 Jimenez et al.
2021/0236815 A1 8/2021 Waldstreicher et al.
2021/0236816 A1 8/2021 Waldstreicher et al.
2021/0315639 A1* 10/2021 Manucherhabadi ... A61B 34/10
2021/0393327 A1 12/2021 Eyster et al.
2022/0054188 A1 2/2022 Palushi et al.
2022/0104875 A1 4/2022 Gleiman et al.
2022/0161027 A1 5/2022 Aycock et al.
2022/0233237 A1 7/2022 Adams et al.
2022/0249157 A1 8/2022 Viswanathan et al.
2022/0273353 A1 9/2022 Howard et al.
2022/0330886 A1 10/2022 Varadan et al.
2022/0387095 A1 12/2022 Neal et al.
2022/0395323 A1 12/2022 Waldstreicher et al.
2023/0082389 A1 3/2023 Waldstreicher et al.
2023/0149706 A1 5/2023 Krimsky et al.
2023/0165629 A1 6/2023 Tehrani et al.
2023/0172650 A1 6/2023 Castellvi et al.
2023/0240746 A1 8/2023 Gundert et al.
2023/0248414 A1 8/2023 Sano et al.
2023/0329784 A1 10/2023 Stewart et al.
2023/0405313 A1 12/2023 Pastori et al.
2024/0032984 A1 2/2024 Castellvi et al.
2024/0156518 A1 5/2024 Wong et al.
2024/0173557 A1 5/2024 Neal, II et al.
2024/0180878 A1 6/2024 Spera
2024/0216038 A1 7/2024 Girouard et al.
2024/0252225 A1 8/2024 Fraasch et al.
2024/0277245 A1 8/2024 Davalos et al.
2024/0299091 A1 9/2024 Kwaku et al.
2024/0350187 A1 10/2024 Waldstreicher et al.
2024/0390672 A1 11/2024 Neal et al.
2025/0032787 A1 1/2025 Krimsky et al.
2025/0040985 A1 2/2025 Girouard et al.
2025/0064510 A1 2/2025 Waldstreicher et al.
2025/0099172 A1 3/2025 Cope et al.
2025/0213299 A1 7/2025 Nafie et al.
2025/0261991 A1 8/2025 O'Brien et al.
2025/0288349 A1 9/2025 Rubinsky et al.
2025/0295442 A1 9/2025 Darwish et al.
2025/0332411 A1 10/2025 Paul et al.
2026/0014371 A1 1/2026 Krimsky et al.
2026/0137438 A1 5/2026 Hunter et al.
2026/0151177 A1 6/2026 Waldstreicher et al.

(56) References Cited

U.S. PATENT DOCUMENTS

| | | | |
|---|---|---|---|
| 2026/0151621 | A1 | 6/2026 | Neal, II et al. |
| 2026/0177552 | A1 | 6/2026 | Pastori |

FOREIGN PATENT DOCUMENTS

| | | | |
|---|---|---|---|
| AU | 2004235684 | A1 | 1/2005 |
| AU | 2015355241 | A1 | 6/2017 |
| AU | 2016246146 | A1 | 10/2017 |
| AU | 2020200688 | B2 | 7/2021 |
| CA | 2370223 | A1 | 10/2000 |
| CA | 2981867 | A1 | 10/2016 |
| CN | 1867299 | A | 11/2006 |
| CN | 101198287 | A | 6/2008 |
| CN | 101426551 | A | 5/2009 |
| CN | 101553180 | A | 10/2009 |
| CN | 101909649 | A | 12/2010 |
| CN | 102014779 | A | 4/2011 |
| CN | 102105115 | A | 6/2011 |
| CN | 102421386 | A | 4/2012 |
| CN | 102725021 | A | 10/2012 |
| CN | 103027745 | A | 4/2013 |
| CN | 103252016 | A | 8/2013 |
| CN | 103281978 | A | 9/2013 |
| CN | 103313671 | A | 9/2013 |
| CN | 103379873 | A | 10/2013 |
| CN | 103582463 | A | 2/2014 |
| CN | 103750899 | A | 4/2014 |
| CN | 103781433 | A | 5/2014 |
| CN | 103796603 | A | 5/2014 |
| CN | 104080418 | A | 10/2014 |
| CN | 104363849 | A | 2/2015 |
| CN | 104470454 | A | 3/2015 |
| CN | 104602634 | A | 5/2015 |
| CN | 104602754 | A | 5/2015 |
| CN | 104703557 | A | 6/2015 |
| CN | 105073051 | A | 11/2015 |
| CN | 105939686 | A | 9/2016 |
| CN | 107194119 | A | 9/2017 |
| CN | 107205772 | A | 9/2017 |
| CN | 107921258 | A | 4/2018 |
| CN | 108024803 | A | 5/2018 |
| CN | 108778172 | A | 11/2018 |
| CN | 108778173 | A | 11/2018 |
| CN | 109788979 | A | 5/2019 |
| CN | 110573104 | A | 12/2019 |
| CN | 113558744 | A | 10/2021 |
| CO | 2017010662 | A2 | 3/2018 |
| DE | 60023283 | T2 | 7/2006 |
| DK | 0987989 | T3 | 10/2006 |
| EP | 1173103 | A2 | 1/2002 |
| EP | 0935482 | B1 | 5/2005 |
| EP | 1173103 | B1 | 10/2005 |
| EP | 1804905 | A1 | 7/2007 |
| EP | 1991303 | A2 | 11/2008 |
| EP | 2170198 | A1 | 4/2010 |
| EP | 2317951 | A1 | 5/2011 |
| EP | 2413833 | A1 | 2/2012 |
| EP | 2488251 | A2 | 8/2012 |
| EP | 2642937 | A2 | 10/2013 |
| EP | 2661236 | A1 | 11/2013 |
| EP | 2736432 | A1 | 6/2014 |
| EP | 2762195 | A2 | 8/2014 |
| EP | 2777579 | A1 | 9/2014 |
| EP | 2170198 | B1 | 4/2015 |
| EP | 1648555 | B1 | 9/2015 |
| EP | 2957248 | A1 | 12/2015 |
| EP | 1804905 | B1 | 2/2016 |
| EP | 2736432 | B1 | 3/2016 |
| EP | 3003461 | A2 | 4/2016 |
| EP | 2661236 | B1 | 8/2016 |
| EP | 3091925 | A1 | 11/2016 |
| EP | 3113605 | A1 | 1/2017 |
| EP | 3142584 | A1 | 3/2017 |
| EP | 3143124 | A1 | 3/2017 |
| EP | 3154464 | A1 | 4/2017 |
| EP | 3003470 | B1 | 8/2017 |
| EP | 3226794 | A1 | 10/2017 |
| EP | 3282953 | A1 | 2/2018 |
| EP | 3290082 | A2 | 3/2018 |
| EP | 3139997 | B1 | 9/2018 |
| EP | 3113605 | B1 | 10/2018 |
| EP | 3399931 | A1 | 11/2018 |
| EP | 3399933 | A1 | 11/2018 |
| EP | 3154463 | B1 | 3/2019 |
| EP | 3471631 | A1 | 4/2019 |
| EP | 2994045 | B1 | 5/2019 |
| EP | 3003461 | B1 | 5/2019 |
| EP | 3091921 | B1 | 6/2019 |
| EP | 3456278 | A3 | 6/2019 |
| EP | 3495018 | A1 | 6/2019 |
| EP | 3206613 | B1 | 7/2019 |
| EP | 3569144 | A1 | 11/2019 |
| ES | 2246853 | T3 | 3/2006 |
| ES | 2361460 | T3 | 6/2011 |
| IN | 200601622 | | 5/2007 |
| JP | H09285182 | A | 10/1997 |
| JP | 2001103741 | A | 4/2001 |
| JP | 2001506157 | A | 5/2001 |
| JP | 2002065626 | A | 3/2002 |
| JP | 2002541905 | A | 12/2002 |
| JP | 2003529401 | A | 10/2003 |
| JP | 2004516867 | A | 6/2004 |
| JP | 2006320176 | A | 11/2006 |
| JP | 2007504910 | A | 3/2007 |
| JP | 4242436 | B2 | 3/2009 |
| JP | 4243436 | B2 | 3/2009 |
| JP | 2010509032 | A | 3/2010 |
| JP | 2011519699 | A | 7/2011 |
| JP | 2011524785 | A | 9/2011 |
| JP | 2012515018 | A | 7/2012 |
| JP | 2013543745 | A | 12/2013 |
| JP | 2015128596 | A | 7/2015 |
| JP | 2015524732 | A | 8/2015 |
| JP | 2016195826 | A | 11/2016 |
| JP | 2017518805 | A | 7/2017 |
| JP | 2017529169 | A | 10/2017 |
| JP | 2018532403 | A | 11/2018 |
| JP | 2019500170 | A | 1/2019 |
| JP | 2019524396 | A | 9/2019 |
| JP | 2019530529 | A | 10/2019 |
| JP | 2020518335 | A | 6/2020 |
| JP | 2021500153 | A | 1/2021 |
| JP | 2021508533 | A | 3/2021 |
| JP | 2023536906 | A | 8/2023 |
| PT | 987989 | E | 11/2006 |
| WO | WO-9814238 | A1 | 4/1998 |
| WO | WO-9906101 | A1 | 2/1999 |
| WO | WO-2000062699 | A2 | 10/2000 |
| WO | WO-0110319 | A1 | 2/2001 |
| WO | WO-2001055294 | A1 | 8/2001 |
| WO | WO-2002032333 | A1 | 4/2002 |
| WO | WO-02098501 | A2 | 12/2002 |
| WO | WO-03047684 | A2 | 6/2003 |
| WO | WO-2004037341 | A2 | 5/2004 |
| WO | WO-2004110371 | A2 | 12/2004 |
| WO | WO-2005044371 | A1 | 5/2005 |
| WO | WO-2005065284 | A2 | 7/2005 |
| WO | WO-2005065284 | A3 | 11/2005 |
| WO | WO-2005115535 | A2 | 12/2005 |
| WO | WO-2005032646 | A3 | 4/2006 |
| WO | WO-2006036706 | A1 | 4/2006 |
| WO | WO-2006052940 | A2 | 5/2006 |
| WO | WO-2006085150 | A2 | 8/2006 |
| WO | WO-2006116198 | A2 | 11/2006 |
| WO | WO-2006116608 | A2 | 11/2006 |
| WO | WO-2006131816 | A2 | 12/2006 |
| WO | WO-2007001747 | A2 | 1/2007 |
| WO | WO-2007001751 | A1 | 1/2007 |
| WO | WO-2007039799 | A3 | 7/2007 |
| WO | WO-2007100727 | A2 | 9/2007 |
| WO | WO-2007103070 | A2 | 9/2007 |
| WO | WO-2008034100 | A2 | 3/2008 |
| WO | WO-2008063195 | A1 | 5/2008 |
| WO | WO-2008087489 | A2 | 7/2008 |

(56) References Cited

FOREIGN PATENT DOCUMENTS

| | | | |
|---|---|---|---|
| WO | WO-2009009398 | A1 | 1/2009 |
| WO | WO-2009137800 | A2 | 11/2009 |
| WO | WO-2009137819 | A1 | 11/2009 |
| WO | WO-2009154654 | A1 | 12/2009 |
| WO | WO-2010014480 | A1 | 2/2010 |
| WO | WO-2010022275 | A1 | 2/2010 |
| WO | WO-2010080974 | A1 | 7/2010 |
| WO | WO-2010093692 | A2 | 8/2010 |
| WO | WO-2010107947 | A1 | 9/2010 |
| WO | WO-2010117806 | A1 | 10/2010 |
| WO | WO-2010118387 | A1 | 10/2010 |
| WO | WO-2010141417 | A2 | 12/2010 |
| WO | WO-2010151277 | A1 | 12/2010 |
| WO | WO-2011047387 | A2 | 4/2011 |
| WO | WO-2011135294 | A1 | 11/2011 |
| WO | WO-2012071526 | A2 | 5/2012 |
| WO | WO-2012088149 | A2 | 6/2012 |
| WO | WO-2012118659 | A1 | 9/2012 |
| WO | WO-2013052501 | A1 | 4/2013 |
| WO | WO-2014025394 | A1 | 2/2014 |
| WO | WO-2014105964 | A1 | 7/2014 |
| WO | WO-2014181167 | A1 | 11/2014 |
| WO | WO-2014197240 | A2 | 12/2014 |
| WO | WO-2014197632 | A2 | 12/2014 |
| WO | WO-2014204978 | A1 | 12/2014 |
| WO | WO-2015073877 | A1 | 5/2015 |
| WO | WO-2015073885 | A1 | 5/2015 |
| WO | WO-2015085162 | A1 | 6/2015 |
| WO | WO-2015103530 | A1 | 7/2015 |
| WO | WO-2015103574 | A1 | 7/2015 |
| WO | WO-2015171921 | A2 | 11/2015 |
| WO | WO-2015175570 | A1 | 11/2015 |
| WO | WO-2015192018 | A1 | 12/2015 |
| WO | WO-2015192027 | A1 | 12/2015 |
| WO | WO-2016014264 | A1 | 1/2016 |
| WO | WO-2016036891 | A1 | 3/2016 |
| WO | WO-2016060983 | A1 | 4/2016 |
| WO | WO-2016061002 | A1 | 4/2016 |
| WO | WO-2016089781 | A1 | 6/2016 |
| WO | WO-2016100325 | A1 | 6/2016 |
| WO | WO-2016112359 | A1 | 7/2016 |
| WO | WO-2016123608 | A2 | 8/2016 |
| WO | WO-2016126778 | A1 | 8/2016 |
| WO | WO-2016149575 | A1 | 9/2016 |
| WO | WO-2016154473 | A1 | 9/2016 |
| WO | WO-2016164930 | A1 | 10/2016 |
| WO | WO-2016178697 | A1 | 11/2016 |
| WO | WO-2016179712 | A1 | 11/2016 |
| WO | WO-2016180934 | A1 | 11/2016 |
| WO | WO-2016201264 | A1 | 12/2016 |
| WO | WO-2017024123 | A1 | 2/2017 |
| WO | WO-2017109261 | A1 | 6/2017 |
| WO | WO-2017114001 | A1 | 7/2017 |
| WO | WO-2017119934 | A1 | 7/2017 |
| WO | WO-2017120169 | A1 | 7/2017 |
| WO | WO-2017151260 | A1 | 9/2017 |
| WO | WO-2017173089 | A1 | 10/2017 |
| WO | WO-2017175116 | A1 | 10/2017 |
| WO | WO-2017200954 | A1 | 11/2017 |
| WO | WO-2017201394 | A1 | 11/2017 |
| WO | WO-2017218734 | A1 | 12/2017 |
| WO | WO-2018005511 | A1 | 1/2018 |
| WO | WO-2018010659 | A1 | 1/2018 |
| WO | WO-2018026985 | A1 | 2/2018 |
| WO | WO-2018065806 | A1 | 4/2018 |
| WO | WO-2018067999 | A1 | 4/2018 |
| WO | WO-2018075946 | A1 | 4/2018 |
| WO | WO-2018106672 | A1 | 6/2018 |
| WO | WO-2018187244 | A2 | 10/2018 |
| WO | WO-2018200800 | A1 | 11/2018 |
| WO | WO-2018201037 | A1 | 11/2018 |
| WO | WO-2019032474 | A1 | 2/2019 |
| WO | WO-2019055512 | A1 | 3/2019 |
| WO | WO-2019084011 | A1 | 5/2019 |
| WO | WO-2019095604 | A1 | 5/2019 |
| WO | WO-2019100016 | A1 | 5/2019 |
| WO | WO-2019108540 | A1 | 6/2019 |
| WO | WO-2019133606 | A1 | 7/2019 |
| WO | WO-2019133608 | A1 | 7/2019 |
| WO | WO-2019157359 | A1 | 8/2019 |
| WO | WO-2019178500 | A1 | 9/2019 |
| WO | WO-2019197973 | A1 | 10/2019 |
| WO | WO-2020005186 | A2 | 1/2020 |
| WO | WO-2020010188 | A1 | 1/2020 |
| WO | WO-2020018662 | A1 | 1/2020 |
| WO | WO-2020061192 | A1 | 3/2020 |
| WO | WO-2020096836 | A2 | 5/2020 |
| WO | WO-2020118383 | A1 | 6/2020 |
| WO | WO-2020150709 | A1 | 7/2020 |
| WO | WO-2020215007 | A1 | 10/2020 |
| WO | WO-2021011733 | | 1/2021 |
| WO | WO-2021108292 | A1 | 6/2021 |
| WO | WO-2021127558 | A1 | 6/2021 |
| WO | WO-2021207385 | A1 | 10/2021 |
| WO | WO-2022031797 | A1 | 2/2022 |
| WO | WO-2022204479 | A1 | 9/2022 |
| WO | WO-2022260723 | A1 | 12/2022 |
| WO | WO-2022261418 | A1 | 12/2022 |
| WO | WO-2023044124 | A1 | 3/2023 |
| WO | WO-2023172773 | A1 | 9/2023 |
| WO | WO-2023212250 | A1 | 11/2023 |
| WO | WO-2023220419 | A1 | 11/2023 |
| WO | WO-2024196823 | A2 | 9/2024 |
| WO | WO-2024254966 | A1 | 12/2024 |
| WO | WO-2025043024 | A2 | 2/2025 |
| WO | WO-2025081663 | A1 | 4/2025 |
| WO | WO-2025085827 | A1 | 4/2025 |
| WO | WO-2025106708 | A1 | 5/2025 |
| WO | WO-2025128495 | A1 | 6/2025 |
| WO | WO-2025160398 | A2 | 7/2025 |
| WO | WO-2025235871 | A1 | 11/2025 |
| WO | WO-2026080662 | A1 | 4/2026 |

OTHER PUBLICATIONS

A. Valipour, et al. *First-in-Human Results of Bronchial Rheoplasty: An Endobronchial Treatment for Chronic Bronchitis (CB)*, Epidemiology and Therapy, Mini Symposium, May 22, 2019, Abstract.

Appelbaum et al., US Findings after Irreversible Electroporation Ablation: Radiologic-Pathologic Correlation, Radiology: vol. 262: No. 1—Jan. 2012.

Arschang Valipour et al. *Bronchial Rheoplasty for Treatment of Chronic Bronchitis*, American Journal of Respritory and Critical Care Medicine, vol. 202, No. 5, Sep. 1, 2020, pp. 681-689.

Arschang Valipour et al. Bronchial Rheoplasty for Treatment of Chronic Bronchitis. Twelve-Month Results from a Multicenter Clinical Trial, American Journal of Respiratory and Critical Care Medicine, vol. 202, Issue 5, 2019.

Arschang Valipour, et al. Late Breaking Abstract—Bronchial Rheoplasty for Treatment of Chronic Bronchitis: 6 Month Results from a Prospective Multi-Center Study, Abstract, European Respiratory Journal 2019, pp. 1-5.

Charalambous et al., The Efficacy and Safety of the Open Approach Irreversible Electroporation in the Treatment of Pancreatic Cancer: A Systematic Review, European Journal of Surgical Oncology; vol. 46, No. 9, Sep. 2020.

Davalos et al., Implications and Considerations of Thermal Effects When Applying Irreversible ElectroporationTissue Ablation Therapy, Prostate;vol. 75, No. 10; pp. 1114-1118, Jul. 1, 2015.

Edd et al., In Vivo Results of a New Focal Tissue Ablation Technique: Irreversible Electroporation, IEEE Transactions on Biomedical Engineering, vol. 53, No. 5; pp. 1409-1415; Jun. 2006.

EP18836576.1 Search Report dated Jun. 8, 2021.

EP20792123.0 Extended and Supplementary European Search Report dated Dec. 21, 2022.

EP23178276.4 Extended European Search Report dated Jun. 26, 2023.

Frandsen et al., Calcium electroporation Q4 in three cell lines; a comparison of bleomycin 2 and calcium, calcium compounds, and pulsing conditions, Biochimica et Biophysica Acta, vol. 1840, No. 3; pp. 1204-1208, Mar. 2014.

(56) References Cited

OTHER PUBLICATIONS

International Preliminary Report on Patentability for PCT/US2018/067501 dated Jun. 30, 2020.
International Search Report and Written Opinion for PCT/US2018/067504 on Jun. 30, 2020.
International Search Report and Written Opinion for PCT/US2020/028844 on Sep. 4, 2020.
Kundalia et al., Margin Accentuation for resectable Pancreatic cancer using Irreversible Electroporation e Results from the MACPIE-I study, European Journal of Surgical Oncology, vol. 47, No. 10: pp. 2571-2578; Oct. 2021.
"Lu, et al., "Sequence-Modified Antibiotic Resistance Genes Provide Sustained Plasmid-Mediated Transgene Expression in Mammals" (2017) Molecular Therapy, vol. 25, No. 5, pp. 1187-1198".
Maor et al., Irreversible Electroporation Attenuates Neointimal Formation After Angioplasty, IEEE Transactions on Biomedical Engineering, vol. 55, No. 9, Sep. 2008.
Maor et al., The Effect of Irreversible Electroporation on Blood Vessels, Technology in Cancer Research and Treatment, vol. 6, No. 4, Aug. 2007.
Pallav L Shah, et al. *Epithelial Resurfacing: The Bronchial Skin Peel, American Thoracic Society*, May 22, 2020, pp. 1-8.
PCT/US2018/067501 International Search Report and Written Opinion dated Mar. 13, 2019.
PCT/US2021/026221 International Search Report and Written Opinion dated Jul. 21, 2021.
PCT/US2022/015217 International Search Report and Written Opinion dated May 6, 2022.
PCT/US2022/021888 International Search Report and Written Opinion dated Jun. 16, 2022.
PCT/US2022/044021 International Search Report and Written Opinion dated Jan. 11, 2023.
Reddy et al., Pulsed Field Ablation of Paroxysmal Atrial Fibrillation, JACC Clin Electrophysiology vol. 7 No. 5, pp. 614-627, May 2021.
Rubinsky et al., "Irreversible Electroporation: a New Ablation Modality—Clinical Implications," Tech. Cancer Res. Treatment 6:1-12 (2007).
S. Fernandez-Bussy, et al. *Histopathologic Results Post Bronchial Rheoplasty* , Epidemiology and Therapy, Mini Symposium, May 22, 2019, Abstract.
Timmer et al., Irreversible Electroporation for Locally Advanced Pancreatic Cancer, Techniques in Vascular and Interventional Radiology vol. 23, Issue 2, Jun. 2020.
U.S. Appl. No. 16/914,072 Notice of Allowance dated Jun. 20, 2022.
U.S. Appl. No. 17/214,688 Notice of Allowance dated Feb. 4, 2022.
U.S. Appl. No. 17/214,688 Notice of Allowance dated Mar. 2, 2022.
U.S. Appl. No. 16/914,200 Notice of Allowance dated Sep. 8, 2022.
U.S. Appl. No. 16/914,200 Office Action dated May 4, 2022.
U.S. Appl. No. 16/914,200 Office Action dated Oct. 22, 2021.
U.S. Appl. No. 17/214,688 Office Action dated Sep. 7, 2021.
U.S. Appl. No. 17/502,640 Office Action dated Apr. 28, 2023.
U.S. Appl. No. 17/502,640 Office Action dated Jul. 13, 2022.
U.S. Appl. No. 17/502,640 Office Action dated Mar. 14, 2022.
U.S. Appl. No. 17/502,640 Office Action dated Nov. 27, 2023.
U.S. Appl. No. 18/077,097 Corrected Notice of Allowability dated Dec. 26, 2023.
U.S. Appl. No. 18/077,097 Notice of Allowance dated Oct. 27, 2023.
U.S. Appl. No. 18/077,097 Office Action dated Aug. 3, 2023.
U.S. Appl. No. 17/214,688 Office Action dated May 25, 2021.
U.S. Appl. No. 16/914,072 Office Action dated Nov. 26, 2021.
V. Kim et al. *Bronchial Rheoplasty Increases Distal Airway Volume in Chronic Bronchitis*, European Respiratory Journal 2019, vol. 54, Suppl. 63, PA2040 Abstract.
Valipour, A., Ing, A., Williamson, J., et al. *Late Breaking Abstract—First-in-Human Results of Bronchial Rheoplasty: An Endobronchial Treatment for Chronic Bronchitis* (*CB*). European Respiratory Journal 2018 52: Suppl. 62, OA2162.
Verma et al., Primer on Pulsed Electrical Field Ablation: Understanding the Benefits and Limitations, Circulation: Arrhythmia and Electrophysiology, vol. 14, No. 9, Sep. 20, 2021.
Xie et al., Ablation of Myocardial Tissue With Nanosecond Pulsed Electric Fields, Plos One, vol. 10, No. 12, Dec. 14, 2015.
Yavin et al., Pulsed Field Ablation Using a Lattice Electrode for Focal Energy Delivery, Circulation: Arrhythmia and Electrophysiology, vol. 13, No. 6, May 6, 2020.
Co-pending U.S. Appl. No. 19/197,872, inventors Krimsky; William Sanford et al., filed May 2, 2025.
EP22776703.5 Extended European Search Report dated Dec. 23, 2024.
EP22870831.9 Extended European Search Report dated Jun. 16, 2025.
EP25166670.7 Extended European Search Report dated May 15, 2025.
U.S. Appl. No. 17/502,640 Notice of Allowance dated Sep. 26, 2024.
U.S. Appl. No. 17/502,640 Supplemental Notice of Allowability dated Dec. 23, 2024.
U.S. Appl. No. 17/746,361 Office Action dated Apr. 29, 2025.
U.S. Appl. No. 17/962,142 Office Action dated Apr. 25, 2025.
U.S. Appl. No. 18/416,505 Office Action dated Jul. 14, 2025.
U.S. Appl. No. 18/416,505 Office Action dated Oct. 1, 2024.
U.S. Appl. No. 18/423,043 Office Action dated Nov. 4, 2024.
Co-pending U.S. Appl. No. 18/416,505, inventor Neal; Robert E., filed Jan. 18, 2024.
Co-pending U.S. Appl. No. 18/423,043, inventor Krimsky; William Sanford, filed Jan. 25, 2024.
Co-pending U.S. Appl. No. 18/792,495, inventors O'Brien; Timothy J. et al., filed Aug. 1, 2024.
EP21785398.5 Extended European Search Report dated Apr. 4, 2024.
Al-Sakere, et al., Tumor Ablation with Irreversible Electroporation, *PLoS ONE*, 2(11):e1135. doi:10.1371/journal.pone.0001135 (Nov. 2007).
Arena C.B., et al., "Chapter 10.13: Electroporation Therapy," Comprehensive Biomedical Physics, Springer, Editor: A. Brahme, 2014, vol. 10, pp. 269-287 (20 Pages), Retrieved from URL: http://dx.doi.org/10.1016/8978-0-444-53632-7.01016-9.
Arena C.B., et al., "High-frequency Irreversible Electroporation (H-FIRE) for Non-thermal Ablation without Muscle Contraction," Biomedical Engineering Online, Nov. 21, 2011, vol. 10, Article No. 102, pp. 1-20 (21 Pages).
Arena, et al., High-frequency irreversible electroporation (H-FIRE) for non-thermal ablation without muscle contraction, *BioMedical Engineering OnLine*, 10:102, http://www.biomedical-engineering-online.com/content/10/1/102 (Nov. 2011).
Bertacchini, et al., Design of an Irreversible Electroporation System for Clinical Use, *Technology in Cancer Research and Treatment*, 6(4):313-320 (Aug. 2007).
Bhonsle S., et al., "Characterization of Irreversible Electroporation Ablation with a Validated Perfused Organ Model," Journal of Vascular and Interventional Radiology, 2016, vol. 27, pp. 1913-1922 (12 Pages), Appendix A—Supplemental Materials and Methods.
Campelo S., et al., "An Evaluation of Irreversible Electroporation Thresholds in Human Prostate Cancer and Potential Correlations to Physiological Measurements," APL Bioengineering, 2017, vol. 1 (016101), pp. 016101-1-016101-10, Retrieved from URL: https://doi.org/10.1063/1.5005828.
Cerveri I., et al., "Variations in the Prevalence Across Countries of Chronic Bronchitis and Smoking Habits in Young Adults," The European Respiratory Journal, 2001, vol. 18, No. 1, pp. 85-92.
Cheetham J., et al., "Effects of Functional Electrical Stimulation on Denervated Laryngeal Muscle in a Large Animal Model," Artificial Organs, 2015, vol. 39, No. 10, pp. 876-885.
Criner G.G., "Chronic Bronchitis: The Case for an Unmet Medical Need," European Respiratory Society (ERS), 2017, 13 Pages.
Davalos, et al., Tissue Ablation with Irreversible Electroporation, *Annals of Biomedical Engineering*, 33(2):223-231 (Feb. 2005).

(56) References Cited

OTHER PUBLICATIONS

Dean D.A., "Gene Electrotransfer to Lung," Clinical Aspects of Electroporation, Springer Science Business Media, LLC, Chapter 15, 2011, pp. 165-175.
Dev, et al., Medical Applications of Electroporation, *IEEE Transactions on Plasma Science*, 28(1):206-223 (Feb. 2000).
Dupuy D.E., et al., "Irreversible Electroporation in a Swine Lung Model," Cardiovascular and Interventional Radiology, 2011, vol. 34, No. 2, pp. 391-395.
Edd, et al., In Vivo Results of a New Focal Tissue Ablation Technique: Irreversible Electroporation, *IEEE Transactions on Biomedical Engineering*, 53(5):1409-1415 (Jun. 2006).
Eurostat Statistics Database: "Health at a Glance: Europe (2012 and 2014 Reports)," Dec 3, 2014, 41 Pages, Retrieved from URL: http://www.oecd-ilibrary.org/social-issues-migration-health/health-at-a-glance-europe-2012_978926418.
Extended EP Search Report dated Mar. 4, 2026 in EP Patent Appl. Serial No. 23797314.4 (123001).
Extended European Search Report for European Application No. 20840607.4, dated Jun. 27, 2023, 08 Pages.
Extended European Search Report for European Application No. 21853941.9, dated Jul. 23, 2024, 07 Pages.
Extended European Search Report for European Application No. 22210537.1, dated Apr. 26, 2023, 11 Pages.
Extended European Search Report for European Application No. 22820712.2, dated Apr. 7, 2025, 08 Pages.
Extended European Search Report for European Application No. 22821096.9, dated Aug. 6, 2025, 13 Pages.
Extended European Search Report for European Application No. 23174654.6, dated Jun. 23, 2023, 07 Pages.
Extended European Search Report for European Application No. 25184327.2, dated Jul. 15, 2025, 08 Pages.
Faststats-Chronic Lower Respiratory Disease: "Chronic Obstructive Pulmonary Disease (COPD) Includes: Chronic Bronchitis and Emphysema," Centers for Disease Control and Prevention (CDC)/National Center for Health Statistics (NCHS), Jan. 16, 2021, pp. 1-2, [Retrieved on Feb. 4, 2021] Retrieved from URL: https://www.cdcgov/nchs/fastats/copd.htm.
Fernandez-Bussy S., et al., "Histopathologic Results Post Bronchial Rheoplasty," American Thoracic Society, 2019, 17 Pages.
Garcia P.A., et al., "A Parametric Study Delineating Irreversible Electroporation from Thermal Damage Based on a Minimally Invasive Intracranial Procedure," BioMedical Engineering OnLine, Apr. 30, 2011, vol. 10, Article No. 34, 22 Pages, Retrieved from URL: http://www.biomedical-engineering-online.com/content/10/1/34.
Garcia P.A., et al., "An Experimental Investigation of Temperature Changes During Electroporation," URSI General Assembly and Scientific Symposium, Istanbul, Turkey, Aug. 13-20, 2011, 4 Pages.
Garcia P.A., et al., "Intracranial Nonthermal Irreversible Electroporation: In Vivo Analysis," The Journal of Membrane Biology, 2010, vol. 236, pp. 127-136.
Garcia P.A., et al., "Non-Thermal Irreversible Electroporation for Tissue Ablation," Chapter 3, Electroporation in Laboratory and Clinical Investigations, Editors: E. P. Spugnini and al Baldi, 2010, 22 Pages.
Global Strategy for the Diagnosis, Management, and Prevention of COPD: "Global Initiative for Chronic Obstructive Lung Disease," 2017, pp. 1-42.
Gowrishankar, et al., Electrical behavior and por accumulation in a multicellular model for conventional and supra-electroporation, Biochem. Biophys. Res. Commun., 349(2):643-653 (Oct. 2006).
Ibey, et al., Plasma Membrane Permeabilization by Trains of Ultrashort Electric Pulses, Bioelectrochemistry, 79(1):114-121 (Aug. 2010).
International Search Report & Written Opinion dated Aug. 29, 2025 in Int'l PCT Patent Appl. Serial No. PCT/US2025/028619 (181001).
International Search Report and Written Opinion for International Application No. PCT/US2017/039527, dated Dec. 7, 2017, 22 Pages.
International Search Report and Written Opinion for International Application No. PCT/US2018/067504, dated Mar. 13, 2019, 13 Pages.
International Search Report and Written Opinion for International Application No. PCT/US2020/042260, dated Oct. 14, 2020, 12 Pages.
International Search Report and Written Opinion for International Application No. PCT/US2021/030911, dated Aug. 16, 2021, 10 Pages.
International Search Report and Written Opinion for International Application No. PCT/US2021/044469, dated Nov. 8, 2021, 17 Pages.
International Search Report and Written Opinion for International Application No. PCT/US2022/032981, dated Aug. 29, 2022, 15 Pages.
International Search Report and Written Opinion for International Application No. PCT/US2023/020282, dated Jul. 21, 2023, 14 Pages.
International Search Report and Written Opinion for International Application No. PCT/US2023/022109, dated Aug. 15, 2023, 10 Pages.
International Search Report and Written Opinion for International Application No. PCT/US2023/060897, dated Jul. 7, 2023, 15 Pages.
International Search Report and Written Opinion for International Application No. PCT/US2024/020309, dated Jul. 29, 2024, 10 Pages.
International Search Report and Written Opinion for International Application No. PCT/US2024/043295, dated Oct. 30, 2024, 9 Pages.
Invitation to Pay Additional Fees for International Application No. PCT/US2023060897, dated May 15, 2023, 10 Pages.
Jourabchi, et al., Irreversible Electroporation (NanoKnife) in Cancer Treatment, *Gastrointestinal Intervention*, 3:8-18 (Feb. 2014).
Kim, et al., Technical Feasibility and Safety of Image-Guided Biphasic Monopolar Pulsed Electric Field Ablation of Metastatic and Primary Malignancies, J. Vasc. Interv. Radiol., 35:1644-1654 (2024).
Kim H.B., et al., "Physicochemical Factors That Affect Electroporation of Lung Cancer and Normal Cell Lines," Biochemical and Biophysical Research Communications, 2019, vol. 517, No. 4, pp. 703-708.
Kim V., et al., "The Chronic Bronchitic Phenotype of COPD: An Analysis of the COPD Gene Study," Chest, Sep. 2011, vol. 140, No. 3, pp. 626-633.
Krassowska, et al., Viability of Cancer Cells Exposed to Pulsed Electric Fields: The Role of Pulse Charge, *Annals of Biomedical Engineering*, 31:80-90 (2003).
Lee, et al., Advanced Hepatic Ablation Technique for Creating Complete Cell Death: Irreversible Electroporation,*Radiology*, 255(2) (Apr. 8, 2010).
Mercadal, et al., Avoiding nerve stimulation in irreversible electroporation: a numerical modeling study, *Phys. Med. Biol.*, 62(20):8060-8079 (Oct. 2004).
Miklavcic, et al., A validated model of in vitro electric field distribution in tissues for electrochemotherapy and for DNA electrotransfer for gene therapy, *Biochimica et Biophysica Acta*, 1523:73-83 (2000).
Miklavcic, et al., The effect of high frequency electric pulses on muscle contractions and antitumor efficiency in vivo for a potential use in clinical electrochemotherapy, *Bioelectrochemistry*, 65:121-128 (2005).
Miklovic T., et al., "A Comprehensive Characterization of Parameters Affecting High-frequency Irreversible Electroporation Lesions," Annals of Biomedical Engineering, 2017, vol. 45, pp. 2524-2534 (11 Pages).
Miller, et al., Cancer Cells Ablation with Irreversible Electroporation, *Technology in Cancer Research & Treatment*, 4(6):699-705 (Dec. 2005).
Moore, et al., Early experience with PEF in the setting of recalcitrant stage IV lung cancer, Lung Cancer, 204:08575 (May 2025).
Napotnik, et al., Cell death due to electroporation—A Review, *Bioelectrochemistry*, 141:107871, pp. 1-18 (2021).

(56) References Cited

OTHER PUBLICATIONS

Mir, et al., Mechanisms of electrochemotherapy, *Advanced Drug Delivery Reviews*, 35:107-118 (1999).
Neal II, R. E. et al., "The Feasibility of Irreversible Electroporation for the Treatment of Breast Cancer and Other Heterogeneous Systems," Annals of Biomedical Engineering, Dec. 2009, vol. 37, No. 12, pp. 2615-2625.
Neal II R.E., et al., "An "Off-the-Shelf" System for Intraprocedural Electrical Current Evaluation and Monitoring of Irreversible Electroporation Therapy," Cardio Vascular and Interventional Radiology, 2014, vol. 38, No. 3, pp. 736-741 (6 Pages).
Neal II R.E., et al., "Chapter 5.4: Clinical Implications of Irreversible Electroporation: Clinical and Preclinical Findings," Springer, Editors: H Akiyama and R Heller (In Press), 10 Pages.
Neal II R.E., et al., "Experimental Characterization and Numerical Modeling of Tissue Electrical Conductivity during Pulsed Electric Fields for Irreversible Electroporation Treatment Planning," IEEE Transactions on Biomedical Engineering, Apr. 2012, vol. 59, No. 4, pp. 1076-1085.
Neal II R.E., et al., "Hepatic Epithelioid Hemangioendothelioma Treated With Irreversible Electroporation and Antibiotics," Journal of Clinical Oncology, 2013, vol. 31, 5 Pages, Retrieved from URL: http://jco.ascopubs.org/cgl/dol/10.1200/JCO.2012.44.9736.
Neal II R.E., et al., "Improved Local and Systemic Anti-Tumor Efficacy for Irreversible Electroporation in Immunocompetent versus Immunodeficient Mice," Plos One, May 24, 2013, vol. 8, No. 5 (e64559), 10 Pages, DOI:10.1371/journal.pone.0064559.
Neal II R.E., et al., "In Vitro and Numerical Support for Combinatorial Irreversible Electroporation and Electrochemotherapy Glioma Treatment," Annals of Biomedical Engineering, 2013, vol. 42, 13 Pages, DOI: 10.1007/s10439-013-0923-2.
Neal II R.E., et al., "In vivo Characterization and Numerical Simulation of Prostate Properties for Non-Thermal Irreversible Electroporation Ablation," The Prostate, 2014, vol. 17, No. 10 (22760), 11 Pages.
Neal II R.E., et al., "In Vivo Irreversible Electroporation Kidney Ablation: Experimentally Correlated Numerical Models," IEEE Transactions on Biomedical Engineering, 2013, 10 Pages, DOI: 10.1109/TBME.2014.2360374.
Neal II R.E., et al., "Spectrum of Imaging and Characteristics for Liver Tumors Treated With Irreversible Electroporation," Journal of Biomedical Science and Engineering, 2012, vol. 5, pp. 813-818.
Neal II R.E., et al., "The Effects of Metallic Implants on Electroporation Therapies: Feasibility of Irreversible Electroporation for Brachytherapy Salvage," CardioVascular and Interventional Radiology, 2013, vol. 36, No. 6, pp. 1638-1645 (08 Pages).
Neal II R.E., et al., "Treatment of Breast Cancer through the Application of Irreversible Electroporation Using a Novel Minimally Invasive Single Needle Electrode," Breast Cancer Research and Treatment, Aug. 2010, vol. 123, No. 1, pp. 295-301 (13 Pages).
Neal II R.E., et al., "Successful Treatment of a Large Soft Tissue Sarcoma with Irreversible Electroporation," Journal of Clinical Oncology, May 1, 2011, vol. 29, No. 13, pp. e372-e377, DOI: 10.1200/JCO.2010.33.0902.
Novickij V., et al., "High Frequency Electroporation Efficiency is Under Control of Membrane Capacitive Charging and Voltage Potential Relaxation," Bioelectrochemistry, 2018, vol. 119, pp. 92-97.
O'brien T.J., et al., "Effects of Internal Electrode Cooling on Irreversible Electroporation Using a Perfused Organ Model," International Journal of Hyperthermia, 2019, vol. 35, No. 1, pp. 44-55 (12 Pages).
Reddy, et al., Pulsed Field Ablation for Pulmonary Vein Isolation in Atrial Fibrillation, Journal of the American College of Cardiology, 74(3):315-326 (Jul. 2019).
Ricke J., et al., "Irreversible Electroporation (IRE) Fails to Demonstrate Efficacy in a Prospective Multicenter Phase II Trial on Lung Malignancies: The ALICE Trial," Cardiovascular and Interventional Radiology, 2015, vol. 38, No. 2, pp. 401-408.
Rogers, et al., Strength-Duration Curve for an Electrically Excitable Tissue Extended Down to Near 1 Nanosecond, *IEEE Transactions on Plasma Science*, 32(4):1587-1599 (Aug. 2004).
Rossmeisl J.H., Jr., et al., "Safety and Feasibility of the Nanoknife System for Irreversible Electroporation Ablative Treatment of Canine Spontaneous Intracranial Gliomas," Journal of Neurosurgery, Jul. 3, 2015, vol. 123, No. 4, pp. 1008-1025 (18 Pages).
Rubinsky, et al., Optimal Parameters for the Destruction of Prostate Cancer Using Irreversible Electroporation, *The Journal of Urology*, 180:2668-2674 (Dec. 2008).
Sano M.B., et al., "Burst and Continuous High Frequency Irreversible Electroporation Protocols Evaluated in a 3D Tumor Model," Physics in Medicine and Biology, Jul. 6, 2018, vol. 63, No. 13 (135022), pp. 1-18.
Sano M.B., et al., "Towards the Creation of Decellularized Organ Constructs Using Irreversible Electroporation and Active Mechanical Perfusion," BioMedical Engineering OnLine, 2010, vol. 9, No. 83, 16 Pages, Retrieved from URL: http://www.biomedical-engineering-online.com/content/9/1/83.
Scheffer H.J., et al., "The Influence of a Metal Stent on the Distribution of Thermal Energy during Irreversible Electroporation," Plos One, Feb. 4, 2016, vol. 11, No. 2 (e0148457), 13 Pages, DOI:10.1371/journal.pone.0148457.
Schoenbach, et al., Bioelectric Effects of Intense Nanosecond Pulses, IEEE Transactions on Dielectrics & Electrical Insulation, 14(5):1088-1109 (2007).
Schoenbach K.H., et al., "Bioelectrics," Springer, Editors: H. Akiyama, R. Heller, 2017, 491 Pages, ISBN 978-4-431-56093-7, ISBN 978-4-431-56095-1 (eBook), DOI: 10.1007/978-4-431-56095-1.
Shah P.L., et al., "Epithelial Resurfacing: The Bronchial Skin Peel," American Journal of Respiratory and Critical Care Medicine, Sep. 1, 2020, Vo,. 202, No. 5, pp. 641-642.
Tang P.S., et al., "Acute Lung Injury and Cell Death: How Many Ways Can Cells Die," American Journal of Physiology Lung Cellular and Molecular Physiology, Jan. 18, 2008, vol. 294, No. 4, pp. L632-L641.
Thomson K.R., et al., "Introduction to Irreversible Electroporation-Principles and Techniques," Techniques in Vascular and Interventional Radiology, 2015, vol. 18, No. 3, pp. 128-134.
Tri J.A., et al., "Electroporation Ablation of Bronchial Smooth Muscle Cells: A Novel Non-thermal Asthma Therapy," Pulmonary and Critical Care Medicine, 2016, vol. 1, No. 4, pp. 1-4.
Valipour A., et al., "First-in-Human Results of Bronchial Rheoplasty: An endobronchial Treatment for Chronic Bronchitis (CB)," American Thoracic Society, 2019, pp. 1-20.
Vollmer, Robin T., Tumor Length in Prostate Cancer, *American Journal of Clinical Pathology*, 130(1):77-82 (Jul. 2008).
Wandel A., et al., "Optimizing Irreversible Electroporation Ablation with a Bipolar Electrode," The Journal of Vascular and Interventional Radiology, Sep. 2016, vol. 27, No. 9, pp. 1441-1450 (12 Pages).
Weaver, et al., Theory of electroporation: A Review, Bioelectrochemistry and Bioenergetics, 41(2):135-160 (Dec. 1996).
Wendler, et al., A prospective Phase 2a pilot study investigating focal percutaneous irreversible electroporation (IRE) ablation by NanoKnife in patients with localised renal cell carcinoma (RCC) with delayed interval tumour resection (IRENE trial), Contemporary Clinical Trials, 43:10-19 (May 2015).
Xuzhang, et al., Cisplatin-induced Pyroptosis Enhances the Efficacy of PD-L1 Inhibitor in Small-Cell Lung Cancer via GSDME/IL12/CD4Tem Axis, International Journal of Biological Sciences, 20(2):537-553 (2024).

* cited by examiner

| Parameter | Relative Change | Treatment Size | Muscle Contraction | Temperature Rise | Treatment Delivery Time | Electrical Arcing Risk |
|---|---|---|---|---|---|---|
| Electrode Style | Monopolar | ↓ | ↑ | ↓ | = | ↓ |
| Voltage | ↑ | ↑ | ↑ | ↑ | = | ↑ |
| Waveform | Biphasic | ↓ | ↓ | = | = | ↓ |
| Fundamental Frequency | ↑ | ↓ | ↓ | = | = | = |
| Packet Duration | ↑ | ↑ | ↑ | ↑ | = | ↑ |
| Number of Packets | ↑ | ↑ | = | ↑ | ↑ | = |
| Packet Delivery Rate | ↑ | = | = | ↑ | ↓ | = |

FIG. 5

PEF

RFA

H&E staining of tumor samples collected 4 days post treatment confirm matched ablation volumes

| Cytokines Modulated by PEF | PEF-driven Biological response |
|---|---|
| IL-17A | ↓ Angiogenesis<br>↓ Inflammation |
| CSF2, CSF3, CCL2 | ↓ Accumulation of MDSCs |
| CSF1, IL13, IL4 | ↓ Proliferation of TAMs |
| IL6 | ↓ Proliferation |
| TNF, CSF2, IL10 | ↓ TREM1 |

| Slide # | Stain | Main cell reactivity | Expected cellular location | Color | |
|---|---|---|---|---|---|
| 1 | HE-1 | | | H&E |  |
| 2 | CD3<br>FoxP3 | T cells<br>Tregs | Membrane<br>nuclear | Red<br>brown |  |
| 3 | PD-L1<br>(22c3) | | Membrane | Brown |  |
| 4 | CD4<br>CD8α | T helper<br>T cytotoxic | Membrane<br>membrane | Red<br>brown |  |
| 5 | PanCK<br>CD20 | Epithelial<br>B cells | Cytoplasmic<br>membrane | Red<br>brown |  |
| 6 | HE-2 | | | H&E |  |

| | PEF (n=27[1]) | Control (n=6[1]) |
|---|---|---|
| Median Age at Consent ± SD (range) | 66 ± 6 (53-78) | 68 ± 8 (55-79) |
| Sex (%) | | |
| Male | 21(78) | 3(50) |
| Female | 6(22) | 3(50) |
| Tumor Location (%) | | |
| Right Lung | 17(63) | 5(83) |
| Left Lung | 10(37) | 1(17) |
| Average Tumor Size[2] ± SD, cm | 2.6 ± 1.0 (n=22) | 2.1 ± 0.8 (n=4) |
| PEF-delivery/Biopsy[3] Approach (%) | | |
| Percutaneous | 8(30) | 0 |
| Endoluminal | 19(70) | 4(67)[4] |
| Average days between PEF/Biopsy[5] and surgery ± SD (range) | 21 ± 5 (14-42) | 43 ± 13 (28-62)[4] |
| Histology (%) | | |
| Adenocarcinoma | 15(56) | 2(33) |
| Squamous cell carcinoma | 4(15) | 1(17) |
| Other[6] | 2(7) | 0(0) |
| Not provided yet | 6(22) | 3(50) |

Pink = Non-PEF control, Purple = mucinous ACA
Blue = PEF treated tumors with matching Pre-Tx biopsy
* = Location of CDZ

CONTROLLED LESION AND IMMUNE RESPONSE TO PULSED ELECTRIC FIELD THERAPY

CROSS-REFERENCE TO RELATED APPLICATIONS

This application claims priority to and the benefit of U.S. Patent Application No. 63/480,468, filed Jan. 18, 2023, and U.S. Patent Application No. 63/488,304, filed Mar. 3, 2023; this application is also a continuation in part of PCT/US2022/044021, filed Sep. 19, 2022 which claims priority to and benefit of U.S. Patent Application No. 63/246,239 filed Sep. 20, 2021, U.S. Patent Application No. 63/290,529 filed Dec. 16, 2021, U.S. Patent Application No. 63/322,319 filed Mar. 22, 2022, and U.S. Patent Application No. 63/351,562 filed Jun. 13, 2022, the disclosures of each of which are fully incorporated herein by reference.

BACKGROUND

Abnormal tissue can take a variety of different forms, such as damaged, diseased, obstructive, cancerous or undesired tissue. In some instances, the abnormal tissue is a tumor, such as a benign tumor or a malignant tumor, a cyst, or an area of diseased tissue. One of the most troublesome types of abnormal tissue is related to cancer.

Cancer is a group of diseases characterized by the uncontrolled growth and spread of abnormal cells. If the spread is not controlled, it can result in death. Although the causes of cancer are not completely understood, numerous factors are known to increase the disease's occurrence, including many that are modifiable (e.g., tobacco use and excess body weight) and others that are not (e.g., inherited genetic mutations). These risk factors may act, simultaneously or in sequence, to initiate and/or promote cancer growth. Cancer is the second most common cause of death in the US, exceeded only by heart disease.

Lung, liver and pancreatic cancers are among the cancers having the lowest survival rates. Lung cancer is the leading cause of cancer death, more than colorectal, breast, and prostate combined. The overall change in 5-yr survival rate for all stages combined has only slightly improved over time: 1970's (approx. 13%), 2010's (approx. 17.2%), 2019 (approx. 21.7%). Liver cancer incidence rates have more than tripled since 1980, while the death rates have more than doubled during this time. Some progress has occurred in survival for patients with liver cancer, but 5-year survival remains low, even for those diagnosed at the localized stage. Pancreatic cancer is expected to be the 2nd leading cause of cancer-related death in 2020. The 5-yr survival rate for all stages is 9% and has not substantially improved over 40 years. These outcomes have endured despite the evolution of conventional therapies.

Many types of cancers are not successfully cured or recur at a later point in time. Recurrence typically occurs because the original treatment did not successfully eliminate all of the cancer cells and those left behind proliferated. In some instances, the cancer cells spread to other parts of the body in undetectable amounts, known as micrometastases. When these micrometastases are not overcome by the body, they grow to detectable levels and require additional treatment. And, ultimately, many patients lose their battle with cancer.

Consequently, improved therapies are needed that more successfully treat cancers and reduce or prevent their recurrence, along with improved therapies for all types of abnormal tissue. At least some of these objectives will be met by the present invention.

SUMMARY

Described herein are embodiments of apparatuses, systems and methods for treating target tissue, particularly cardiac tissue. Likewise, the invention relates to the following numbered clauses:

1. A system for treating tissue within a body of a patient comprising:
   - an instrument having at least one energy delivery body, wherein the at least one energy delivery body is configured to be positioned so as to direct pulsed electric field energy to the tissue creating a lesion; and
   - a generator in electrical communication with the at least one energy delivery body, wherein the generator includes at least one energy delivery algorithm configured to provide the pulsed electric field energy in a manner that creates a plurality of zones within the lesion which elicits an increase in an adaptive immune response of the patient.
2. A system as in clause 1, wherein the plurality of zones has a bulls-eye arrangement.
3. A system as in any of the above clauses, wherein the plurality of zones includes at least a pulsed electric field zone.
4. A system as in any of the above clauses, wherein the plurality of zones includes an immune response zone.
5. A system as in any of the above clauses, wherein the plurality of zones includes a thermal zone.
6. A system as in any of the above clauses, wherein the plurality of zones includes an inflammatory zone.
7. A system as in clause 1, wherein the plurality of zones includes at least a pulsed electric field zone and a thermal zone.
8. A system as in clause 7, wherein the pulsed electric field zone and the thermal zone together cover an area within the lesion and wherein the thermal zone does not exceed 50% of the area.
9. A system as in clause 8, wherein the thermal zone does not exceed 25% of the area.
10. A system as in clause 9, wherein the thermal zone is 10-20% of the area.
11. A system as in any of clauses 7-10, wherein the at least one energy delivery algorithm includes inter-cycle delays in a waveform of the pulsed electric field energy, wherein the inter-cycle delays are configured to control the size of the thermal zone.
12. A system as in clause 11, wherein the inter-cycle delays are at least 10 microseconds.
13. A system as in clause 12, wherein the inter-cycle delays are 10 microseconds to 1000 microseconds.
14. A system as in any of clauses 11-13, wherein the inter-cycle delays are configured to minimize or eliminate a cavitation zone.
15. A system as in any of clauses 11-14, wherein the inter-cycle delays are 1000 microseconds.
16. A system as in clause 11, wherein the at least one energy delivery algorithm includes inter-packet delays in a waveform of the pulsed electric field energy, wherein the inter-packet delays are configured to control the size of the thermal zone.
17. A system as in clause 16, wherein the inter-packet delays are 3-5 seconds.

18. A system as in any of the above clauses, wherein the lesion is created by a single dose within 5-6 minutes.

19. A system as in any of the above clauses, wherein the adaptive immune response comprises an increase in a ratio of CD8+/CD4+ T-cells.

20. A system as in any of the above clauses, wherein the adaptive immune response comprises an increase in PD-L1 expression.

21. A system as in any of the above clauses, wherein the adaptive immune response comprises an upregulation of lymphoid pathways.

22. A system as in any of the above clauses, wherein the adaptive immune response comprises a generation of tumor antigen release.

23. A system as in any of the above clauses, wherein the adaptive immune response comprises a downregulation of regulatory T-cells.

24. A system as in any of the above clauses, wherein the adaptive immune response comprises a generation or increase in generation of Tertiary Lymphoid Structures within the tissue.

25. A system as in any of the above clauses, wherein the at least one energy delivery algorithm creates a synergistic effect when the pulsed electric field energy is combined with an immune checkpoint inhibitor.

26. A system as in clause 25, wherein the immune checkpoint inhibitor comprises anti-PD1 therapy.

27. A system as in any of clauses 25-26, wherein the synergistic effect increases an abscopal effect.

28. A system as in any of clauses 25-27, wherein the synergistic effect increases PD-L1 expression.

29. A system as in any of clauses 25-28, wherein the tissue comprises a tumor that is unresponsive or waning responsiveness to anti-PD1 therapy so as to cause the tumor to be responsive to anti-PD1 therapy.

30. A system as in any of the above clauses, wherein the at least one energy delivery algorithm generates a waveform of the pulsed electric field energy having a voltage of 3000V.

31. A system as in any of the above clauses, wherein the at least one energy delivery algorithm generates a waveform of the pulsed electric field energy having a fundamental frequency of 400 kHz.

32. A system as in any of the above clauses, wherein the at least one energy delivery algorithm generates a waveform of the pulsed electric field energy having packets of biphasic pulse cycles.

33. A system as in clause 32, wherein each packet has 40 biphasic pulse cycles.

34. A system as in any of clauses 32-33, wherein an inter-cycle delay of 1000 microseconds is disposed between each biphasic pulse cycle within a packet.

35. A system as in any of clauses 32-34, wherein the waveform comprises 100 packets in a single dose.

36. A system as in any of clauses 32-35, wherein an inter-packet delay of 3 seconds is disposed between each packet of the dose.

37. A system as in any of the above clauses, wherein the at least one energy delivery algorithm generates a waveform of the pulsed electric field energy having packets wherein each packet has a 100 microsecond active time.

38. A system as in clause 37, wherein each packet has 40 cycles.

39. A system as in any of clauses 37-38, wherein the waveform has a voltage of 3000V.

40. A system for treating a target tissue within a body of a patient comprising:

an instrument having at least one energy delivery body, wherein the at least one energy delivery body is configured to be positioned so as to direct pulsed electric field energy to the target tissue; and a generator in electrical communication with the at least one energy delivery body, wherein the generator includes at least one energy delivery algorithm configured to provide the pulsed electric field energy so as to create a lesion in the target tissue, wherein the at least one energy delivery algorithm generates a waveform of the pulsed electric field energy having a parameter combination configured to cause a synergistic effect when combined with an immune checkpoint inhibitor.

41. A system as in clause 40, wherein the synergistic effect increases an abscopal effect.

42. A system as in clause 40, wherein the immune checkpoint inhibitor comprises anti-PD1.

43. A system as in clause 42, wherein the synergistic effect increases PD-L1 expression.

44. A system as in any of clauses 40-43, wherein the tissue comprises a tumor that is unresponsive or waning responsiveness to anti-PD1 therapy so as to cause the tumor to be responsive to anti-PD1 therapy.

45. A system as in any of clauses 40-44, wherein the at least one energy delivery algorithm generates a waveform of the pulsed electric field energy having a voltage of 3000V.

46. A system as in any of clauses 40-45, wherein the at least one energy delivery algorithm generates a waveform of the pulsed electric field energy having a fundamental frequency of 400 kHz.

47. A system as in any of clauses 40-46, wherein the at least one energy delivery algorithm generates a waveform of the pulsed electric field energy having packets of biphasic pulse cycles.

48. A system as in clause 47, wherein each packet has 40 biphasic pulse cycles.

49. A system as in any of clauses 47-48, wherein an inter-cycle delay of 1000 microseconds is disposed between each biphasic pulse cycle within a packet.

50. A system as in any of clauses 47-49, wherein the waveform comprises 100 packets in a single dose.

51. A system as in any of clauses 47-50, wherein an inter-packet delay of 3 seconds is disposed between each packet of the dose.

52. A system as in any of clauses 47-51, wherein the at least one energy delivery algorithm generates a waveform of the pulsed electric field energy having packets wherein each packet has a 100 microsecond active time.

53. A system for treating a tumor within a body of a patient that is unresponsive or waning responsiveness to therapy comprising:

an instrument having at least one energy delivery body, wherein the at least one energy delivery body is configured to be positioned so as to direct pulsed electric field energy to the tumor; and a generator in electrical communication with the at least one energy delivery body, wherein the generator includes at least one energy delivery algorithm that generates a waveform of the pulsed electric field energy having a parameter combination configured to cause the tumor to be responsive to therapy.

54. A system as in clause 53, wherein the therapy comprises immune checkpoint inhibitor therapy.

55. A system as in clause 54, wherein the immune checkpoint inhibitor therapy comprises anti-PD1 therapy.

56. A system for treating tissue within a body of a patient comprising:

an instrument comprising a shaft having a proximal end and a distal end, and at least one energy delivery body disposed near the distal end of the shaft, wherein the distal end of the shaft is configured to deliver pulsed electric field energy to the tissue creating a lesion, wherein the pulsed electric field energy maintains an extracellular matrix within a least a portion of the lesion; and a generator in electrical communication with the at least one energy delivery body, wherein the generator includes at least one energy delivery algorithm configured to provide the pulsed electric field energy in a manner that reduces or eliminates a cavitation zone within the lesion.

57. A system as in clause 56, wherein the at least one energy delivery algorithm includes inter-cycle delays in a waveform of the pulsed electric field energy, wherein the inter-cycle delays are configured to reduce or eliminate the cavitation zone.

58. A system as in clause 57, wherein the inter-cycle delays are at least 10 microseconds.

59. A system as in clause 58, wherein the inter-cycle delays are 10 microseconds to 1000 microseconds.

60. A system as in clause 59, wherein the inter-cycle delays are 1000 microseconds.

61. A system for treating tissue within a body of a patient comprising:

an instrument comprising a shaft having a proximal end and a distal end, and at least one energy delivery body disposed near the distal end of the shaft, wherein the distal end of the shaft is configured to deliver pulsed electric field energy to the tissue creating a lesion, wherein the pulsed electric field energy maintains an extracellular matrix within a least a portion of the lesion; and a generator in electrical communication with the at least one energy delivery body, wherein the generator includes at least one energy delivery algorithm configured to provide the pulsed electric field energy in a manner that creates at least a thermal zone and a pulsed electric field zone within the lesion.

62. A system for treating a target tissue within a body of a patient comprising:

an instrument having at least one energy delivery body, wherein the at least one energy delivery body is configured to be positioned so as to direct pulsed electric field energy to the target tissue; and a generator in electrical communication with the at least one energy delivery body, wherein the generator includes at least one energy delivery algorithm configured to provide the pulsed electric field energy so as to create a lesion in the target tissue, wherein the at least one energy delivery algorithm generates a waveform of the pulsed electric field energy having a parameter combination configured to cause generation or increased generation of tertiary lymphoid structures within the target tissue.

63. A system as in clause 62, wherein the includes at least one energy delivery algorithm configured to provide the pulsed electric field energy in a manner that creates a plurality of zones within the lesion which elicits an increase in an adaptive immune response of the patient.

64. A system as in clause 63, wherein the plurality of zones includes at least a pulsed electric field zone.

65. A system as in any of clauses 63-64, wherein the plurality of zones includes an immune response zone.

66. A system as in any of clauses 63-65, wherein the plurality of zones includes a thermal zone.

67. A system as in any of clauses 63-66, wherein the plurality of zones is devoid of a cavitation zone.

68. A system as in any of clauses 63-67, wherein the plurality of zones includes an inflammatory zone.

69. A system for treating a mass of undesired tissue cells within a body of a patient comprising:

an instrument comprising a shaft having a proximal end and a distal end, and at least one energy delivery body disposed near the distal end of the shaft, wherein the distal end of the shaft is configured deliver non-thermal energy to the mass of undesired tissue cells; and a generator in electrical communication with the at least one energy delivery body, wherein the generator includes at least one energy delivery algorithm configured to provide an electric signal of the non-thermal energy deliverable to the mass of undesired tissue so as to destroy at least a portion of the mass of undesired tissue.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 provides a table illustrating various example effects of parameter changes.

DETAILED DESCRIPTION OF THE INVENTION

Figures 1A, 1B:
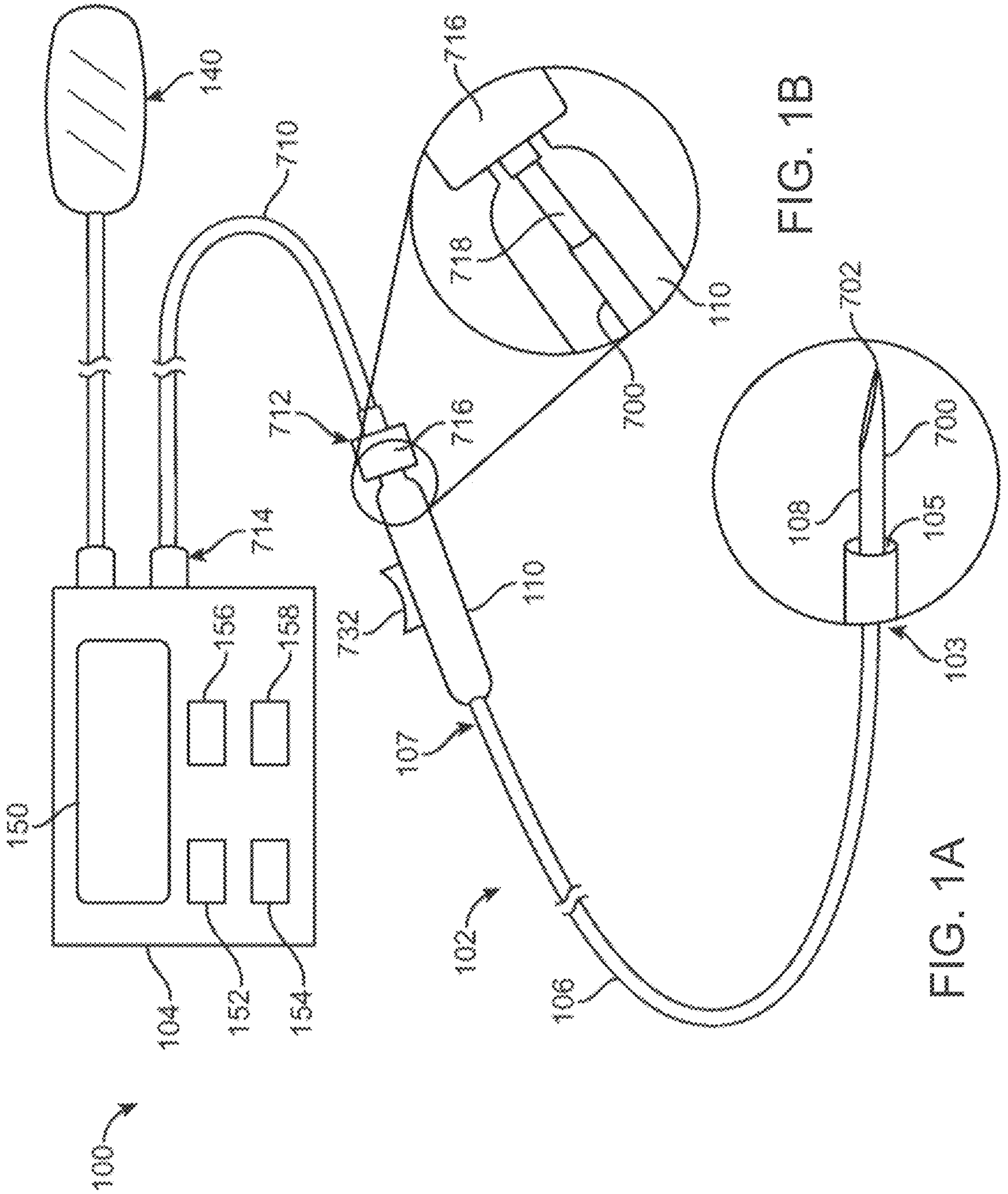
FIGS. 1A-1B provide an overview illustration of an example therapeutic system for use in delivering specialized PEF energy.

Specific embodiments of the disclosed devices, systems, and methods will now be described with reference to the drawings. Nothing in this detailed description is intended to imply that any particular component, feature, or step is essential to the invention.

I. Overview

Devices, systems and methods are provided to treat damaged, diseased, abnormal, obstructive, cancerous or undesired tissue (e.g. a tumor, a benign tumor, a malignant tumor, a cyst, or an area of diseased tissue, etc.) by delivering specialized pulsed electric field (PEF) energy to target tissue areas in a specific dose so as to obtain a superior outcome. The PEF energy and delivery has been optimized to provide advanced treatment of target tissue areas, including destruction of undesired tissue and generation of improved inflammatory and immune responses. These various types of treatment are controlled by a variety of factors including the electrode geometry, the dose of PEF energy delivered, the time the energy is delivered over, and the waveform of the PEF energy itself. The PEF energy is delivered in the form a dose which is considered to be one application of the specialized energy. Each dose creates a lesion in the target tissue area. In some embodiments, the desired outcome is achieved with the delivery of a single dose. This achievement reduces treatment time and reduces any complications which may arise by providing additional doses, such as related to repositioning of the energy delivery device or retreatment of the same tissue area. The specific parameter values which define the waveform of the energy cause the waveform to be configured to deliver the desired effects with one dose. It may be appreciated that additional doses may be delivered to the target tissue if desired or the energy may be delivered to additional target tissues that may or may not include the original target tissue.

Conventional PEF energy delivery systems have been focused simply on destruction of tissue. When treating cancer with PEF energy, complete destruction of the tumor is desired. Consequently, generating a lesion covering the size of the tumor has been desired wherein the lesion destroys the cells of the tumor. This technology has remained relatively unsophisticated and as such has yet to truly deliver on its promise. Specifically, while the energy itself is conceptualized as 'non-thermal' several studies have been troubled by thermal sequelae as a consequence of a variety of different factors. These studies have shown that while a higher delivered electrical energy can be associated with larger treatment zones, it also causes an increase in cavitation, pale tissue intracellular changes, and white-to-tan tissue extracellular coagulation due to Joule heating effects. Conventional PEF can also cause cavitation by partial electrical discharge (i.e. arcing). Arcing can occur due to several factors, one of which is higher delivered electrical energy. These effects limit any potential benefit to the immune system while increasing the likelihood of complications as a consequence the thermal injury. Thus, there is a lack in formalized understanding with regard to how conventional PEF energy might be deployed so as to maximize the electric field effects while managing the potential thermal and cavitary effects that might be associated with treatment.

In contrast, the devices, systems and methods described herein utilize a specific dose of specialized PEF energy to generate lesions having various zones, wherein manipulation of the zones provides benefits which culminate in a more comprehensive and therefore successful treatment of the patient, particularly when treating cancer and other diseases. Typically, the zones are manipulated to eliminate or reduce a cavitation zone, eliminate or reduce a thermal zone and maximize a PEF zone along with a potential inflammatory zone and immune response zone. The size or amount of the zones are particularly generated so that their combination elicits an increase in the adaptive immune response of the patient, such as by promoting a cascade of increased recruitment for Tregs, CD4, CD8, and other adaptive immune cell types. These lesion classifications (i.e. zones) can be measured grossly, but also monitored in real-time based on the tissue properties (i.e. tissue density, impedance change, etc.) and perhaps most importantly, via imaging modalities such as CT, etc.

II. Example Delivery Systems

The specialized PEF energy is delivered with the use of systems and devices advantageously designed for superior access to target tissue throughout the body, particularly in locations previously considered inaccessible to percutaneous approaches. Such access is typically minimally invasive and relies on endoluminal approaches, though it may be appreciated that other approaches, such as percutaneous, laparoscopic or open surgical approaches, may be used in some situations, if desired. FIG. 1 provides an overview illustration of an example therapeutic system 100 for use in delivering the specialized PEF energy. In this embodiment, the system 100 comprises an elongate instrument 102 comprising a shaft 106 having a distal end 103 and a proximal end 107. The instrument 102 includes an energy delivery body 108 near the distal end 103 of the shaft 106. It may be appreciated that the energy delivery body 108 may take a variety of forms. The energy delivery body 108 may be mounted on or integral with an exterior of the shaft 106 so as to be externally visible. Or, the energy delivery body 108 may be housed internally within the shaft 106 and exposed by advancing from the shaft 106 or retracting the shaft 106 itself. Likewise, more than one energy delivery body 108 may be present and may be external, internal or both. In some embodiments, the shaft 106 is comprised of a polymer, such as an extruded polymer. It may be appreciated that in some embodiments, the shaft 106 is comprised of multiple layers of material with different durometers to control flexibility and/or stiffness. In some embodiments, the shaft 106 is reinforced with various elements such as individual wires or wire braiding. In either case, such wires may be flat wires or round wires. Wire braiding has a braid pattern and in some embodiments the braid pattern is tailored for desired flexibility and/or stiffness. In other embodiments, the wire braiding that reinforces the shaft 106 may be combined advantageously with multiple layers of material with different durometers to provide additional control of flexibility and/or stiffness along the length of the shaft.

In any case, each energy delivery body 108 comprises at least one electrode for delivery of the PEF energy. Typically, the energy delivery body 108 comprises a single delivery electrode and operates in a monopolar arrangement which is achieved by supplying energy between the energy delivery body 108 disposed near the distal end 103 of the instrument 102 and a return electrode 140 positioned upon the skin of the patient. It will be appreciated, however, that bipolar energy delivery and other arrangements may alternatively be used. When using bipolar energy delivery, the instrument 102 may include a plurality of energy delivery bodies 108 configured to function in a bipolar manner or may include a single energy delivery body 108 having multiple electrodes configured to function in a bipolar manner. The instrument 102 typically includes a handle 110 disposed near the proximal end 107. The handle 110 is used to maneuver the instrument 102, and typically includes an actuator 732 for manipulating the energy delivery body 108. In some embodiments, the energy delivery body 108 transitions from a closed or retracted position (during access) to an open or exposed position (for energy delivery) which is controlled by the actuator 732. Thus, the actuator 732 typically has the form of a knob, button, lever, slide or other mechanism. It may be appreciated that in some embodiments, the handle 110 includes a port for introduction of liquids, agents, substances, tools or other devices for delivery through the instrument 102. Example liquids include suspensions, mixtures, chemicals, fluids, chemotherapy agents, immunotherapy agents, micelles, liposomes, embolics, nanoparticles, drug-eluting particles, genes, plasmids, and proteins, to name a few.

The instrument 102 is in electrical communication with a generator 104 which is configured to generate the PEF energy. In this embodiment, the generator 104 includes a user interface 150, one or more energy delivery algorithms 152, a processor 154, a data storage/retrieval unit 156 (such as a memory and/or database), and an energy-storage subsystem 158 which generates and stores the energy to be delivered. In some embodiments, the user interface 150 on the generator 104 is used to select the desired treatment algorithm 152. In other embodiments, the algorithm 152 is automatically selected by the generator 104 based upon information obtained by one or more sensors. A variety of energy delivery algorithms may be used. In some embodiments, one or more capacitors are used for energy storage/delivery, however any other suitable energy storage element may be used. In addition, one or more communication ports are typically included.

The distal end 103 of the instrument 102 is typically advanceable through a delivery device, such as an endoscope. Endoscopes typically comprise a control body attached to an elongate insertion tube having a distal tip. The endoscope has an interior lumen accessible by a port into which the distal end 103 of the instrument 102 passes. The shaft 106 of the instrument 102 advanceable through the interior lumen and exits out of the distal tip of the endoscope. Imaging is achieved through the endoscope with the use of a light guide tube having an endoscopic connector which connects to a light and energy source. The distal tip of the endoscope may be outfitted with visualization technologies including but not limited to video, ultrasound, laser scanning, etc. These visualization technologies collect signals consistent with their design and transmit the signal either through the length of the shaft over wires or wirelessly to a video processing unit. The video processing unit then processes the video signals and displays the output on a screen. It may be appreciated that the endoscope is typically specific to the anatomical location to which it is being used, such as gastroscopes (upper GI endoscopy, which includes the stomach, esophagus, and small intestine (duodenum)), colonoscopes (large intestine), bronchoscopes (lungs), laryngoscopes (larynx), cystoscopes (urinary tract), duodenoscopes (small intestine), enteroscopes (digestive system), ureteroscopes (ureter), hysteroscopes (cervix, uterus), etc. It may be appreciated that in other embodiments, the instrument 102 is deliverable through a catheter, sheath, introducer, needle or other delivery system.

Endoluminal access allows treatment of target tissue from within various lumens in the body. Lumens are the spaces inside of tubular-shaped or hollow structures within the body and include passageways, canals, ducts and cavities to name a few. Example luminal structures include blood vessels, esophagus, stomach, small and large intestines, colon, bladder, urethra, urinary collecting ducts, uterus, vagina, fallopian tubes, ureters, kidneys, renal tubules, spinal canal, spinal cord, and others throughout the body, as well as structures within and including such organs as the lung, heart and kidneys, to name a few. In some embodiments, the target tissue is accessed via the nearby luminal structure. In some instances, a treatment instrument 102 is advanced through various luminal structures or branches of a luminal system to reach the target tissue location. For example, when accessing a target tissue site via a blood vessel, the treatment instrument 102 may be inserted remotely and advanced through various branches of the vasculature to reach the target site. Likewise, if the luminal structure originates in a natural orifice, such as the nose, mouth, urethra or rectum, entry may occur through the natural orifice and the treatment instrument 102 is then advanced through the branches of the luminal system to reach the target tissue location. Alternatively, a luminal structure may be entered near the target tissue via cut-down or other methods. This may be the case when accessing luminal structures that are not part of a large system or that are difficult to access otherwise.

Once a target tissue area has been approached endoluminally, energy can be delivered to the target tissue in a variety of ways. In one arrangement, an energy delivery body 108 is positioned within a body lumen and energy is delivered to the target tissue that is has entered the body lumen, through at least a portion of the lumen wall to target tissue either within the lumen wall and/or at least partially surrounding the lumen wall or through the lumen wall to target tissue outside and nearby the lumen wall. In another arrangement, the energy delivery body 108 is advanced through the lumen wall and inserted within or near target tissue outside of the lumen wall. It may be appreciated that such arrangements may be combined, involving at least two energy delivery bodies 108, one positioned within the body lumen and one extending through the wall of the body lumen. In some embodiments, each of the energy delivery bodies 108 function in a monopolar manner (e.g. utilizing a return electrode placed at a distance). In other embodiments, at least some of the energy delivery bodies 108 function in a bipolar manner. Since the lumen itself is preserved throughout the treatment, these delivery options are possible and allow treatment of tissue in, on or nearby the lumen itself. Such delivery of therapy allows access to previously inaccessible tissue, such as tumors or diseased tissue that has invaded lumen walls or has wrapped at least partially around a body lumen, too close to be surgically removed or treated with conventional focal therapies. Many conventional focal therapies, such as treatment with thermal energy, damage or destroy the structure of the lumen walls due to thermal protein coagulation, etc. In particular, bowel injuries caused by radiofrequency ablation are one of the most feared complications and have been associated with mortality due to sepsis and abscess formation. Consequently, most physicians will defer radiofrequency ablation in tumors adjacent to bowel. Other conventional focal therapies are ineffective near particular body lumens. For example, cryotherapy relies on sufficient cooling of tissue which is compromised by flow through body lumens, such a blood through the vasculature, which reduces the cooling effects. Such endoluminal access is also less invasive than other types of treatment, such as percutaneous delivery of energy involving the placement of numerous needle probes through the skin and deeply into tissues and organs. Since natural openings in the body are utilized, less wound healing is incurred along with reduced possible points of infection. Likewise, locations deep within the body can be access along with locations that are difficult to otherwise access from the outside, such as locations behind other organs or near great vessels, etc. It may be appreciated that a variety of anatomical locations may be treated with the systems and methods described herein. Examples include luminal structures themselves, soft tissues throughout the body located near luminal structures and solid organs accessible from luminal structures, including but not limited to liver, pancreas, gall bladder, kidney, prostate, ovary, lymph nodes and lymphatic drainage ducts, underlying musculature, bony tissue, brain, eyes, thyroid, etc. It may also be appreciated that a variety of tissue locations can be accessed percutaneously.

The endoscopic approach also lends itself to monopolar energy delivery. As mentioned, monopolar delivery involves the passage of current from the energy delivery body 108 (near the distal end of the instrument 102) to the target tissue and through the patient to a return pad 140 positioned against the skin of the patient to complete the electric current circuit. Thus, in some embodiments, the instrument 102 includes only one energy delivery body 108 or electrode. This allows the instrument 102 to have a low profile so as to be positionable within smaller body lumens. This also allows deep penetration of tissue surrounding the energy delivery body 108. Likewise, when penetrating the lumen wall with such devices, only one penetration is needed per treatment due to the use of only one energy delivery body 108. It may be appreciated that additional penetrations may occur due to various device designs or treatment protocols, however in some embodiments, the monopolar delivery design reduces the invasiveness of the procedure, simplifies the device and treatment design and provides superior treatment zones in target tissue.

The devices, systems and methods described herein may be used on their own or in combination with other treatments. Such combinatory treatment may be applicable to cancer treatment in particular. For example, the PEF treatment described herein may be used in combination with a variety of non-surgical therapies, neoadjuvant and adjuvant therapies such as radiotherapy, chemotherapy, targeted therapy/immunotherapy, focal therapy, gene therapy, plasmid therapy, to name a few. Example focal therapies include microwave ablation, radiofrequency ablation, cryoablation, high intensity focused ultrasound (HIFU), and other pulsed electric field ablation therapies. Such combination may condition the tissue for improved responsiveness and in some cases a synergistic response that is greater than either of the therapies alone. In addition, the PEF treatments described herein may lead to an abscopal effect due to the nature of the therapy.

FIGS. 1A-1B, illustrate a therapeutic system 100 comprising an energy delivery catheter 102 connectable with a generator 104. As shown, the catheter 102 comprises a shaft 106 having a distal end 103, a proximal end 107 and at least one lumen 105 extending at least partially therethrough. Likewise, the catheter 102 also includes at least one energy delivery body 108. In this embodiment, an energy delivery body 108 has the form of a probe 700 that is disposed within the lumen 105 of the shaft 106. The probe 700 has a probe tip 702 that is advanceable through the lumen 105 and extendable from the distal end 103 of the shaft 106 (expanded in FIG. 1A to show detail). In this embodiment, the tip 702 has a pointed shape configured to penetrate tissue, such as to resemble a needle. Thus, in this embodiment, the probe tip 702 is utilized to penetrate the lumen wall W and surrounding tissue so that it may be inserted into the target tissue external to the body lumen. Thus, the probe 700 has sufficient flexibility to be endoluminally delivered yet has sufficient column strength to penetrate the lumen wall W and target tissue. In some embodiments, the catheter 102 has markings to indicate to the user the distance that the probe tip 702 has been advanced so as to ensure desired placement.

In some embodiments, the probe extends from the distal end 103 of the shaft 106 approximately less than 0.5 cm, 0.5 cm, 1 cm, 2 cm, 3 cm, 4 cm, 5 cm, 6 cm, 7 cm, 8 cm or more than 8 cm. In some embodiments, the probe extends 1-3 cm or 2-3 cm from the distal end of the shaft 106. In some embodiments, the probe is 18 gauge, 19 gauge, 20 gauge, 21 gauge, 22 gauge, 23 gauge, 24 gauge, or 25 gauge. In some embodiments, the probe 700 is comprised of a conductive material so as to serve as an electrode. Thus, the electrode would have the size of the exposed probe. Example materials include stainless steel, nitinol, cobalt-chromium alloy, copper, and gold. In some embodiments, the exposed probe conductive material is coated with a different material, with examples including platinum-iridium, gold, platinum black, palladium, or other materials. The conductive material, or the conductive material coating may be designed so as to reduce the biological interactions of the tissue, reduce the production of electrochemical effects from the PEF treatment, or more efficiently distribute the PEF energy into the tissue, among other purposes. The materials may be smooth, electropolished, sandblasted at various grits, or treated with other mechanical or chemical preparations to alter the roughness of the surface, which may be done to reduce biological interactions of the tissue, facilitate easier deployment and retraction of the electrode, reduce he production of electrochemical effects from the PEF treatment, or more efficiently distribute the PEF energy into the tissue, among other purposes. Thus, in these embodiments, the PEF energy is transmittable through the probe 700 to the probe tip 702. Consequently, the shaft 106 is comprised of an insulating material or is covered by an insulating sheath. Example insulating materials include polyimide, silicone, polytetrafluoroethylene, and polyether block amide. The insulating material may be consistent or varied along the length of the shaft 106 or sheath. Likewise, in either case, the insulating material typically comprises complete electrical insulation. However, in some embodiments, the insulating material allows for some leakage current to penetrate.

When the probe 700 is energized, the insulting shaft 106 protects the surrounding tissue from the treatment energy and directs the energy to the probe tip 702 (and any exposed portion of the probe 700) which is able to deliver treatment energy to surrounding tissue. Thus, the tip 702 acts as a delivery electrode and its size can be selected based on the amount of exposed probe 700. Larger electrodes can be formed by exposing a greater amount of the probe 700 and smaller electrodes can be formed by exposing less. In some embodiments, the exposed tip 702 (measured from its distal end to the distal edge of the insulating shaft) during energy delivery has a length of 0.1 cm, 0.2 cm, 0.3 cm, 0.4 cm, 0.5 cm, 0.6 cm, 0.7 cm, 0.8 cm, 0.9 cm, 1 cm, 2 cm, 3 cm, greater than 3 cm, up to 8 cm, less than or equal to 0.1 cm, less than or equal to 0.3 cm, less than or equal to 0.5 cm, less than or equal to 1 cm, 0.2-0.3 cm, 0.1-0.5 cm, 0.1-1 cm, and all ranges and subranges therebetween. In addition to changing the size of the electrode, the tip 702 is retractable into the shaft 106 to allow for atraumatic endoscopic delivery and is then advanceable as desired to reach the target tissue. In this embodiment, advancement and retraction are controlled by an actuator 732 (e.g. knob, button, lever, slide or other mechanism) on a handle 110 attached to the proximal end 107 of the shaft 106. It may be appreciated that the shaft 106 itself may be advanced toward the target tissue, with or without advancing the probe from the distal end 103 of the shaft 106. In some embodiments, the distal end of the shaft 106 is advanced up to 20 cm into the tissue, such as from an external surface of a luminal structure or from an external surface of the body of the patient.

The handle 110 is connected to the generator 104 with the use of a specialized energy plug 510. The energy plug 510 has a first end 512 that connects to the handle 110 and a second end 514 the connects to the generator 104. The connection of the first end 512 with the handle 110 is expanded for detail in FIG. 1B. In this embodiment, the first end 712 has an adapter 716 that includes a connection wire 718 extending therefrom. The connection wire 718 is insertable into the proximal end of the probe 700 within the handle 110. This allows the energy to be transferred from the generator 104, through the connection wire 718 to the probe 700. Thus, the probe 700 is able to be electrified throughout its length, however only the exposed tip 702 delivers energy to the tissue due to the presence of the insulated shaft 106.

In this embodiment, the generator 104 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, however any other suitable energy storage element may be used. In addition, one or more communication ports are included.

In some embodiments, the generator 104 includes three sub-systems: 1) a high-energy storage system, 2) a high-voltage, medium-frequency switching amplifier, and 3) the system controller, firmware, and user interface. The system controller includes a cardiac synchronization trigger monitor that allows for synchronizing the pulsed energy output to the patient's cardiac rhythm. The generator takes in alternating current (AC) mains to power multiple direct current (DC) power supplies. The generator's controller can cause the DC power supplies to charge a high-energy capacitor storage bank before energy delivery is initiated. At the initiation of therapeutic energy delivery, the generator's controller, high-energy storage banks and a bi-phasic pulse amplifier can operate simultaneously to create a high-voltage, medium frequency output.

It will be appreciated that a multitude of generator electrical architectures may be employed to execute the energy delivery algorithms. In particular, in some embodiments, advanced switching systems are used which are capable of directing the pulsed electric field circuit to the energy delivering electrodes separately from the same energy storage and high voltage delivery system. Further, generators employed in advanced energy delivery algorithms employing rapidly varying pulse parameters (e.g., voltage, frequency, etc.) or multiple energy delivery electrodes may utilize modular energy storage and/or high voltage systems, facilitating highly customizable waveform and geographical pulse delivery paradigms. It should further be appreciated that the electrical architecture described herein above is for example only, and systems delivering pulsed electric fields may or may not include additional switching amplifier components.

The user interface 150 can include a touch screen and/or more traditional buttons to allow for the operator to enter patient data, select a treatment algorithm (e.g., energy delivery algorithm 152), initiate energy delivery, view records stored on the storage/retrieval unit 156, and/or otherwise communicate with the generator 104. The user interface 150 can include a voice-activated mechanism to enter patient data or may be able to communicate with additional equipment in the suite so that control of the generator 104 is through a secondary separate user interface.

In some embodiments, the user interface 150 is configured to receive operator-defined inputs. The operator-defined inputs can include a duration of energy delivery, one or more other timing aspects of the energy delivery pulse, power, and/or mode of operation, or a combination thereof. Example modes of operation can include (but are not limited to): system initiation and self-test, operator input, algorithm selection, pre-treatment system status and feedback, energy delivery, post energy delivery display or feedback, treatment data review and/or download, software update, or any combination or subcombination thereof.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104. The cardiac monitor 170 can be used to continuously acquire an ECG signal. External electrodes 172 may be applied to the patient P to acquire the ECG. The generator 104 analyzes one or more cardiac cycles and identifies the beginning of a time period during which it is safe to apply energy to the patient P, thus providing the ability to synchronize energy delivery with the cardiac cycle. In some embodiments, this time period is within milliseconds of the R wave (of the ECG QRS complex) to avoid induction of an arrhythmia, which could occur if the energy pulse is delivered on a T wave. It will be appreciated that such cardiac synchronization is typically utilized when using monopolar energy delivery, however it may be utilized as part of other energy delivery methods.

In some embodiments, the processor 154, among other activities, modifies and/or switches between the energy-delivery algorithms, monitors the energy delivery and any sensor data, and reacts to monitored data via a feedback loop. In some embodiments, the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data, such as related to the treatments delivered, and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. The processor 154 can be, for example, a general-purpose processor, a field programmable gate array (FPGA), an application specific integrated circuit (ASIC), a digital signal processor (DSP), and/or the like. The processor 154 can be configured to run and/or execute application processes and/or other modules, processes and/or functions associated with the system 100, and/or a network associated with the system 100. As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a FPGA, an ASIC, a DSP) and/or software-based module (e.g., a module of computer code stored in memory and/or executed at the processor) capable of performing one or more specific functions associated with that module.

Each of these algorithms 152 may be executed by the processor 154. In some embodiments, the instrument 102 includes one or more sensors 160 that can be used to determine temperature, impedance, resistance, capacitance, conductivity, pH, optical properties (coherence, echogenicity, fluorescence), electrical or light permittivity, and/or conductance, to name a few. In some embodiments, one or more of the electrodes act as the one or more sensors. In other embodiments, the one or more sensors are separate from the electrodes. It may be appreciated that one or more sensors 160 may be disposed in a variety of locations, particularly depending on the parameter being sensed. For example, a sensor may be located along an energy delivery body 108, along an interior of the instrument, along the shaft 106, along an element that protrudes from the instrument 120, etc. Multiple sensors 160 may be present for sensing the same parameter at multiple sites, sensing different parameters at different sites, or sampling parameters at different sites to compile a single metric value measurement (e.g. average temperature, average voltage exposure, average conductivity, etc.). One or more sensors 160 may alternatively or additionally be located on a separate device. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It will be appreciated that the system 100 can include an automated treatment delivery algorithm that could dynamically respond and adjust and/or terminate treatment in response to inputs such as temperature, impedance at various voltages or AC frequencies, treatment duration or other timing aspects of the energy delivery pulse, treatment power and/or system status.

In some embodiments, imaging is achieved with the use of a commercially available system, such as an endoscope connected with a separate imaging screen. It will be appreciated that imaging modalities can be incorporated into the instrument 102 or used alongside or in conjunction with the instrument 102. The imaging modality can be mechanically, operatively, and/or communicatively coupled to the instrument 102 using any suitable mechanism.

III. Intra-Luminal Placement and Energy Delivery

As mentioned previously, in one arrangement, an energy delivery body 108 is positioned within a body lumen and energy is delivered to or through the lumen wall to target tissue either within the lumen, within the lumen wall, at least partially surrounding the lumen wall or outside the lumen wall. Thus, the target tissue is able to be treated from an energy delivery body 108 positioned within a body lumen.

In some embodiments, the treatment devices and systems are configured for luminal access and delivery of therapeutic energy toward the luminal walls so as to treat the nearby target tissue. The therapeutic energy is generally characterized by high voltage pulses which allow for removal of target tissue with little or no destruction of critical anatomy, such as tissue-level architectural proteins among extracellular matrices. This prevents dangerous collateral effects, such as stenosis, thrombus formation or fistulization, to name a few, and also allows for regeneration of healthy new luminal tissue within days of the procedure. Examples of systems which provide this type of therapeutic treatment include the pulmonary tissue modification systems (e.g., energy delivery catheter systems) described in commonly assigned patent applications including international patent application number PCT/US2017/039527 titled "GENERATOR AND A CATHETER WITH AN ELECTRODE AND A METHOD FOR TREATING A LUNG PASSAGEWAY," which claims priority to U.S. provisional application Nos.

62/355,164 and 62/489,753, international patent application number PCT/US2018/067501 titled "METHODS, APPARATUSES, AND SYSTEMS FOR THE TREATMENT OF DISORDERS" which claims priority to U.S. Provisional Application No. 62/610,430, and international patent application number PCT/US2018/067504 titled "OPTIMIZATION OF ENERGY DELIVERY FOR VARIOUS APPLICATIONS" which claims priority to Provisional Patent Application No. 62/610,430 filed Dec. 26, 2017 and U.S. Provisional Patent Application No. 62/693,622 filed Jul. 3, 2018, all of which are incorporated herein by reference for all purposes.

As mentioned previously, one or more energy delivery algorithms 152 are programmable, or can be pre-programmed, into the generator 104 for delivery to the patient. The one or more energy delivery algorithms 152 specify electric signals which provide energy delivered to the lumen walls which are non-thermal (e.g. below a threshold for thermal ablation; below a threshold for inducing coagulative thermal damage), reducing or avoiding inflammation, and/or preventing denaturation of stromal proteins in the luminal structures. In general, the algorithm 152 is tailored to affect tissue to a pre-determined depth and/or to target specific types of cellular responses to the energy delivered. It may be appreciated that depth and/or targeting may be affected by parameters of the energy signal prescribed by the one or more energy delivery algorithms 152, the design of the instrument 102 (particularly the one or more energy delivery bodies 108), and/or the choice of monopolar or bipolar energy delivery. Typically, depths of up to 0.01 cm, up to 0.02 cm, 0.01-0.02 cm, up to 0.03 cm, 0.03-0.05 cm, up to 0.05 cm, up to 0.08 cm, up to 0.09 cm, up to 0.1 cm, up to 0.2 cm, up to 0.5 cm, up to 0.7 cm, up to 1.0 cm, up to 1.5 cm, up to 2.0 cm, up to 2.5 cm, up to 3.0 cm, up to 3.5 cm, up to 4.0 cm, up to 4.5 cm, or up to 5.0 cm, to name a few. These depths may be larger for circumferentially focal targets, or they may exist for entire circumferential depths through the lumen and parenchymal tissue.

Thus, the treatment is minimally invasive, quickly and easily executable, and has relatively low sensitivity to electrode placement (e.g. due to the monopolar arrangement) therefore allowing technicians of various skill levels to achieve high levels of consistency as well as successful outcomes. In some embodiments, the monopolar arrangement is possible without the need for muscular paralytics due to the waveform characteristics of the energy used. This can mitigate muscle contractions from motor neuron and skeletal muscle depolarization to an acceptable level, with or without a neuromuscular paralytic. Thus, it becomes possible to implement monopolar-directed treatment delivery through a lumen out to a distant pad, producing a more predictable and desirable treatment zone. It may be appreciated that paralytics may optionally be used depending on the type of energy and the depth of penetration desired.

IV. Extra-Luminal Placement and Energy Delivery

Figure 2B:
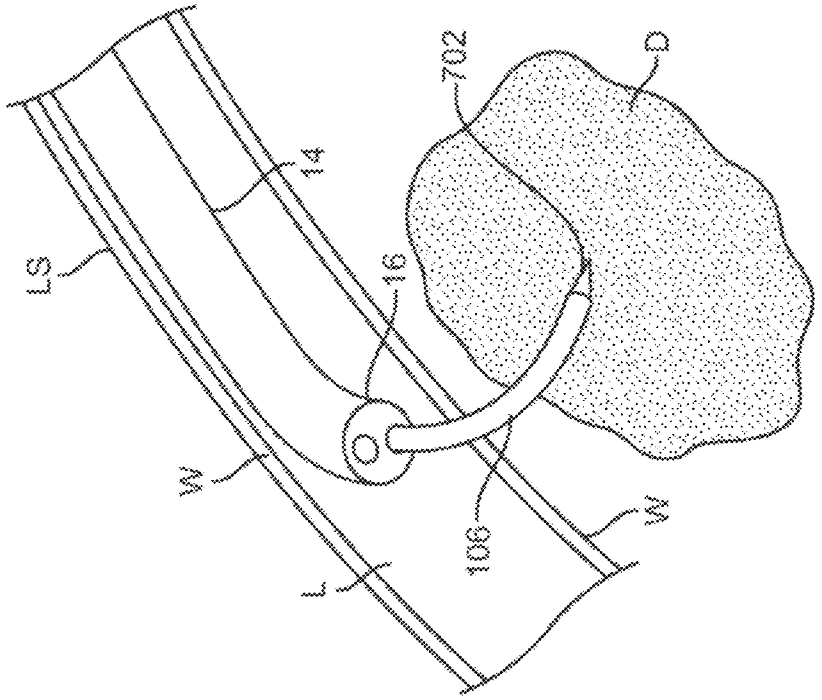
FIGS. 2A-2C illustrate an example method of treatment.
Figure 2A:
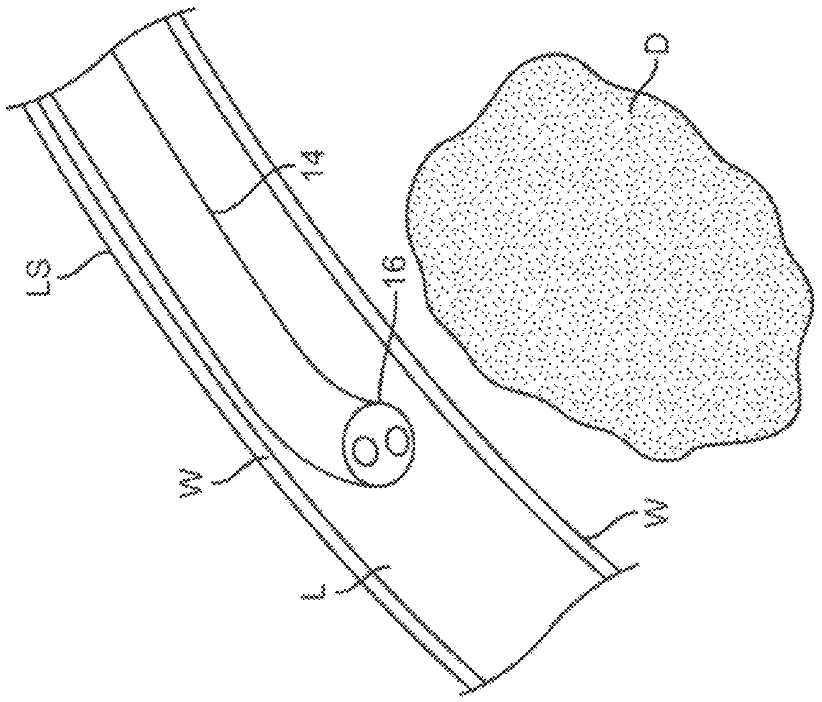
Figure 2C:
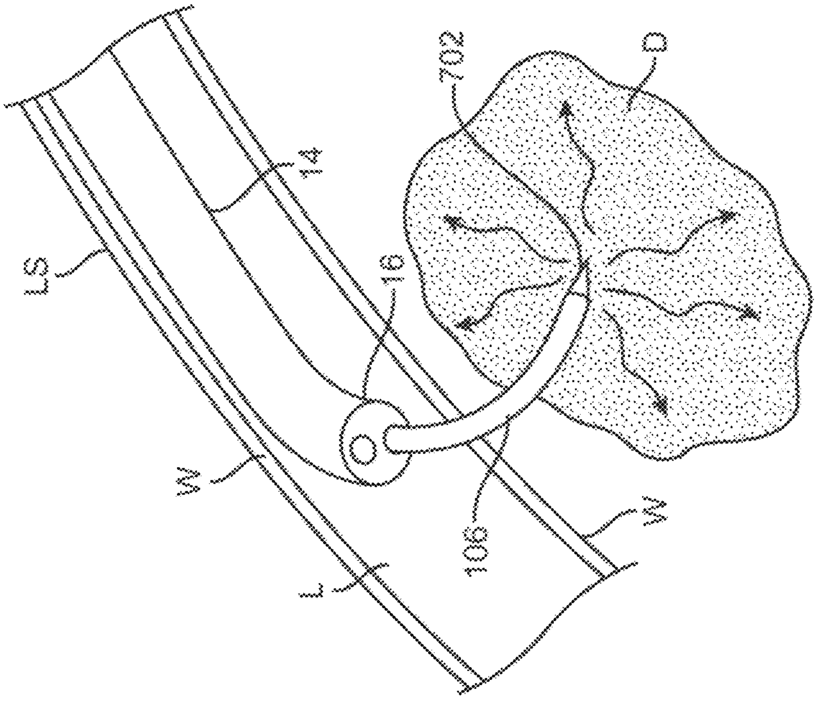

FIGS. 2A-2C illustrate an example method of treatment. FIG. 2A illustrates abnormal or diseased tissue D, such as a tumor, near a luminal structure LS. In this example, the diseased tissue D is near the luminal structure LS but spaced a distance from the lumen wall W. This luminal structure LS is used to access and the diseased tissue D and extra-luminally treat the diseased tissue D near the luminal structure LS. In this embodiment, the elongate insertion tube 14 of an endoscope 10 is advanced into the luminal structure LS and its distal tip 16 is steered toward the lumen wall W, beyond which lies the diseased tissue D. Once desirably positioned, the treatment catheter 102 is advanced through a lumen in the insertion tube 14 so that the distal end 103 of the shaft 106 extends beyond the tip 16 of the endoscope 10, as illustrated in FIG. 2B. In this embodiment, the probe tip 702 assists in penetrating the wall W and the shaft 106 is advanced across the wall W until the probe tip 702 is desirably positioned within the diseased tissue D. Referring to FIG. 2C, in this embodiment, the probe tip 702 is then advanced from the shaft 106 so as to create a desired delivery electrode size. Energy is then delivered according to one or more energy delivery algorithms 152, through the probe 700 to the diseased tissue D, as illustrated in FIG. 2C by wavy arrows extending radially outwardly from the probe tip 702. It may be appreciated that the distance into the diseased tissue may vary based on parameter values, treatment times and type of tissue, to name a few. It may also be appreciated that larger or smaller treatment depths may be achieved than illustrated herein.

The delivered energy treats the diseased tissue D as appropriate. In the case of cancer, the cancerous cells are destroyed, eliminated, killed, removed, etc. Examples include immunogenic cell death (e.g., necroptosis, pyroptosis, etc.) and programmed cell death (apoptosis), to name a few. In the PEF zone, such cell death occurs while maintaining non-cancerous, non-cellular elements, such as collagen, elastin, and matrix proteins. These non-cellular elements maintain the structure of the tissue allowing for and encouraging normative cellular regeneration. Likewise, any energy reaching the walls W of the nearby luminal structure LS preserve the integrity and mechanical properties of the luminal structure LS. It may be appreciated that in some instances, the energy kills the cells in the diseased tissue D directly, such as via accumulated generalized cellular injury and irrecoverable disruption of cellular homeostasis. In other instances, the cells die by action of the immune system or other biological processes. In some instances, remaining diseased tissue is surgically removed or removed by other methods.

A. Alternative Probe Designs

It may be appreciated that the probe 500 may have a variety of forms and structures. In some embodiments, the probe 500 is hollow, such as having a tubular shape. In such embodiments, the probe 500 may be formed from a hypotube or metal tube. Such tubes can be optimized for desired push and torque capabilities, kink performance, compression resistance and flexibility to ensure consistent and reliable steerability to the target treatment site. Likewise, such tubes can include custom engineered transitions, such as laser cutting and skive features, along with optional coatings to optimize produce performance. In some embodiments, the tube has a sharp point with multiple cutting edges to form the probe tip 502. In other embodiments, the tube has a blunt atraumatic tip. In some embodiments, the probe 500 is solid, such as having a rod shape. These probes can also be optimized and customized similarly to hypotubes. In some embodiments, the solid probe 500 has a sharp point with a symmetric or asymmetric cut to form the probe tip 502. In other embodiments, the solid probe 502 has a blunt atraumatic tip.

It may be appreciated that the probe 500 may include a lumen for delivery of fluids or agents. Such a lumen may be internal or external to the probe. Likewise, fluid or agents may be delivered directly from the shaft 106, such as through a lumen therein or a port located along the shaft 106.

In some embodiments, the probe 500 is comprised of multiple probe elements, wherein each probe element has similar features and functionality to an individual probe 500 as described above. Thus, in some embodiments they may be considered separate probes, however for simplicity they will be described as probe elements making up a single probe 500 since they are passed through the same shaft 106 of the instrument 102. It may be appreciated that any number of probe elements may be present, including one, two, three, four, five, six, seven, eight, nine, ten or more. Likewise, the probe elements may be extended the same or different distances from the shaft 106 and may have the same or different curvatures. In another embodiment, the probe elements to not have any curvature and exit from the shaft 106 in a linear fashion. Typically, the probe elements are pre-curved so that advancement of the probe tip from the shaft 106 allows the probe element to assume its pre-curved shape. Thus, in some embodiments, a variety of curvatures can be utilized by advancing the probe tips differing amounts from the shaft 106.

It may be appreciated that the size of the probe tip 502 capable of transmitting energy may be further adjusted with the use of an insulating sheath 552 that extends at least partially over the probe. As mentioned previously, the size of the active portion of the probe tip 502 may be adjusted based on its extension from the shaft 106. However, this may be further refined, particularly when a plurality of probe elements are present, with the use of insulating sheaths 552 covering portions of the individual probe elements.

It may be appreciated that any of the probe elements described herein may have the same structure and features as any of the probes describe herein. For example, the probe elements may be constructed of the same materials, have the same functionality and have a sharp or atraumatic tip. Likewise, it may be appreciated that any of the probe elements may be deployed independently or simultaneously and may be energized independently or simultaneously. The energy delivered may be provided by the same energy delivery algorithm 152 or different energy delivery algorithms 152, therefore delivering the same or different energies. Any of the probe elements may function in a monopolar manner or in a bipolar manner between pairs of probe elements. Likewise, it may be appreciated that the probe elements may function in a combination of monopolar and bipolar manners.

As stated previously, in many of these extra-luminal delivery embodiments, the energy delivery body 108 has the form of a probe 500 that is disposed within the lumen 105 of the shaft 106. In some embodiments, the probe 500 comprises a plurality of wires or ribbons 120 and forms a basket 555 serving as an electrode. It may be appreciated that alternatively the basket 555 can be laser cut from a tube. It may be appreciated that a variety of other designs may be used. Typically, the basket 555 is delivered to a targeted area in a collapsed configuration and then expanded for use.

V. Imaging

Methods associated with imaging that can be useful include: (a) detecting diseased target tissue, (b) identifying areas to be treated, (c) assessing areas treated to determine how effective the energy delivery was, (d) assessing target areas to determine if areas were missed or insufficiently treated, (e) using pre- or intra-procedural imaging to measure a target treatment depth and using that depth to choose a specific energy delivery algorithm to achieve tissue effects to that depth, (f) using pre or intra-procedural imaging to identify a target cell type or cellular interface and using that location or depth to choose a specific energy delivery algorithm to achieve tissue effects to that target cell type or cellular interface, and/or (g) using pre-, intra-, or post-procedural imaging to identify the presence or absence of a pathogen with or without the presence of inflamed tissue.

In some embodiments, confocal laser endomicroscopy (CLE), optical coherence tomography (OCT), ultrasound, static or dynamic CT imaging, X-ray, magnetic resonance imaging (MRI), and/or other imaging modalities can be used, either as a separate apparatus/system, or incorporated/integrated (functionally and/or structurally) into the treatment system 100 by either incorporating into the instrument 102 or a separate device. The imaging modality (or modalities) can be used to locate and/or access various sections of target tissue. In some embodiments, the targeted depth of treatment can be measured and used to select a treatment algorithm 152 sufficient to treat to the targeted depth. At least one energy delivery body can then be deployed at the target tissue site and energy delivered to affect the target tissue. The imaging modality (or modalities) can be used before, during, between, and/or after treatments to determine where treatments have or have not been delivered or whether the energy adequately affected the airway wall. If it is determined that an area was missed or that an area was not adequately affected, the energy delivery can be repeated followed by imaging modality (or modalities) until adequate treatment is achieved. Further, the imaging information can be utilized to determine if specific cell types and or a desired depth of therapy was applied. This can allow for customization of the energy delivery algorithm for treating a wide variety of patient anatomies.

In some embodiments, access via a body lumen is visualized with one or more appliances inserted into the body. Likewise, in some embodiments, one or more of a variety of imaging modalities (e.g., CLE, OCT) are used either along with direct visualization, or instead of direct visualization. As an example, a bronchoscope can be delivered via the mouth to allow for direct visualization and delivery of the instrument 102, while an alternate imaging modality can be delivered via another working channel of the bronchoscope, via the nose, or adjacent to the bronchoscope via the mouth. In some embodiments, the imaging modality (e.g., direct visualization, CLE, and/or OCT) is incorporated into the instrument 102 with appropriate mechanisms to connect the imaging modality to either the system generator 104 or commercially available consoles.

VI. Conditioning

It may be appreciated that although the PEF ablation treatments provided by the systems 100 may be used as conditioning for other treatments, the target tissue cells may alternatively be conditioned prior to the PEF ablation treatments provided by the systems 100.

In some embodiments, cells targeted for treatment are conditioned so as to modify the behavior of the cells in response to the delivery of the energy signals. Such conditioning may occur prior to, during, or after delivery of the energy signals. In some embodiments, conditioning prior to energy delivery is considered pre-conditioning and conditioning after energy delivery is considered post-conditioning. Such differentiation is simply based on timing rather than on how the conditioning treatment affects the cells. In other embodiments, pre-conditioning relates to affecting what happens to the cells during energy delivery, such as how the cells uptake the energy, and post-conditioning relates to affecting what happens to the cells after energy delivery, such as how the cells behave after receiving the energy. Such differentiation may be less relevant to timing since in some instances conditioning may occur prior to energy delivery but only affect the cellular response following the energy delivery. Therefore, it may be appreciated that "conditioning" may be considered to apply to each of these situations unless otherwise noted.

Typically, conditioning is achieved by delivering a conditioning solution. In the case of intra-luminal therapy, the conditioning solution may be delivered via the luminal structure. The conditioning solution may alternatively or additionally be delivered via direct fluid injection of the conditioning solution into the targeted region, either from an endoluminal or other approach. In some embodiments, the conditioning solution selectively alters the electrical properties of the target cells, such as to affect the way the pulsed energy delivery gets distributed. In other embodiments, the conditioning solution influences the activity of the target cells. For example, in the lung such conditioning solution may promote basal cell differentiation into ciliated cells and/or downregulate goblet cells and submucosal gland cells. In other embodiments, the conditioning solution increases the likelihood of the target cells to expire following pulsed energy delivery. In still other embodiments, the conditioning solution alters the responses of non-targeted cells to the pulsed electric fields. In alternate embodiments, conditioning is performed via non-solution-based exposure of the tissues. This includes radiation therapy, radiotherapy, proton beam therapy, etc. In some embodiments, the conditioning will impact the enzymatic and energy-producing components of the cellular infrastructure.

The conditioning solution may be comprised of a variety of agents, such as drugs, genetic material, bioactive compounds, and antimicrobials, to name a few. For embodiments where the conditioning solution increases the likelihood of the target cells to expire following pulsed energy delivery, the conditioning solution may comprise chemotherapy drugs (e.g. cisplatin, doxorubicin, paclitaxel, bleomycin, carboplatin, etc), calcium, antibiotics, or toxins, to name a few. For embodiments where the conditioning solution alters the responses from non-targeted cells to the pulsed electric fields, the conditioning solution may comprise cytokines (e.g. immunostimulants, such as interleukins), genes, VEGF (e.g. to encourage more vessel growth into area), cellular differentiating factors (e.g. molecules to promote conversion of goblet cells into ciliated cells), and/or other small molecules that interact with cells, such as agonists and antagonists for receptors such as programmed death (PD-1) or programmed death ligand (PD-L1). Conditioning solutions may be delivered at the targeted site to directly interact at the site of PEF energy delivery. They may also be delivered systemically (e.g., intravenously, intraperitoneally) or regionally (e.g., intravenously to feeding arterial supplies for the targeted region, higher feeding airway generations, intraparenchymally to tissue around the tissue directly affected by the PEF treatment).

In some embodiments, the conditioning solution includes cells, such as stem cells, autograft cells, allograft cells or other cell types. In these embodiments, the cells may be used to alter the tissue response to the pulsed electric fields. In other embodiments, the cells may be used to repopulate the affected area with healthy or desirable cells. For example, once target cells have been weakened or killed by the delivered pulsed energy treatment, the cells from the conditioning solution may move into the vacancies, such as a decellularized extracellular matrix. In some embodiments, the area is washed out to remove the dead cells, such as with a mild detergent, surfactant or other solution, prior to delivery of the conditioning solution containing the new cells. In other embodiments, mechanical stimulation, such as suction, debriding, or ultrasonic hydrodissection, is used to physically remove the dead cells prior to delivery of the conditioning solution containing the new cells.

In some embodiments, the conditioning provided may invoke a targeted immune response. The immune response may result in a number of factors that alter the treatment effect outcome. This may result in an increase in the systemic immunity upregulation using specific markers associated with some targeted tissue, such as a tumor or bacteria or virus associated with an infection. It may also result in an upregulation of the innate immunity that broadly affects the immune system functionality to detect general abnormal cells, bacteria, or other infectious organisms residing within the body, which may occur locally, regionally, or systemically.

In some embodiments, the conditioning solution is warmed or chilled to alter how the target cells respond. Generally, warmed solutions promote increased treatment effects (e.g. increased susceptibility to cell death), while chilled solutions would reduce the extent of treatment effect or increase cell survival after exposure to a reversibly-designed protocol. In some embodiments, a chilled conditioning solution comprised of genes and or drugs is used to precondition cells to survive energy delivery treatment, increasing the number of cells that survive the treatment. In some embodiments, the effects of the warmed/chilled conditioning solution is compounded with the general effects caused by the other agents in the solution (e.g. warmed calcium solution, chilled gene containing solution). In other embodiments, the warmed/chilled conditioning solution does not provide effects other than temperature changes. In such embodiments, the conditioning solution is typically comprised of isotonic saline, phosphate buffered solution or other benign solution.

It may be appreciated that such heating or cooling may alternatively be achieved by other methods that do not involve delivery of a conditioning solution. For example, the target tissue may be heated or cooled by contacting the tissue with a warmed/cooled device, deliberately warming/cooling the pulsed electric field delivery catheter, delivering mild cryotherapy, or delivering mild radiofrequency or microwave energy. As previously described, this could promote enhanced lethality or permeability effects to the tissue or it could provide protective aspects to the cells that enable them to survive the procedure and exude the desired change as was targeted for them as a result of the therapy.

In some embodiments, a conditioning solution is delivered systemically, such as by intravenous injection, ingestion or other systemic methods. In other embodiments, the conditioning solution is delivered locally in the area of the targeted cells, such as through a delivery device or the instrument 102 itself.

VII. Energy Delivery Algorithms and Lesion Optimization

The specialized energy is provided by one or more energy delivery algorithms 152. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, the fundamental frequency of the pulse sequence, duration of the individual pulses or sequence of pulses comprising a packet (which may change within the packet itself) to name a few. Additional parameters may include switch time between polarities in biphasic pulses, dead time or inter-cycle delay between biphasic cycles, and rest time or inter-packet delay between packets, which will be described in more detail in later sections. In some embodiments, there is a fixed inter-packet delay between packets. In some embodiments, packets are gated to the cardiac cycle and are thus variable with the patient's heart rate or are fixed so as to and synchronized with the cardiac cycle. In some embodiments, there is a deliberate, varying inter-packet delay algorithm or no rest period may also be applied between packets. Packet delivery may also be coordinated with multiple factors, such as a minimum inter-packet delay after which a next trigger signal (e.g., cardiac synchronization signal) is used to coordinate the timing of the subsequent packet delivery. It may be appreciated that a feedback loop based on sensor information and an auto-shutoff specification, and/or the like, may be included.

The specialized energy delivered to the target tissue by a probe 702 or other energy delivery body creates a lesion that has a plurality of zones. The zones emanate from the probe 702 radially outwardly, such as in rings. Each zone has differing cellular effects and therefore differing effects on the overall outcome of the treatment. In some instances, the zones include a cavitation zone, a thermal zone, a PEF zone, an inflammatory zone and an immune response zone.

Figure 3A:
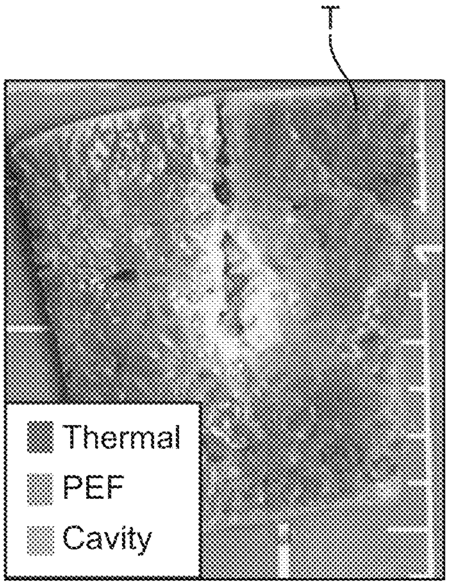
FIGS. 3A-3B illustrate tissue lesions resulting from a study focusing on the effects of the addition of inter-cycle and inter-packet delays within the energy waveform on the local tissue characteristics.
Figure 3B:
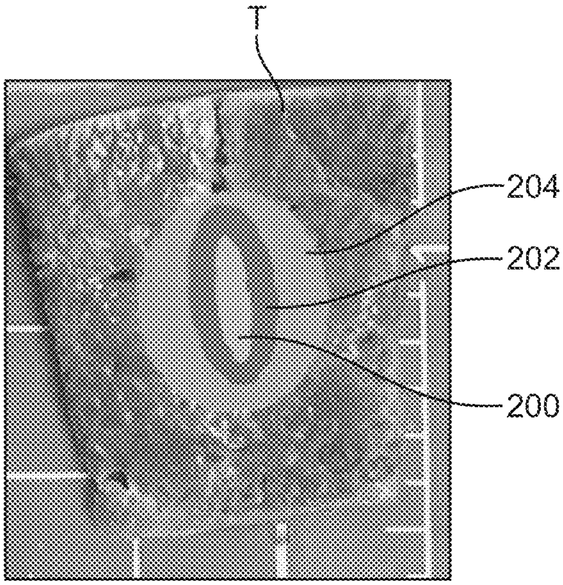

FIG. 3A illustrates an actual tissue lesion in tissue T created by delivering specialized energy to a porcine liver kept viable using a machine perfused organ preservation model. FIG. 3B illustrates the lesion demarcated with zones for clarity. The energy waveform generated a very small cavitation zone 200 (in this example, likely not an actual cavity but a needle tract from positioning the energy delivery body (needle) therein, however a cavitation zone 200 would typically be located here), a thermal zone 202, and a PEF zone 204. It may be appreciated that an inflammatory zone and/or immune response zone would be located around the PEF zone, thus following the edge of the PEF zone. The presence and size of the zones may be manipulated by the waveform, particularly the parameter values. It may be appreciated that in these examples a lesion is generated by a single dose or a single application of energy. The on-time of energy and its application during this dose is dependent on the waveform, more particularly the waveform parameters.

Energy delivery may be actuated by a variety of mechanisms, such as with the use of an actuator 132 on the instrument 102 or a foot switch operatively connected to the generator 104. Such actuation typically provides a single energy dose. The energy dose is defined by the number of packets delivered and the voltage of the packets. Each energy dose delivered to the target tissue maintains the temperature at or in the target tissue so as to generate the desired zones within the lesion. Zones such as PEF zones are maintained below a threshold for thermal ablation, particularly thermal ablation or denaturing of stromal proteins. In addition, the doses may be titrated or moderated over time so as to further reduce or eliminate thermal build up during the treatment procedure. Instead of inducing thermal damage (defined as protein coagulation at sites of danger to therapy) in PEF zones, the energy dose provides energy at a level which induces treatment of the condition, such as cancer, without damaging sensitive tissues.

Figure 4:
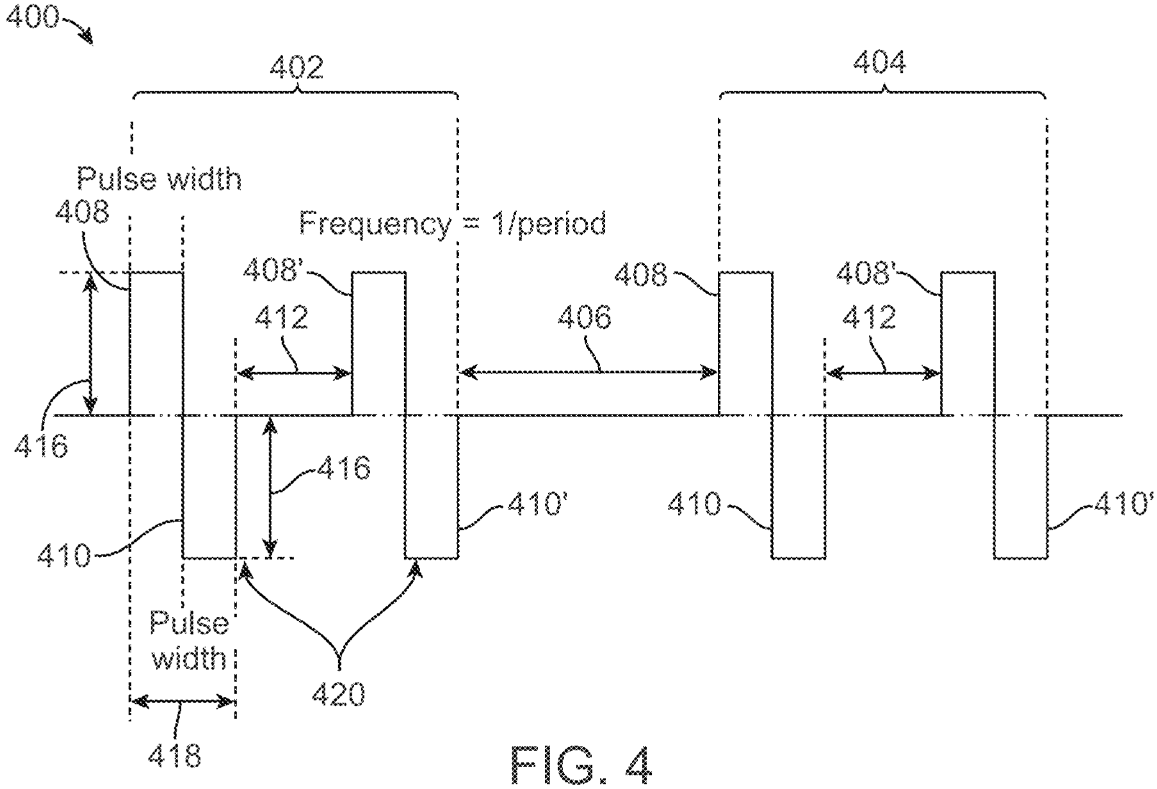
FIG. 4 illustrates an embodiment of a waveform of a signal prescribed by an energy delivery algorithm.

FIG. 4 illustrates an embodiment of a waveform 400 of a signal prescribed by an energy delivery algorithm 152. Here, two packets are shown, a first packet 402 and a second packet 404, wherein the packets 402, 404 are separated by a rest period or interpacket-delay 406. In this embodiment, each packet 402, 404 is comprised of a first biphasic pulse or cycle (comprising a first positive pulse peak 408 and a first negative pulse peak 410) and a second biphasic pulse or cycle (comprising a second positive pulse peak 408' and a second negative pulse peak 410'). The first and second biphasic pulses are separated by dead time or inter-cycle delay 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave.

It may be appreciated that manipulation of the various parameters (e.g. voltage, fundamental frequency, number of pulses per packet, number of packets, and various delays, etc.) have a variety of influences on the resultant lesion and on the body itself. In some instances, parameter changes can balance each other wherein the effect of change in one or more parameters can be balanced by a change in one or more different parameter values leading to the same or similar result. In other instances, parameter values can be tuned to create or generate different effects, such as different lesion characteristics (e.g. the presence, size and/or properties of the different zones) and/or different effects on the body. These effects on the body may be immediate, such as muscle stimulation, or delayed, such as the generation of a particular immune response.

FIG. 5 provides a table illustrating various example effects of parameter changes. Typically, the electrode style is monopolar as opposed to bipolar. In monopolar arrangements, one or more delivery electrodes are positioned near the target tissue site and at least one remote return electrode is positioned against the patient's skin. By utilizing a monopolar electrode configuration, muscle contraction intensity increases. To counteract this effect, generally a biphasic waveform or waveform comprised of sufficiently short individual pulse durations comprising a packet with appropriate delays between the pulses, so as to offset the degree in muscle contraction. This waveform variety results in treatment effect decreases, but the decrease is more subtle than the muscle contraction reduction, thus resulting in still valid PEF therapeutic applications. Monopolar configurations also decrease the risk of electrical arcing compared to bipolar or multipolar configurations, wherein all affector electrodes are placed within a similar region that may permit electrical arcing between them. Typically, the waveform utilizes biphasic pulses as opposed to monophasic pulses. The use of biphasic pulses decreases the treatment size, decreases muscle contraction and also decreases arcing risk. Thus, the use of biphasic pulses counters the increase in muscle contraction due to the monopolar electrode style. Since both monopolar electrode style and biphasic pulses reduce treatment size, treatment size can be increased by changing other variables. For example, an increase in voltage, packet duration and number of packets increases the treatment size. However, increasing these parameters have a variety of other effects. For example, increasing the voltage and increasing the packet duration each increase muscle contraction, temperature rise and risk of electrical arcing. Increasing the fundamental frequency can lower the muscle contraction but it also reduces the treatment size. Likewise, increasing the number of packets increases the treatment size but also increases the temperature rise and the treatment delivery time. The treatment delivery time can be lowered by increasing the packet delivery rate, however, this increases the temperature rise. Therefore, managing the influences of various parameter changes is a complex endeavor. This is further complicated by the increments in which these changes are made. Once considering the number of parameters and increments in which they can be changed as related to the PEF waveform and dose itself, the set of combinations is staggering in volume. This is further compounded by the influence of electrode geometry, such as where a large electrode delivering a particular electrical voltage will have different characteristics than a smaller electrode, or monopolar versus bipolar and multipolar arrangements (and the separation distances between electrodes in these arrangements). These characteristics also include the temperature rise, treatment effect size, electrical current delivered, muscle contraction, electrical arcing risk, and time required to attain coverage of a targeted treatment effect size. Furthermore, certain conditioning solutions provided to the patient may specifically be used to target and reduce the induced muscle contraction. For instance, neuromuscular blockade with pancuronium bromide, vecuronium, succynlcholine, and other blockades may be used. This reduction in muscle contraction may be used to facilitate treatment doses with lower frequencies, longer packet durations, or higher voltages to attain larger treatment effects while maintaining acceptably safe muscle contractions.

Thus, determining the appropriate parameter values for a particular outcome involves a high level of manipulation and skill. In addition, determining what particular outcome is desired also involves a high level of skill. For example, the presence, type and size of the various zones in a resultant lesion that culminates in a desired clinical outcome has not been previously known. The methods, systems and devices described herein provide both the specific parameter values and the characteristics of the desired resultant lesions that culminate in the desired clinical outcomes. Thus, the specialized energy delivered to the target tissue, typically cancerous or otherwise undesired, is generated from an algorithm 152 of the generator 104 that produces a waveform according to these parameter values.

In one embodiment, the treatment dose is provided by a waveform that is produced from a combination of parameter values that includes the following: voltage=3000V, fundamental frequency=400 kHz, number of biphasic pulses (i.e., cycles) per packet=40 cycles, inter-cycle delay=1000 microseconds, number of packets=100 packets and inter-packet delay=3 seconds. For this combination, the dose delivery time is approximately 5-6 minutes. This treatment time is substantially shorter than treatment times using conventional energy such as microwave (10 minutes), RF (20 minutes), or cryoablation (30-40 minutes). In some instances, this dose produces a lesion size of approximately 1×1×1 $cm^3$±0.3 cm in any direction. The characteristics of the resultant lesion will be described hereinbelow.

Cavitation Effects

In some instances, when delivering conventional PEF energy, cavitation occurs in the area closest the probe 702 and is considered a cavitation zone. However, the specialized energy described herein has been configured to minimize or eliminate the occurrence of cavitation. Here, cavitation is minimized or eliminated by manipulation of parameter values, particularly by including and manipulating particular inter-cycle delays.

Figure 6A:
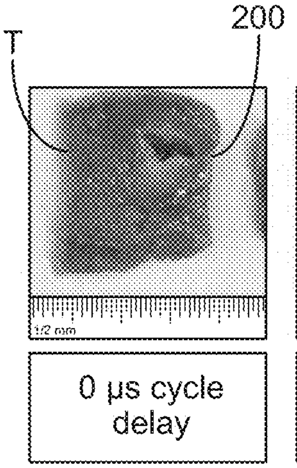
FIGS. 6A-6D illustrate tissue samples having lesions produced by waveforms having no inter-cycle delays or different inter-cycle delays.
Figure 6B:
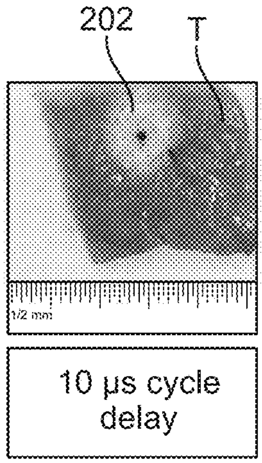
Figure 6C:
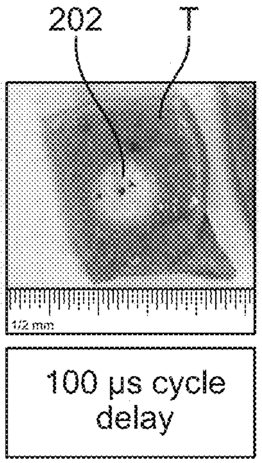
Figure 6D:
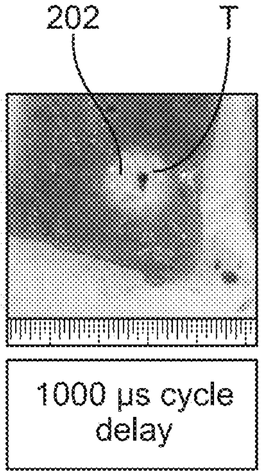

Referring to FIGS. 6A-6D, tissue samples T are shown having lesions produced by energy having waveforms with different inter-cycle delays. Each lesion was formed by placing an energy delivery body 108 (e.g. needle/probe 702, not shown) into a portion of liver tissue in a perfused organ preservation model. FIG. 5A illustrates a lesion formed from energy having a particular waveform without inter-cycle delays. Here, energy delivery is prone to electrical arcing which leads to irregularly shaped cavitary effects (i.e. a cavity/cavitation zone 200) within the lesion. While these cavitary effects are irregular, the cavity is well contained to the core of the treatment lesion. Due to the cavity formation, minimal secondary thermal effects are found due to the void of tissue (i.e. cavity) filling with perfusate. As shown in FIGS. 6B-6D, the addition of inter-cycle delays, such as 10 μs, 100 μs, 1000 μs inter-cycle delays respectively, removed the cavitary effects entirely. The small hole in the center of the lesion is due to the insertion of the probe 702 rather than the formation of a cavity. Thus, the amount of cavitation, including the complete elimination of cavitation, can be controlled and manipulated by aspects of the waveform itself, particularly by the inclusion of particular inter-cycle delays. Thus, at least a 10 μs inter-cycle delay in a PEF waveform is desired to eliminate cavitation, such as when the PEF waveform has a fundamental frequency of 400 kHz, 40 cycles are provided per packet, and 100 packets are provided per dose. It may be appreciated that as the length of the inter-cycle delays increase, arcing and electrical discharge decrease thereby decreasing cavitation. However, such decrease begins to level off and plateau, such as an inter-cycle delay near 1000 μs. Therefore, in some embodiments, a 1000 μs delay is preferred so as to most effectively minimize or eliminate cavitation without causing undue extension of total treatment time. It may be appreciated that such a reduction in cavitation delivers more of the intended energy to the target tissue forming the lesion. Thus, in this example, the thermal zone 202 increased indicating that more energy was delivered than desired for creating a PEF zone.

Figure 7A:
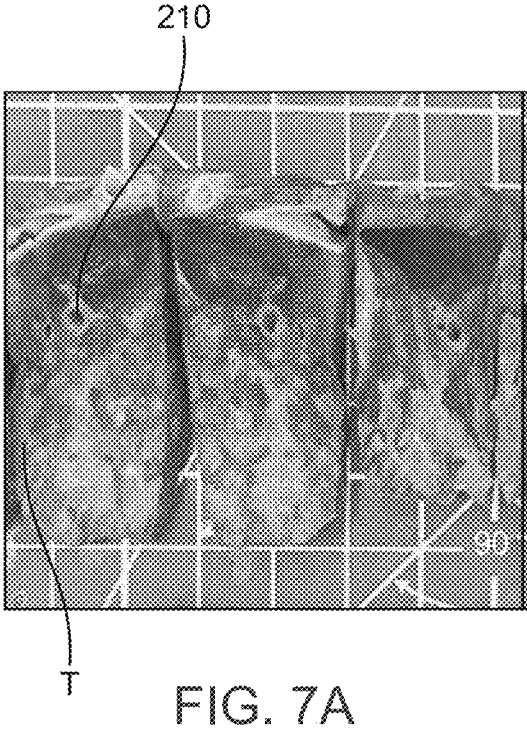
FIGS. 7A-7B illustrates in vivo tissue samples from a preclinical study in porcine lung tissue.
Figure 7B:
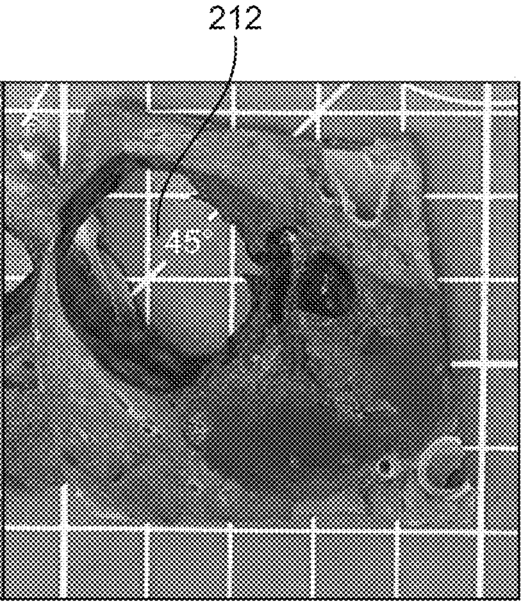

Likewise, FIG. 7A-7B illustrates in vivo tissue samples T from a preclinical study in porcine lung tissue. FIG. 7A shows gross lung tissue having lesions 210 formed by delivering energy having a particular waveform with inter-cycle delays. As shown, tissue cavitation was prevented within the lung parenchyma. It may be appreciated that in some embodiments, similar effects can be achieved by including inter-packet delays instead of or in addition to inter-cycle delays. FIG. 7B shows lung tissue having a lesion formed from delivering energy having the waveform without inter-cycle delays. As shown, the core treatment area is mostly comprised of a large hemorrhagic (blood filling) region 212 well contained within the anatomical interlobular septa. The treatment without the inter-cycle delays produced the largest cavitation area.

Thermal Effects

It may be appreciated that in some instances, PEF energy can generate lesions having areas of thermal sequelae when using particular waveforms and methodology, to name a few factors. This most often occurs when attempting to generate larger treatment zones. When higher levels of energy delivery are used, larger treatment zones can be achieved, however this can also cause an increase in white tissue coagulation due to Joule heating effects. This typically occurs in areas closer to the delivery electrode. Consequently, the specialized energy diminishes, eliminates, or otherwise controls the presence of thermal effects in generated lesions. It may be appreciated that in some instances a small amount of thermal effects can be beneficial in invoking a particular immune response in the patient. Thus, thermal effects can be desired in some instances. However, control of the amount of thermal effects maintains the balance between benefit and undesired effects. Thus, in some embodiments, the ratio or combination of effects (e.g. thermal effects vs. PEF effects) is optimized to maximize and/or customize an immune response in the patient. Thus, in some instances there is a "golden ratio" of effects or combination of waveform parameters that adjusts the local tissue characteristics in a manner that elicits a specific outcome from the body. Thus, in some embodiments, the resulting improved waveforms and energy delivery algorithms ultimately maximize and/or beneficially control the immune response in the patient.

In some embodiments, thermal effects are minimized or controlled by manipulation of parameter values, particularly by including and manipulating particular inter-cycle delays. For example, in some embodiments, the addition of inter-cycle delays and inter-packet delays enhance the ability to maximize the PEF effected volume of a generated lesion, while minimizing thermal zones and cavitary zones. In particular, in some embodiments, the inclusion of particular inter-packet delays minimizes thermal zones.

Figure 8:
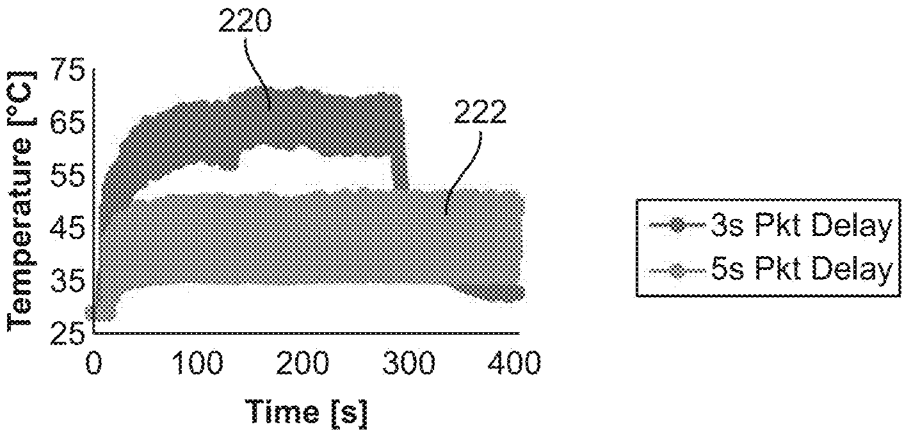
FIG. 8 illustrates how integrating inter-packet delays can aid in mitigating the thermal effects of PEF energy delivery.

FIG. 8 illustrates how integrating inter-packet delays into the energy waveform can aid in mitigating the thermal effects of PEF energy delivery. Here, two curves are shown. A first curve 220 illustrates the temperature rise over time when a 3 second inter-packet delay 406 is included in the waveform. And, a second curve 222 illustrates the temperature rise over time when a 5 second inter-packet delay 406 is included in the waveform. As shown, the 5 second inter-packet delay 406 results in a lower temperature rise over time. This is achieved simply by manipulation of the waveform rather than the addition of any cooling agents, etc. In some instances, thermal effects occur at or above 65° C. Therefore, in some instances, the waveform having the 5 second inter-packet delay 406 eliminates any thermal effects while the 3 second inter-packet delay 406 may result in minor thermal effects. Although inter-packet delays 406 lower temperature rise over time, they also increase overall treatment time. In order to balance factors, a 3 second inter-packet delay 406 was included in the specialized energy since minor thermal effects are tolerated and in some instances beneficial. However, it may be appreciated that inter-packet delays of 3-5 seconds are acceptable, including 3 seconds, 3.5 seconds, 4 seconds, 4.5 seconds and 5 seconds, and all subranges therebetween. Likewise, inter-packet delays 406 of greater than 5 seconds may be used if longer treatment times are tolerated.

It may be appreciated that a 3 second delay may be slightly longer than 3 seconds when synchronizing with the heartbeat. For example, in some instances, the energy delivery algorithm has a 3 second inter-packet delay and then waits until the next heartbeat triggers the energy delivery. Thus, the actual inter-packet delay may be 3.1 seconds, 3.2 seconds, 3.3 seconds, etc. In some instances, the delay may be as long as 4.49 seconds (e.g. for a 40 bpm patient maximally misaligning with a 3 second-interpacket delay). It may be appreciated that the overall lesion size is not significantly affected by the introduction of inter-cycle delays.

In PEF zones, energy is delivered in a manner so to treat the tissue in a non-thermal manner (i.e. below a threshold for causing thermal ablation). Consequently, when extracellular matrices are present, the extracellular matrices are preserved, and the targeted tissue maintains its structural architecture including blood vessels and lymphatics. Thus, sensitive structures, such as biological lumens, blood vessels, nerves, etc, are able to be preserved which are critical to maintaining the integrity and functionality of the tissue. This provides a number of benefits. To begin, this allows for the treatment of tissues that are often considered untreatable by conventional methods. Target tissues that are near sensitive structures are typically unresectable by surgical methods due to the inability to thoroughly and effectively surgically separate the tissue from the sensitive structures. Likewise, many conventional non-surgical therapies are contraindicated due to the potential for damage to the sensitive structures by the therapy or because the therapies are deemed ineffective due to the proximity of the sensitive structures. In addition, the ability to treat tissue near sensitive structures also provides a more comprehensive treatment in that malignant margins are not left near sensitive structures. Once tissue is treated, the survival of the structural architecture also allows for the natural influx of biological elements, such as components of the immune system, or for the introduction of various agents to further the therapeutic treatment.

The fine tuning and adjustment of the ratio of the tissue zones (cavitation zone 200, thermal zone 202, PEF zone 204) within a specific treatment site promotes a cascade of increased recruitment for immunological elements, such as Regulatory T-cells (Tregs), CD4 (T helper), CD8 (T cytotoxic), CD3 (T cell), CD2 (B cell), FoxP3 (Treg), Pan-CK (Tumor), PD-L1, MIF & M2F, DC, NK, MDSC, NF, and other adaptive immune cell types, that is unique to the energy delivered and resultant ratios of the lesion zones, as will be described in more detail hereinbelow.

Lesion classifications, such as cavitation zone 200, thermal zone 202, PEF zone 204, can be measured grossly, but also monitored in real-time based on the tissue properties (i.e., tissue density, impedance change, etc.) and imaging modalities such as computerized tomography, etc. Further, in some embodiments, these ratios are centered around the measurement of other clinically relevant and quantifiable tools such as local temperature, tissue impedance, and tissue density, to name a few.

In addition to manipulating the parameter values to generate desired lesion zones, parameter values were further manipulated to maximize lesion size while ensuring patient safety, a desirable treatment time, reduced electrical arcing risk, reduced muscle contraction, and reduced temperature rise, to name a few. Extensive studies were undertaken to determine the parameters for the desired dose. Studies included evaluating the following parameter combinations:

TABLE 1

| No. | Voltage, V | Fundamental Frequency, kHz | Cycles, count | Inter-Cycle Delay, μs | Packets, count | Inter-Packet Delay, s |
|---|---|---|---|---|---|---|
| 1 | 2500 V | 400 kHz | 40 cycles | 1000 μs | 100 packets | 3 second |
| 2 | 2500 V | 400 kHz | 60 cycles | 1000 μs | 100 packets | 3 second |
| 3 | 3000 V | 400 kHz | 40 cycles | 1000 μs | 100 packets | 3 second |

TABLE 1-continued

| No. | Voltage, V | Fundamental Frequency, kHz | Cycles, count | Inter-Cycle Delay, μs | Packets, count | Inter-Packet Delay, s |
|---|---|---|---|---|---|---|
| 4 | 3000 V | 400 kHz | 60 cycles | 1000 μs | 100 packets | 3 second |
| 5 | 3300 V | 400 kHz | 60 cycles | 1000 μs | 100 packets | 3 second |
| 6 | 2500 V | 400 kHz | 40 cycles | 500 μs | 100 packets | 3 second |
| 7 | 2500 V | 400 kHz | 60 cycles | 500 μs | 100 packets | 3 second |
| 8 | 3000 V | 400 kHz | 40 cycles | 500 μs | 100 packets | 3 second |
| 9 | 3000 V | 400 kHz | 60 cycles | 500 μs | 100 packets | 3 second |
| 10 | 3300 V | 400 kHz | 60 cycles | 500 μs | 100 packets | 3 second |

The treatments were delivered to a liver parenchyma as it is an excellent tissue in which to measure lesion sizes accurately. In one study, two pigs were utilized; both animals were euthanized at 3-days post-op. A needle electrode was applied to deliver treatments to the liver parenchyma of each 3-day survival animal. To improve visibility and ensure desired positioning of the needle electrode within the intended targets, a laparotomy was employed. Following a laparotomy, twenty-four treatments were delivered to the liver parenchyma of each 3-day survival animal. All treatment sites were resected and sectioned for gross ablation analysis.

Figure 9:
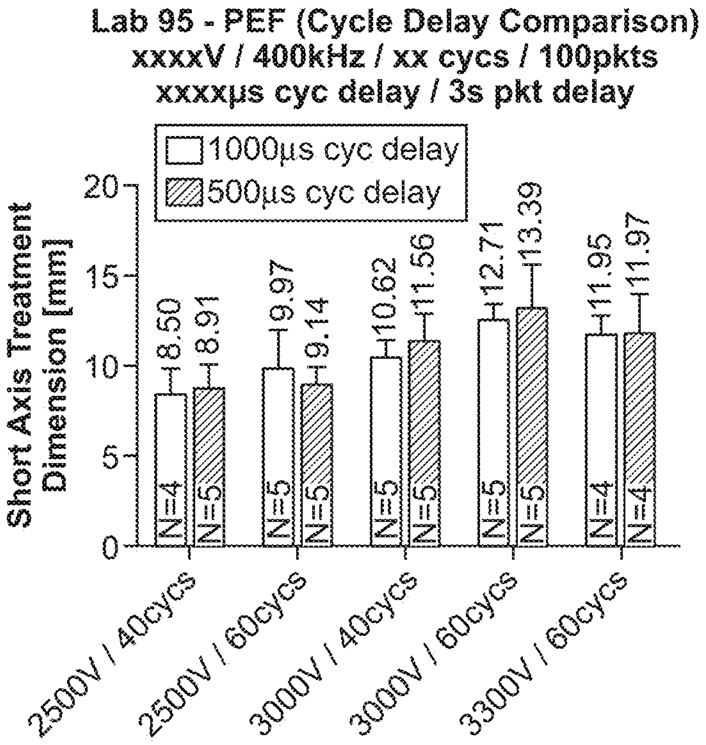
FIG. 9 illustrates in vivo data captured from a preclinical study in porcine liver tissue.

As shown in Table 1, all treatments were delivered at a fundamental frequency of 400 kHz and for 100 packets. Treatments were delivered with R-triggered cardiac synchronization, with a 3 second rest period implemented between subsequent packets (approximate cadence of 20 packets per minute (pkts/min)). Inter-cycle delays of either 500 μs or 1000 μs were used to confirm the absence of change to lesion size from these values. In this study, there was no statistical difference found in overall treatment zone size, nor treatment characteristics between treatments that employed a 500 μs cycle delay and a 1000 μs cycle delay, as illustrated in FIG. 9. FIG. 9 illustrates in vivo data captured from this preclinical study in porcine liver tissue. The column plots illustrate the lack of influence that inter-cycle delays have on the overall treatment size across five varying energy protocols (varying voltage amplitudes and on-time per packet).

Treatment volumes were calculated based on the short axis measurements. The equation for this calculation can be found in equation 1, where r is the short-axis radius dimension.

$$V = 4/3 * \pi * (r)^\wedge 2 * (r + \text{applicator exposure length}) \quad \text{[Equation 1]}$$

Figure 10A:
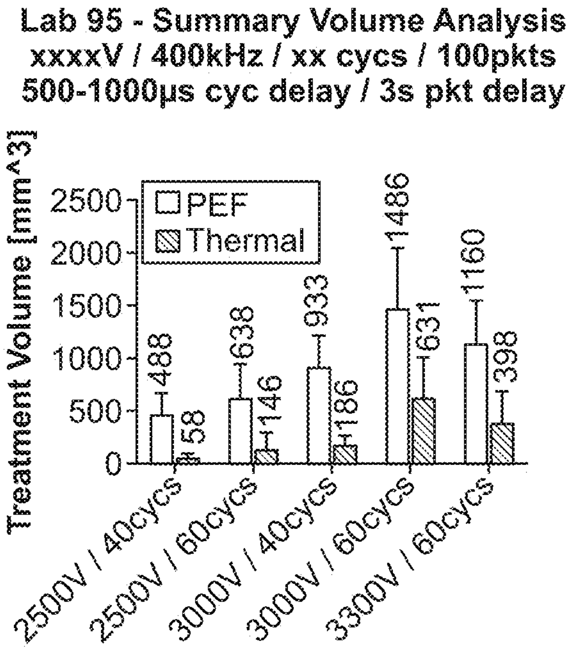
FIGS. 10A-10B illustrate additional in vivo data captured from a preclinical study in porcine liver tissue.
Figure 10B:
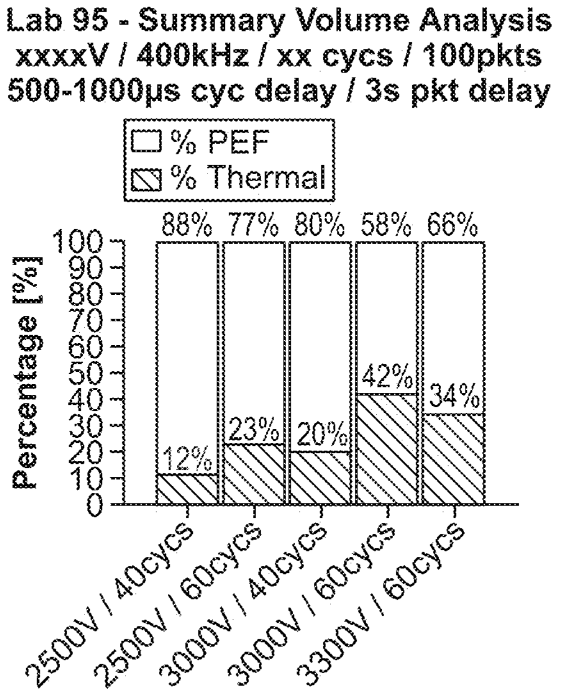

FIGS. 10A-10B depict the volume treatment zone measurements, post-fixation for both animals. As these calculated volumes were based off short axis measurements, the same trends occurred as the short access measurement analysis with an increase in treatment volume with an increase in voltage and packet on-time, with the exception of the 3300V/60 cycle protocol. In this instance, this could be attributed to partial electrical discharge at the treatment site. The column plots of FIGS. 10A-10B illustrate influence of voltage amplitude and on-time per packet within the ratio of total effected tissue and thermally effected tissue. FIG. 10A illustrates the short-axis treatment volume calculation for variable-voltage amplitude and cycle counts, and FIG. 10B illustrates the percentage of thermal necrosis and PEF within the treatment volume. Overall, interpretation of the largest total PEF zone volume (and thus greatest cell debris and antigen bioavailability for the immune system) coupled with the acceptable proportion of thermally-apparent treatment effects, it is determined that parameter values of 3000V and 40 cycles (100 s packet active time) provides the desired outcome, as is later confirmed by human studies.

Figure 11A:
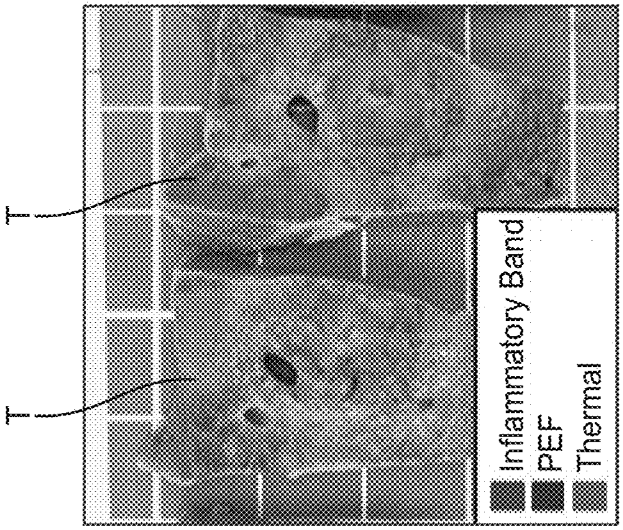
FIGS. 11A-11B illustrates in vivo samples captured from a preclinical study in porcine liver tissue.
Figure 11B:
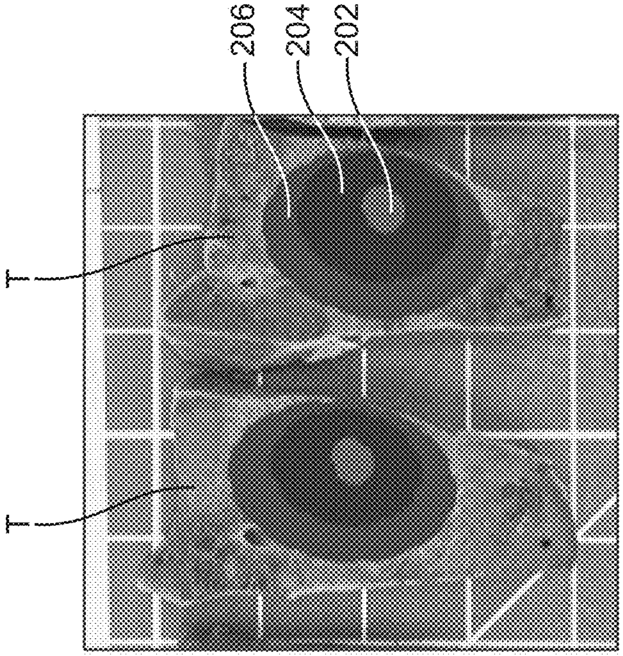

The liver samples were reviewed histologically in a blinded fashion without knowledge of the treatment delivered at any given liver site. An overall assessment of the size of the treated liver parenchyma was provided based on the tissue on the glass slides (e.g. 0.7×0.7 cm to 1.5×1.2 cm). Qualitative assessment of the lesions was also provided. Overall, the lesions were determined to be quite similar with a reproducible pattern of injury. Histological analyses of the tissue lesions have revealed an additional zone within each lesion. The additional zone is an effect of PEF energy delivery and is an inflammatory zone. Histological analysis performed on tissue samples indicate a peripheral inflammatory response at 3 days post-op. FIGS. 11A-11B illustrate in vivo samples captured from a preclinical study in porcine liver tissue. FIG. 11A are photographs of the lesions of the tissue samples T. FIG. 11B superimpose "bullseye" images illustrating the zones found in the lesions of FIG. 11A. The zones include a thermal zone 202, a PEF zone 204 and an inflammatory zone 206, from inward moving outward. The tissue samples illustrate influence of frequency on the ratio of total effected tissue and thermally effected tissue, and a peripheral inflammatory band or zone 206. In some embodiments, lower frequencies generate a larger peripheral inflammatory response or zone 206 and a larger region of PEF energy effects or zone 204. One variable that appeared to differ somewhat between treatments was width of the peripheral inflammatory zone 206/partially devitalized hepatocytes relative to the size of the central completely ablated hepatic parenchyma. There is a reproducible pattern of injury with respect to the size of the ablated liver parenchyma, as well as the "bullseye" nature of central tissue ablation, to partially viable/inflammatory zone, to a rapid fall off of completely normal/uninvolved adjacent parenchyma.

Thus, the refined dose of specialized energy described herein generates a treatment lesion (e.g. 10 mm in diameter) with minimal thermal volume, particularly in comparison to lesions generated by conventional pulsed electric field technology. In some embodiments, the treatment duration is 5 minutes. The refined dose provided by the specialized waveforms maximizes the PEF treatment effect zone while minimizing thermal effects. At this specifically-tuned dosing, the PEF energy causes release of tumor antigens, stimulates the body's innate and adaptive immune response such as due to enhanced release of neo-antigens, stimulated immunogenic cell death (e.g. necroptosis, pyroptosis, etc.), and enhanced sensitivity to antigens due to limited encapsulation and scarring of the treated area. In addition, in some embodiments the specialized energy disrupts the immunosuppressive tumor immune microenvironment (TME). Thus, embodiments of the treatment systems maximize antigen release and increase the immune response.

VIII. Immune Response

It has been determined that the refined dose of specialized energy generates a treatment lesion that induces an immune response that is superior to conventional radiofrequency (RF) treatments. When the energy is used to treat cancerous tumors, this immune response harnesses the body to further eliminate the cancerous cells such as residual cancer cells, metastatic cancer cells or later developing cancer cells. This has been studied in multiple murine models of cancer wherein the specialized PEF treatment elicits a tumor specific immune response. For example, data has been generated from a syngeneic, orthotopic model of triple-negative breast cancer (EMT6 Tumor) and a metastatic model of melanoma (B16-F10/B16-OVA Tumors). To understand the impact of this specialized PEF treatment on tumor suppression, a survival study was performed in EMT6 tumor bearing mice. Next, anti-tumor mechanisms were identified that are mediated by the PEF to better describe the tumor suppression observed in the EMT6 model. Further, studies were performed to determine that the tumor antigen release induced by the PEF was competent enough to drive a tumor specific T cell response.

This is in contrast to conventional radiofrequency ablation (RFA). RFA causes a very different effect in the target tissue as illustrated in the following study:

Purpose

The purpose of this study is to compare the treatment effect of radiofrequency ablation (RFA) and specialized pulsed electric fields (PEF) in EMT6 tumor model. The endpoints were the following: a) cytokine profiling and HMGB1 quantification of blood serum collected from the animals, b) histology (H&E) and flow cytometric analyses of the tumors.

Biological Groups

TABLE 2

| Study Groups | | |
|---|---|---|
| Biological Groups | Tumor Model | Number of mice per group |
| Sham Treatment group | Bilateral EMT6 | 10 |
| 2500 V PEF | Bilateral EMT6 | 10 |
| RFA (3 W, 15 s) | Bilateral EMT6 | 10 |

Study Overview

Figure 12A:
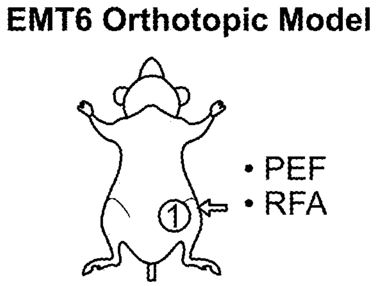
FIGS. 12A-12B illustrate a study design.
Figure 12B:
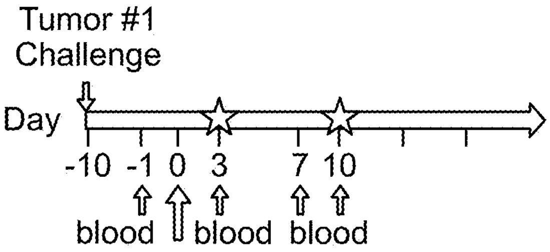

A total of thirty (30) female Balb/c mice were used for this study. All mice were transplanted with 0.2×106 EMT6 cells in the left mammary fat pad (FIG. 12A, Tumor labeled “1”). Eight (8) days after the tumor challenge (Day 0), twenty (20) of the tumor-bearing mice (all groups except the untreated control group) had their tumors (approximately 4-6 mm in length) directly treated with either 2500V specialized PEF or RFA (3 W, 15 s) based on the respective groups mentioned above. Referring to FIG. 12B, one day before treatment (Day −1), blood was drawn from all the mice retro-orbitally for serum isolation. Retro-orbital blood draws were repeated 3, 7, and 10 days after PEF/RFA treatment. On Day 3, three (3) mice from each group were humanely euthanized for the collection of tumors which were used for histological analyses. On Day 10, the remaining seven (7) animals from all the groups were humanely euthanized for the collection of tumors which were further used for flow cytometric analyses.

Flow Cytometric Analyses

The tumors from the remaining seven mice from each group were collected on Day 10 post-treatment. The tumors were dissociated, and cell fraction were isolated using Tumor Dissociation Kit (Miltenyi Biotec (130-096-730)) as per the protocol recommended by the manufacturer. The cells were stained for flow cytometry using the antibodies mentioned in the table below. Flow cytometry were performed using the CytoFLEX (Beckman Coulter) flow cytometer.

TABLE 3

| MARKER | FLUOROCHROME |
|---|---|
| Viakrome | APC |
| CD45 | PB |
| CD3 | APC-Cy7 |
| CD4 | PerCP-Cy5.5 |
| CD8 | BV650 |
| CD19 | PE |
| PD-L1 | BV605 |
| PD-1 (CD279) | PE-Cy7 |
| CD11b | BV785 |

Figure 13:
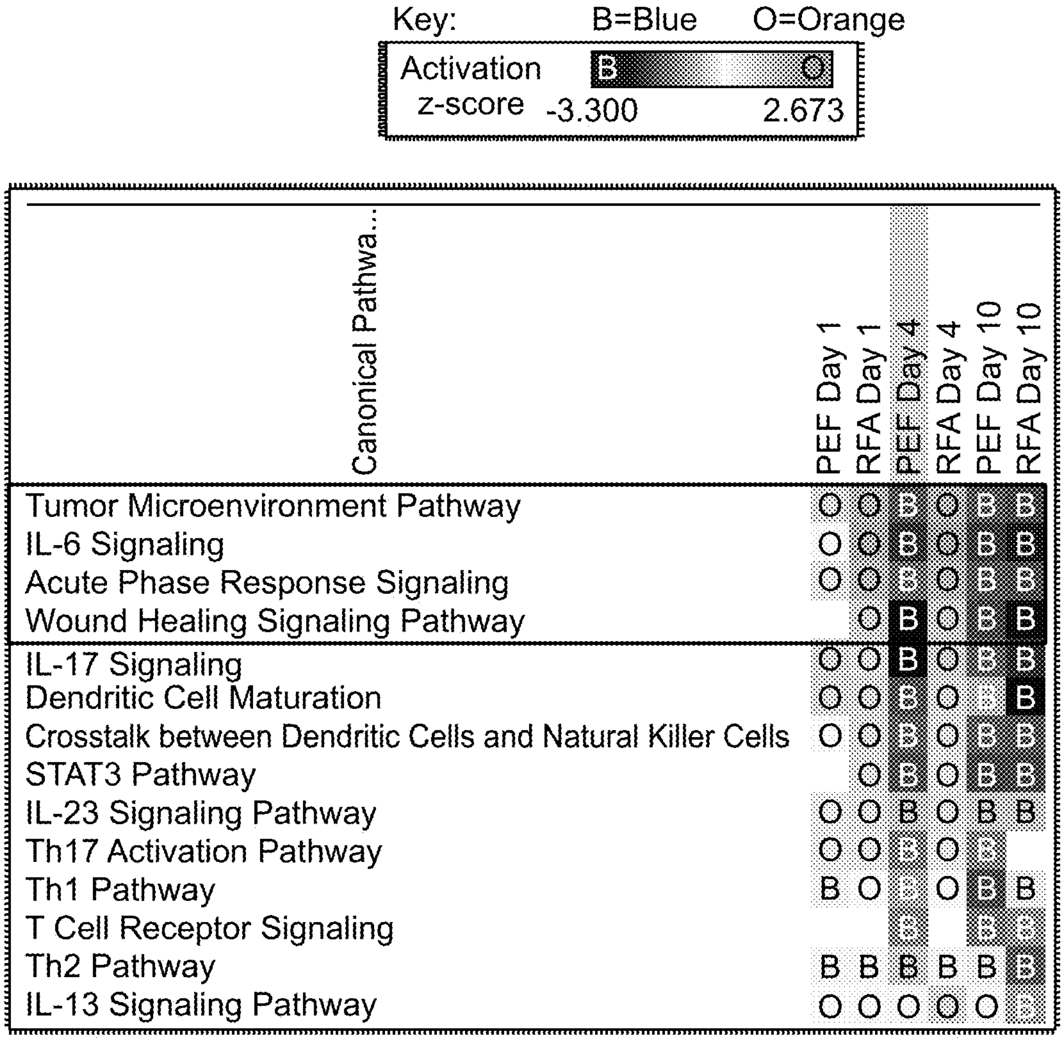
FIG. 13 illustrates a comparison of serum cytokines profiling induced by PEF or RFA treatment

FIG. 13 illustrates a comparison of serum cytokines profiling induced by PEF or RFA treatment at 1, 4 and 10 days post ablation. On Day 4, the specialized PEF treated group showed the following:

Decrease in CSF2, CSF3, CCL2, IL1β (promoting a decrease of myeloid derived suppressor cells)

Decrease in CSF1, IL13 and increase in IL4 (reducing proliferation of tumor associated macrophages)

Decrease in IL6 and JAK-STAT Signaling (reducing proliferation and survival of cancer cells as well as decrease angiogenesis The above-mentioned effects on Day 4 were exactly opposite in the RFA-treated group. Therefore, the specialized PEF therapy is superior to RFA treatment in providing a beneficial immune response, particularly as it relates to the treatment of tumors.

Figure 14A:
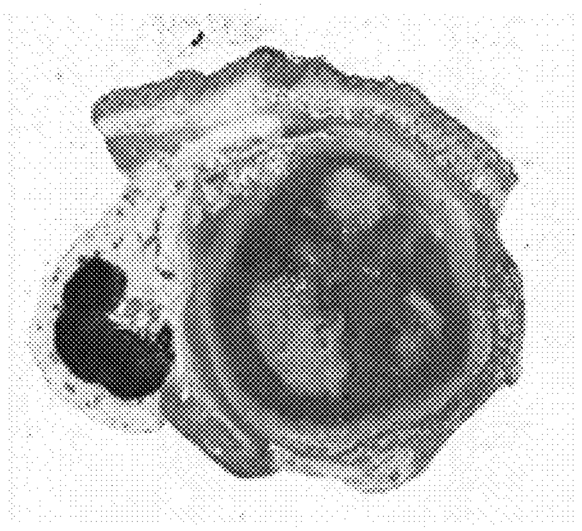
FIGS. 14A-14B illustrates the H&E staining of tumor samples collected 4 days post treatment.
Figure 14B:
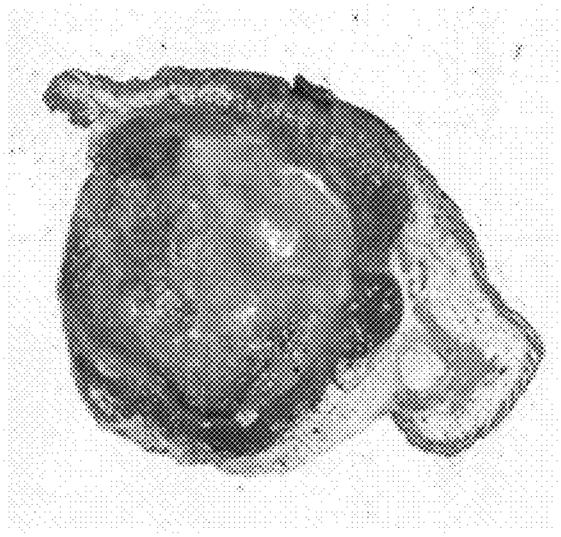

FIGS. 14A-14B illustrates the H&E staining of tumor samples collected 4 days post treatment confirming matched ablation volumes.

A similar study was undertaken to profile cytokines in tumors and in blood:

Study Overview

Figure 15:
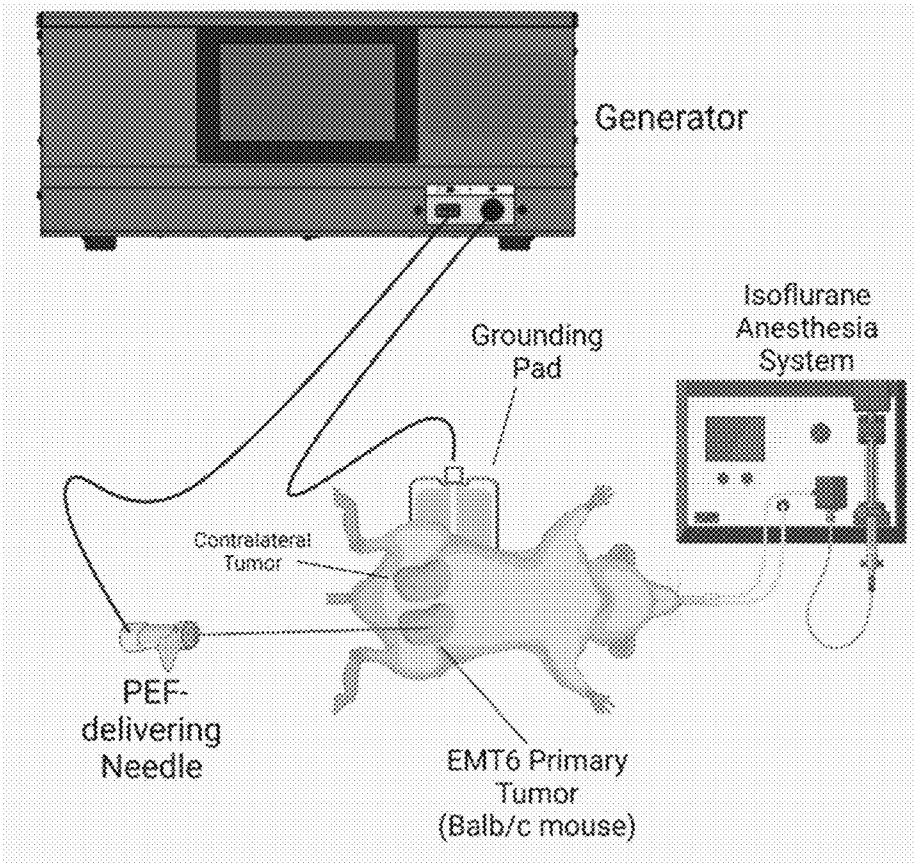
FIG. 15 illustrates an EMT6 model of a study.
Figure 16:
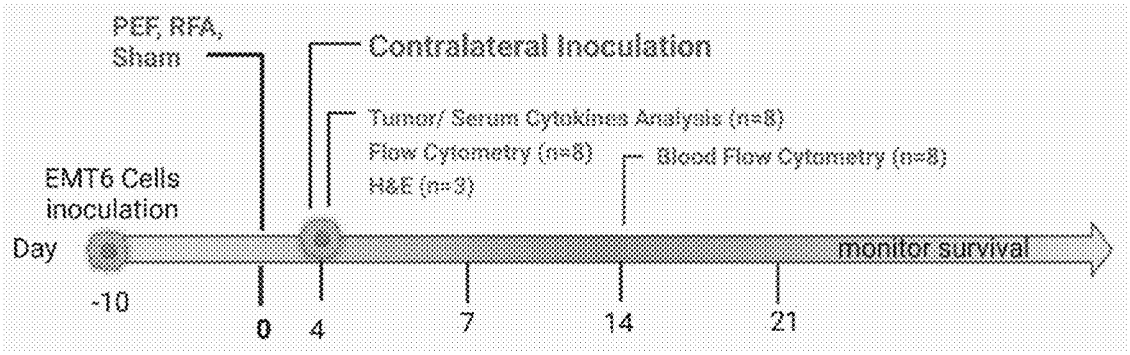
FIG. 16 illustrates a study design for the model of FIG. 15.

Again, Balb/c mice were used for this study; each cohort had 10 mice. All mice were transplanted with $0.2\times10^6$ EMT6 cells in the left mammary fat pad (FIG. 15, bottom tumor). Once the tumors reached 5-7 mm in diameter, the tumors were treated with radiofrequency ablation (RFA), specialized PEF or were a sham. The treatments were incomplete so as to retain some tumor tissue for analysis. The RFA was delivered at 3 watts for 15 seconds. The specialized PEF was delivered using a waveform having a voltage of 2500V, a base frequency of 400 kHz, 40 cycles per packet and 100 packets. Each was delivered through a single needle electrode. The protocols were optimized to specifically ablate 80% of the tumor to investigate the resulting tumor response. Four days after ablation or sham, a contralateral tumor was inoculated in the opposite site of the mammary pad (FIG. 15, top tumor) to monitor for any abscopal effect. After ablation, at different time points as illustrated in FIG. 16, various cytokines in tumors and in blood were profiled.

In addition, the local immune response was studied by flow cytometry and primary and contralateral tumor growth was monitored.

Figures 17, 18:
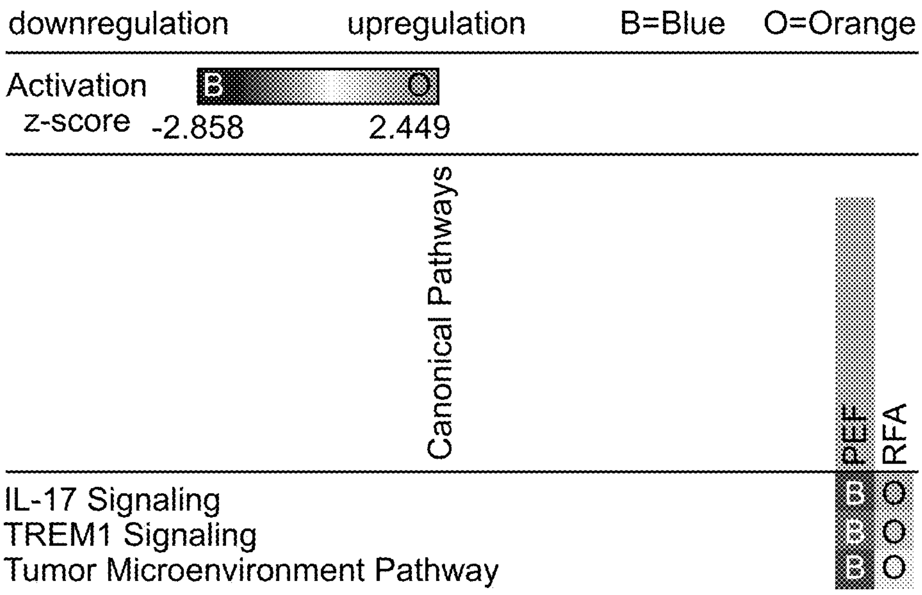
FIG. 17 illustrates a heatmap showing activation (for RFA) or repression (for PEF) of tumor cytokines.
FIG. 18 provides a table of the modulation of specific the cytokines by PEF.

Four days post ablation (RFA or PEF), the treated tumors were harvested and homogenized to extract the total proteins. The samples were analyzed by a CRO (Evev Biotechnologies) to profile the expression of 44 cytokines. The cytokines levels data were analyzed by Ingenuity Pathways Analysis, a software capable of generating biological networks based on the expression changes exhibited in a dataset. The software provided the top biological pathways based on the changes observed in cytokines measured in the tumor samples. Referring to FIG. 17, the heatmap shows activation (for RFA) or repression (for PEF) of the specific pathways.

Drastic differences were seen between the PEF and RFA with the PEF that was driving downregulation of specific pathways when RFA was causing the opposite effects. The modulation of the specific cytokines by PEF is listed in the table of FIG. 18 and is causing overlapping effects as seen in serum such as reduced inflammation, angiogenesis, tumor cell proliferation as well as decrease accumulation of MDSC and TAMs. The serum and tumor cytokines analysis show that specialized PEF and RFA have distinct differing effects on inflammation, immune activation and tumor proliferation.

Figure 19A:
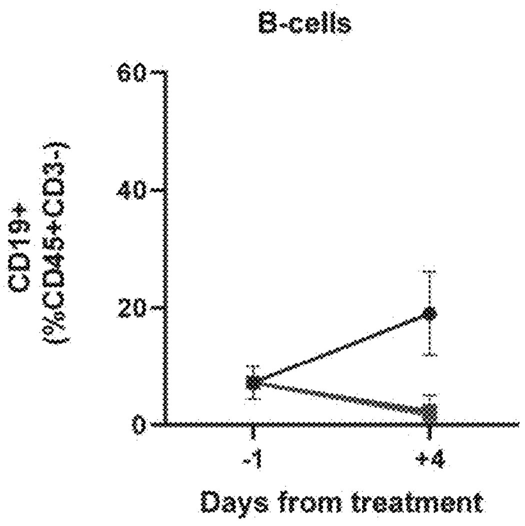
FIGS. 19A-19B show that PEF was capable of recruiting more B-cells and more dendritic cells than RF to drive a stronger immune response.
Figure 19B:
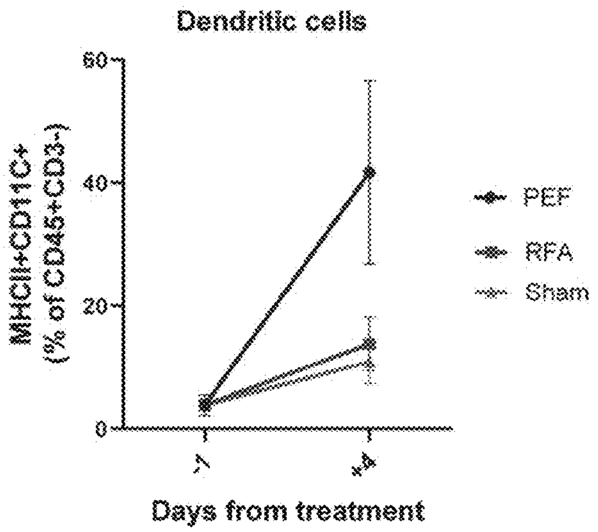

One day before treatment (RFA or PEF) and 4 days post ablations tumors were collected tumors and digested to single cell suspension to conduct flowcytometric analysis to enumerate dendritic cells (CD11c+/MHC class II+) and B-cells (CD19+). FIGS. 19A-19B show that the PEF was capable of recruiting more B-cells and more dendritic cells than RFA and Sham to drive a stronger immune response. Because PEF does not cause massive tumor antigen denaturation, the increased presence of dendritic cells would typically lead to a stronger T cell expansion. An accumulation of B-cells in response to the specialized PEF has also been observed in clinical trials.

Figure 20:
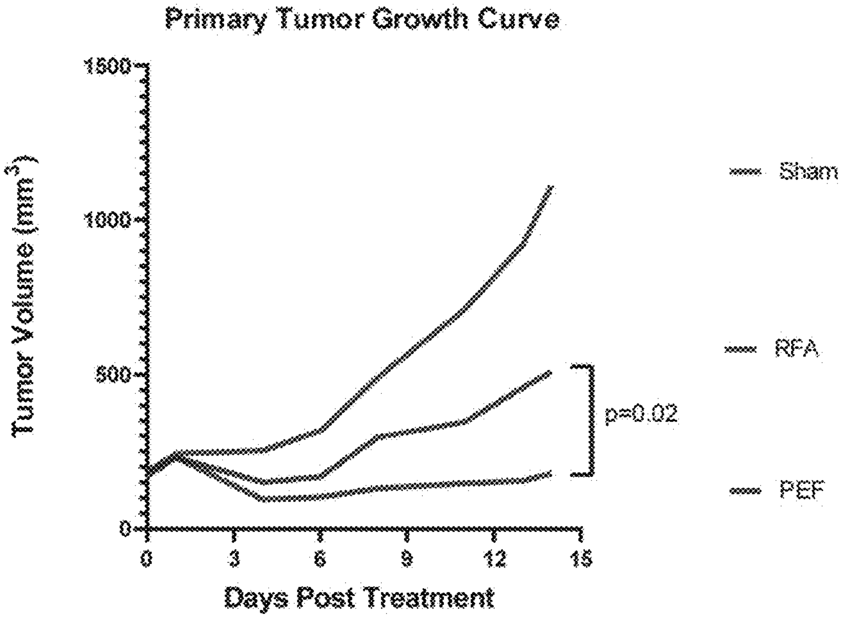
FIG. 20 illustrates primary tumor growth overtime.

In the mice that were not euthanized for cytokine analysis or flow cytometry, the primary tumor growth was monitored. FIG. 20 shows the primary tumor growth over time, up to 15 days post treatment. As shown. Both ablation modalities (RF and PEF) caused greater reduction of tumor volume compared to Sham. Although for match ablations, PEF was more effective than RFA in suppressing tumor growth.

Figure 21:
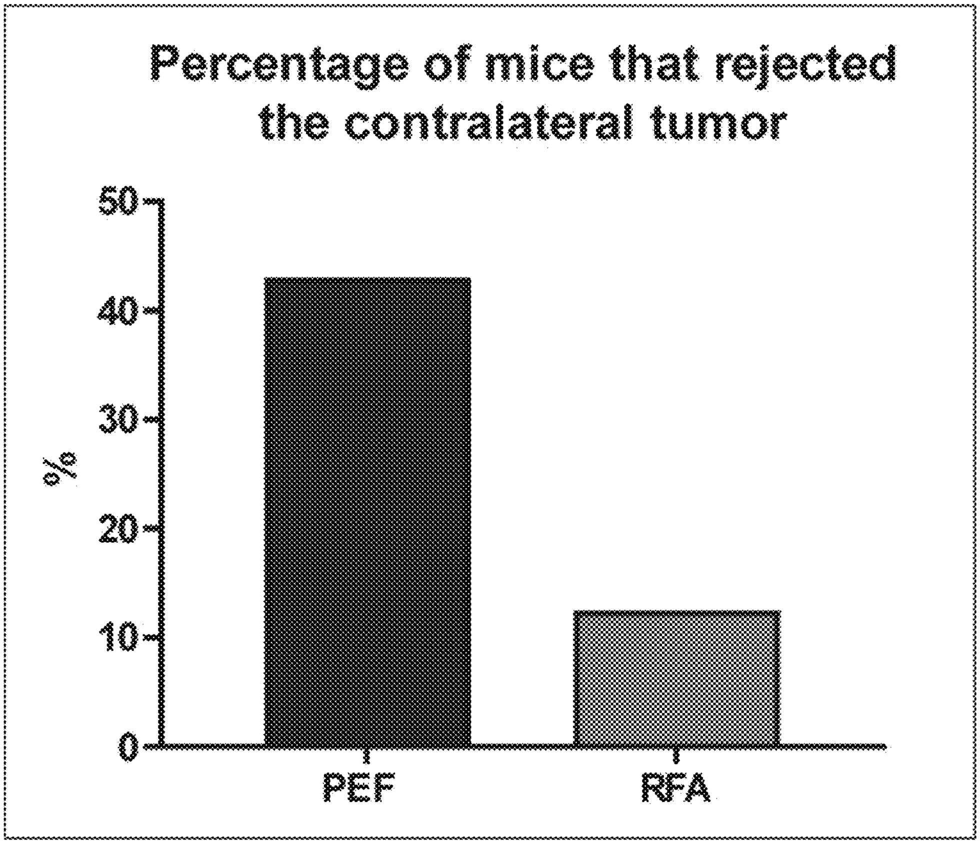
FIG. 21 illustrates the percentage of mice that showed contralateral growth.

Contralateral tumors were inoculated 4 days after the ablation (RFA or PEF) of the primary tumor and their growth was monitored 3 times per week. FIG. 21 illustrates the percentage of mice that showed contralateral tumor growth. As shown, the mice that received PEF had the greatest percentage of mice that rejected the contralateral tumor due to a better immune response that was trained to eliminate the cancer cells as a result of the effects of the PEF treatment. Thus, specialized PEF treatment evokes a systemic immune response that drives a stronger abscopal effect than RFA.

In addition, partial or incomplete treatment of tumors with PEF still evoke systemic effects and do not lead to more aggressive tumor growth. This is in contrast to RFA wherein incomplete treatment of tumors with RFA leads to worse outcomes because the surviving tumor becomes more aggressive. Thus, PEF is a safer treatment in that any imperfections in treatment coverage do not lead to worse prognoses for the patient as would be the case with RFA.

It has also been determined that the refined dose of specialized energy generates a treatment lesion that induces an immune response that is superior to conventional PEF treatments. When the energy is used to treat cancerous tumors, this immune response harnesses the body to further eliminate the cancerous cells such as residual cancer cells, metastatic cancer cells or later developing cancer cells. This has been studied in multiple murine models of cancer wherein the specialized PEF treatment elicits a tumor specific immune response. For example, data has been generated from a syngeneic, orthotopic model of triple-negative breast cancer (EMT6 Tumor) and a metastatic model of melanoma (B16-F10/B16-OVA Tumors). To understand the impact of this specialized PEF treatment on tumor suppression, a survival study was performed in EMT6 tumor bearing mice. Next, anti-tumor mechanisms were identified that are mediated by PEF to better describe the tumor suppression observed in the EMT6 model. Further, studies were performed to determine that the tumor antigen release induced by PEF was competent enough to drive a tumor specific T cell response.

Further, to evaluate the safety and initial feasibility of the refined dose of the specialized PEF energy described herein to treat solid tumors, a prospective, two-arm, non-randomized, concurrently controlled, multi-center, open-label, treat and resect study was undertaken. The pre- to post-treatment changes to immune cell populations in the blood of a patient whose tumor was treated with PEF has been analyzed.

Studies

Example 1

Local Treatment with Specialized Pulsed Electric Fields Generates a Tumor Specific Response Objectives: PEF is an emerging technology being assessed for the cytoreductive treatment of tumors. PEF energy does not thermally denature proteins, allowing the release of intact tumor-associated antigens for antigen-presenting cells to drive a tumor specific response. This may promote an improved local response of the treated tumors and an abscopal effect. The refined dose of the specialized PEF energy optimizes the PEF zone and induces additional zones which promote these responses, such as an enhanced effect that is related to an antigen-specific adaptive immune response. The purpose of this study was to evaluate the presence of antigen-specific cytotoxic T-cells in preclinical tumors treated with the specialized PEF therapy.

Methods: C57BL/6J mice were inoculated (s.c. injection, $1\times10^6$ cells per 50 μL Matrigel:PBS−/−) in the right flank with either a B16-F10 tumor cell line genetically modified to express chicken ovalbumin protein (B16-OVA) or a negative control tumor (B16-F10). Nine days post-inoculation, mice were randomized into treatment groups including PEF and no treatment control (NTC). PEF energy was delivered using a single needle with a grounding electropad configuration. For mice treated with PEF, a modified 25 g electrode was used to deliver the specialized PEF treatments at a reduced clinical dose. Ten days post-treatment, tumors were harvested and processed for flow cytometry (Table 4).

TABLE 4

Tetramer Antibody Panel

| Marker | Clone | Fluorochrome | Dilution |
|---|---|---|---|
| Viakrome 638 | — | APC | 1:1000 |
| CD45 | 30-F11 | APC-Cy7 | 1:400 |
| CD3 | 17A2 | PE-Cy7 | 1:400 |
| CD4 | RM4-5 | PerCP/Cy5.5 | 1:400 |

TABLE 4-continued

| Tetramer Antibody Panel | | | |
|---|---|---|---|
| Marker | Clone | Fluorochrome | Dilution |
| CD8 | KT15 | FITC | 1:10 |
| SIINFEKL Tetramer | H2Kb | PE | 1:10 |
| Fc Block (Cd16/32) | — | — | 1:200 |

Figure 22A:
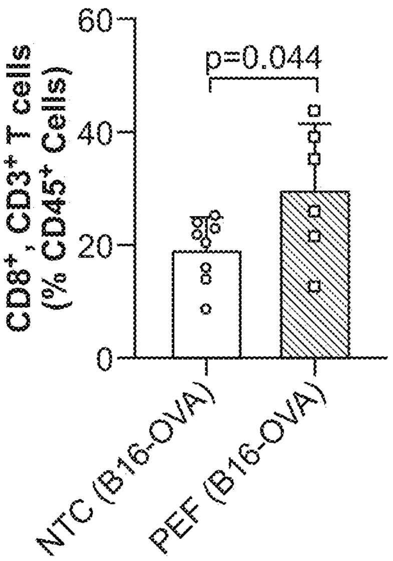
FIGS. 22A-22B illustrate flow cytometry results.
Figure 22B:
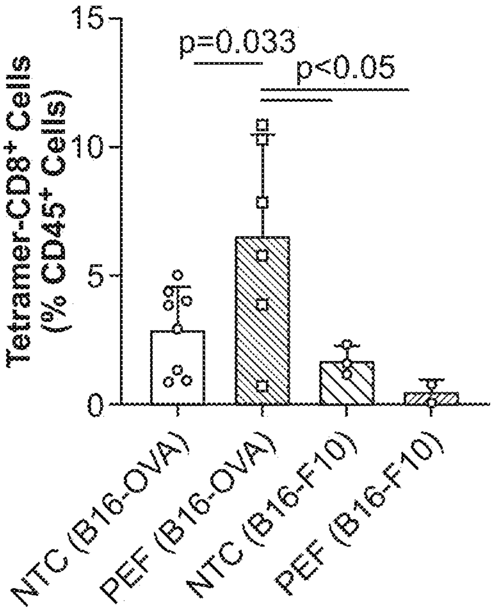

Results: Flow cytometry demonstrated that the frequencies of CD8+ T cells was significantly increased in tumor directly treated with PEF as compared to the NTC (FIG. 22A). To quantify the fraction of tumor specific T cells within the immune infiltrate, a tetramer complex was employed comprising H2-Kb MHC class I molecules bound to the OVA peptide, SIINFEKL. B16-OVA tumors directly treated with PEF had a 125% (p=0.03) increase in OVA-specific CD8+ T cells as compared to B16-OVA tumors in the NTC group (FIG. 22B). The percentage of all CD45+ cells that were positive for the CD8+ tetramer was increased (p=0.05) relative to PEF treated and NTC B16-F10 negative controls.

Conclusions: Local treatment with the specialized PEF generates tumor antigen release in an immunocompetent manner that allows for clonal expansion of tumor specific T cell. Further, the specialized PEF treatment increases CD8 T-cell infiltration to enhance the immunogenicity of cold tumors. Together, local treatment with the specialized PEF provides a tumor specific immune response that produces a robust abscopal effect offering a systemic outcome from a focal therapy.

Example 2: Focal Treatment of Early Stage NSCLC Using Specialized Pulsed Electric Fields: Safety and 30-Day Results from the INCITE ES Study Objectives: To evaluate the safety and initial feasibility of specialized pulsed electric field (PEF) treatment of Non-small Cell Lung Cancer (NSCLC) tumors prior to surgical resection using a PEF system to deliver energy to soft tissue.

Summary: Early-stage NSCLCs are generally not very sensitive to chemotherapy and are treated through surgical resection with curative intent when possible. Additional treatment will be a specialized non-thermal focal ablation modality that employs high frequency electric pulses to destabilize the cell membrane and drive cellular death. Compared to conventional ablative modalities used in soft tissue (e.g. radio-frequency, microwave, cryotherapy), PEF ablation has several potential benefits including an improved safety profile and ability to treat lesions near critical structures due to the preservation of the surrounding architecture including vessels, lymphatics and the extracellular matrix. Further, cell death induced by the specialized PEF delivery leads to enhanced efficacy through stimulation of the body's natural immune responses. As opposed to thermal ablative mechanisms, the non-thermal cell death induced by the specialized PEF releases a greater pool of antigens from the tumor which are accessible to cells of the immune system. Additionally, limited encapsulation and scarring of the treatment area allows better access to these antigens and the tumor itself for the immune cells.

Methods: In this treat and resect study, the specialized PEF energy is delivered via either an endoluminal (bronchoscopic) or percutaneous approach to a solitary, operable, NSCLC lesion prior to surgical resection. Patient population includes adult patients with suspected or confirmed NSCLC 8th ed. Stage IA2, IA3 or IB (>1 to ≤4 cm solitary lesion), lesions that are notable for higher rates of recurrence. Subjects are surgical candidates and have not received treatment for their tumor in the last two years. Computed tomography (CT) is performed prior to PEF delivery and prior to surgical resection. Safety is assessed by evaluation of device and/or procedure-related serious adverse events (SAEs) from the initial PEF delivery through surgical resection. Safety is also assessed through gross and histologic assessment of the resected specimen including effects upon any adjacent bronchi and vasculature. Changes to tumor size, planned surgical approach as consequence of the PEF procedure, 30-day surgical mortality, and percentage of surgical complications due to PEF delivery is also assessed. Clinical utility is evaluated by the assessment of the treatment zone from the resected specimen. Technical success of the PEF procedure is defined and evaluated as the frequency with which clinician could access the tumor and deliver PEF energy. Further, assessment of the immune response comparing pre-treatment samples with post-treatment samples from blood, BAL fluid (if the procedure was performed endoluminally) and tumor tissue is also evaluated.

Preliminary Results: Specialized PEF delivery was successfully performed on all four subjects (mean±standard deviation age 65.0±7.4 years, 50% male), including one lesion which abutted the plural surface an done lesion which abutted a major fissure. Three of the four procedures were completed percutaneously. A single PEF treatment was delivered in each subject, resulting in the longest diameter of the tumor being reduced by 0.7±3.6% as measured prior to the surgical resection. No changes to the planned surgical approach or surgical complications have been observed and no device or PEF procedure related adverse events have been observed from the initial PEF delivery through surgical resection (19-21 days later). Preliminary results indicated a change in immune response within the tumor at the time of resection when compared to pre-treatment tumor tissue samples, including an increase in PD-L1 expression in tumor cells and an increase in CD8+/CD4+ inflammatory cells in the treated area.

Figure 23A:
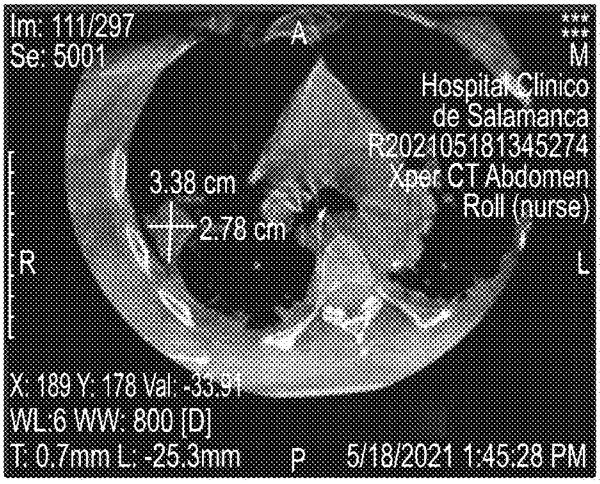
FIGS. 23A-23B provides a CT image of the chest with a 3.4 cm lesion prior to PEF delivery (FIG. 23A) and same lesion prior to surgery measuring 2.8 cm in longest diameter (FIG. 23B).
Figure 23B:
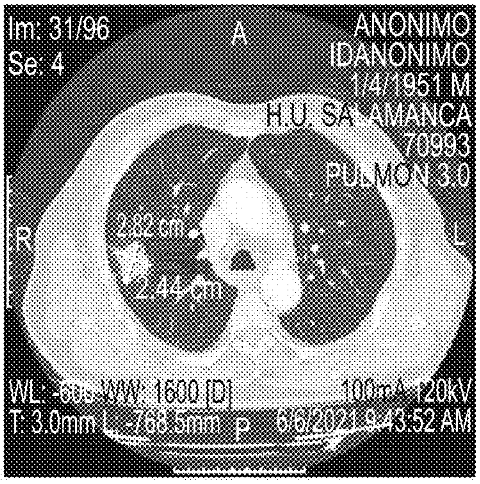
Figure 23C:
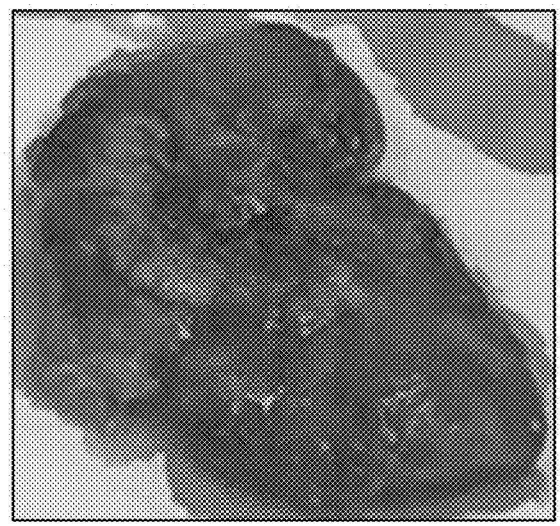
FIGS. 23C-23D provide a gross section of resected tumor 20 days after PEF delivery (FIG. 23C) and corresponding Hematoxylin & Eosin (H&E) (FIG. 23D).
Figure 23D:
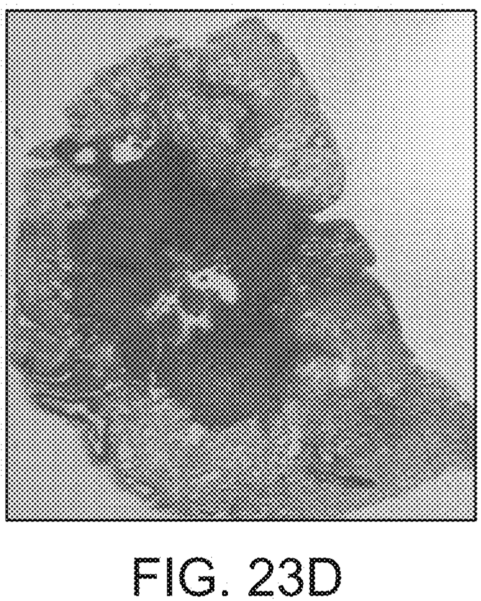
Figure 24:
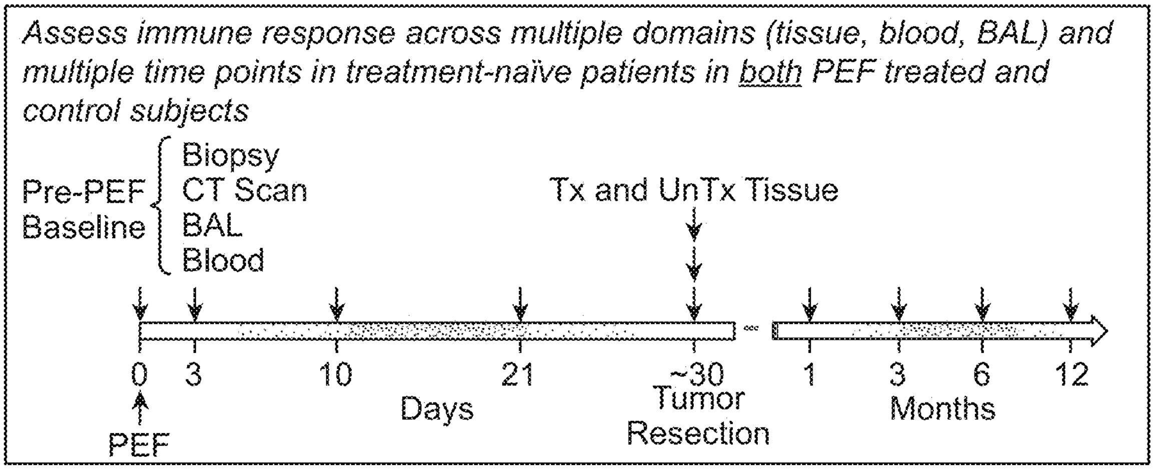
FIG. 24 illustrates an assessment schedule.
Figure 25:
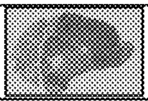
FIG. 25 provides a table of H&E and immunohistochemistry (IHC) performed.
Figure 25:
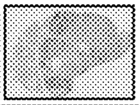
Figure 25:
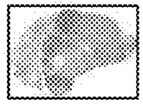
Figure 25:
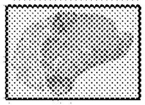
Figure 25:
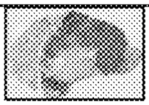
Figure 25:
Figures 26, 27:
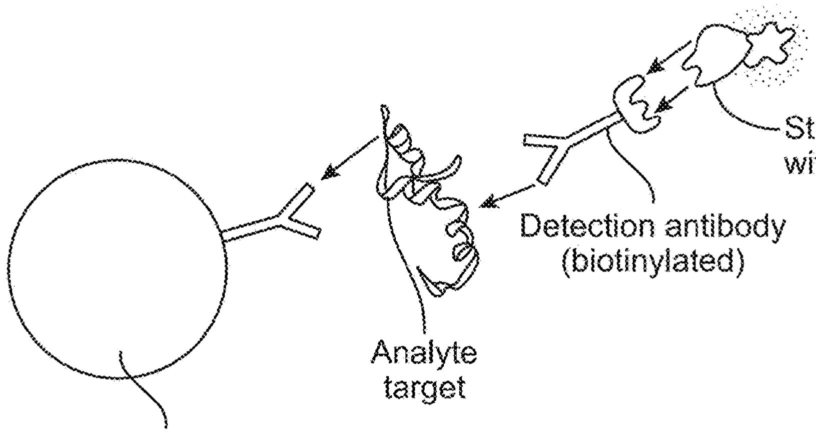
FIG. 26 illustrates a Luminex Multiplex 71-plex panel.
FIG. 27 illustrates baseline characteristics and treatment details.

Results: Enrollment currently includes 26 subjects (21—Treatment Group and 5—Control Group) with mean age 67 years (SD 5.7 years) and 80% of whom are male. A single PEF treatment (refined dose) was successfully performed in all 21 subjects, including one lesion which abutted the pleural surface and one lesion which abutted a major fissure. A single PEF treatment was delivered in at least each of the first four subjects, resulting in the diameter of the tumor being reduced by 14±7%, as measured prior to the surgical resection. FIGS. 23A-23D provide CT images of the chest with a (1) 3.4 cm lesion prior to PEF delivery (FIG. 23A); (2) same lesion prior to surgery measuring 2.8 cm in longest diameter (FIG. 23B); (3) Gross section of resected tumor 20 days after PEF delivery (FIG. 23C); and (4) corresponding Hematoxylin & Eosin (H&E) (FIG. 23D). The immune response was assessed by comparing pre- and post-treatment blood, BAL samples, and via transcriptomic changes in tumor tissue per the schedule illustrated in FIG. 24. FIG. 25 provides a table of H&E and immunohistochemistry (IHC) performed. In addition, flow cytometry, ssRNAseq (Rhapsody™) and Luminex Multiplex 71-plex panel (FIG. 26) was performed. FIG. 27 illustrates baseline characteristics and treatment details.

Treatment was successfully performed in all 27 subjects (technical success=100%). No changes to the planned surgical approach or surgical complications have been observed and no device or PEF procedure related adverse events have been observed from the initial PEF delivery through surgical resection (19-21 days later). Preliminary results indicate a change in immune response within the tumor at the time of resection when compared to pre-treatment tumor tissue samples, including an increase in PD-L1 expression in tumor cells and CD8+/CD4+ T cells ratio near the treatment zone, with a higher number of CD8+ T cells interacting with tumor cells. An increase in cytotoxic CD8+ T-cells was found interacting with tumor cells in tumor 'islands' and an increase in CD4+ helper T-cells were observed outside tumor 'islands'. The lesion, comprising a treatment zone (cellular depletion zone), and surrounding non-treated tissue in the resected specimen was assessed. The Cellular Depletion Zone (CDZ) is a region that is primarily devoid of cancerous cells. The CDZ is visible on gross dissection and is consistently identified with PanCK stain. In this study, the minimum CDZ Dimension±SD, at 20±3 days (n=8) was D1 (longest dimension)=0.9±0.3 cm and D2 (perpendicular to D1)=0.6±0.3 cm. Changes in tumor size were assessed by radiographic assessment.

Figure 28:
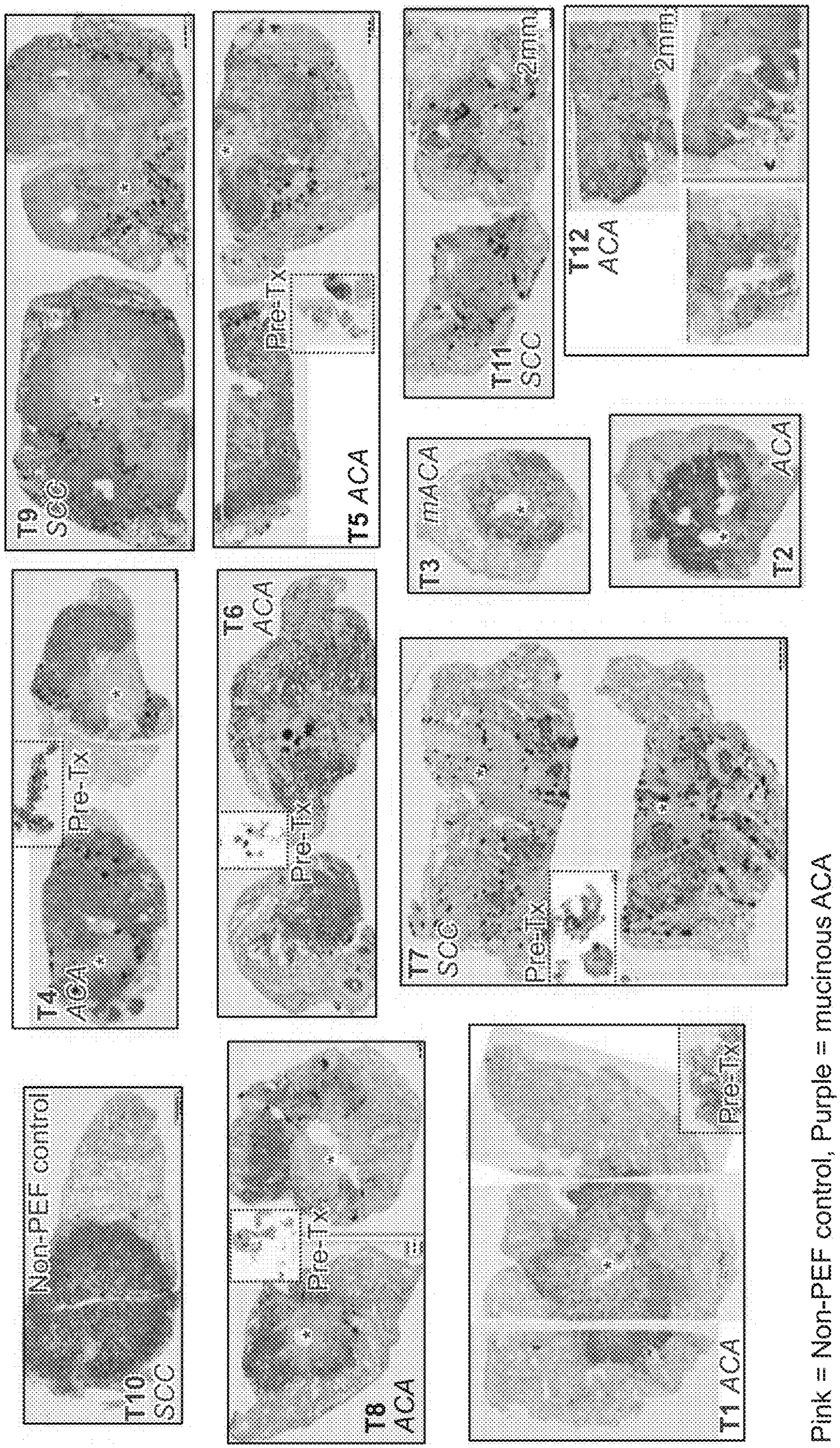
FIG. 28 illustrates a variety of tissue samples having tertiary lymphoid structures.

It may be appreciated that, excluding 1 mucinous adenocarcinoma and the control, all tumors treated with the specialized PEF energy had multiple Tertiary Lymphoid Structures (TLS). TLS are organized aggregates of immune cells that form postnatally nonlymphoid tissues. TLS are not found under physiological conditions but arise in the context of chronic inflammation, such as in autoimmune disease, chronic infection and cancer. In the setting of tumors, TLS facilitate the influx of immune cells into the tumor site and therefore are a means of improving anti-cancer immunity and favorable treatment response to immunotherapy in patients. Presence of TLS in tumors appear to correlate with better prognosis and clinical outcome. Lymphoid aggregates and TLS have been consistently observed near the periphery of the PEF treated tumors. FIG. 28 illustrates a variety of tissue samples having TLS (dark spots).

Figure 29A:
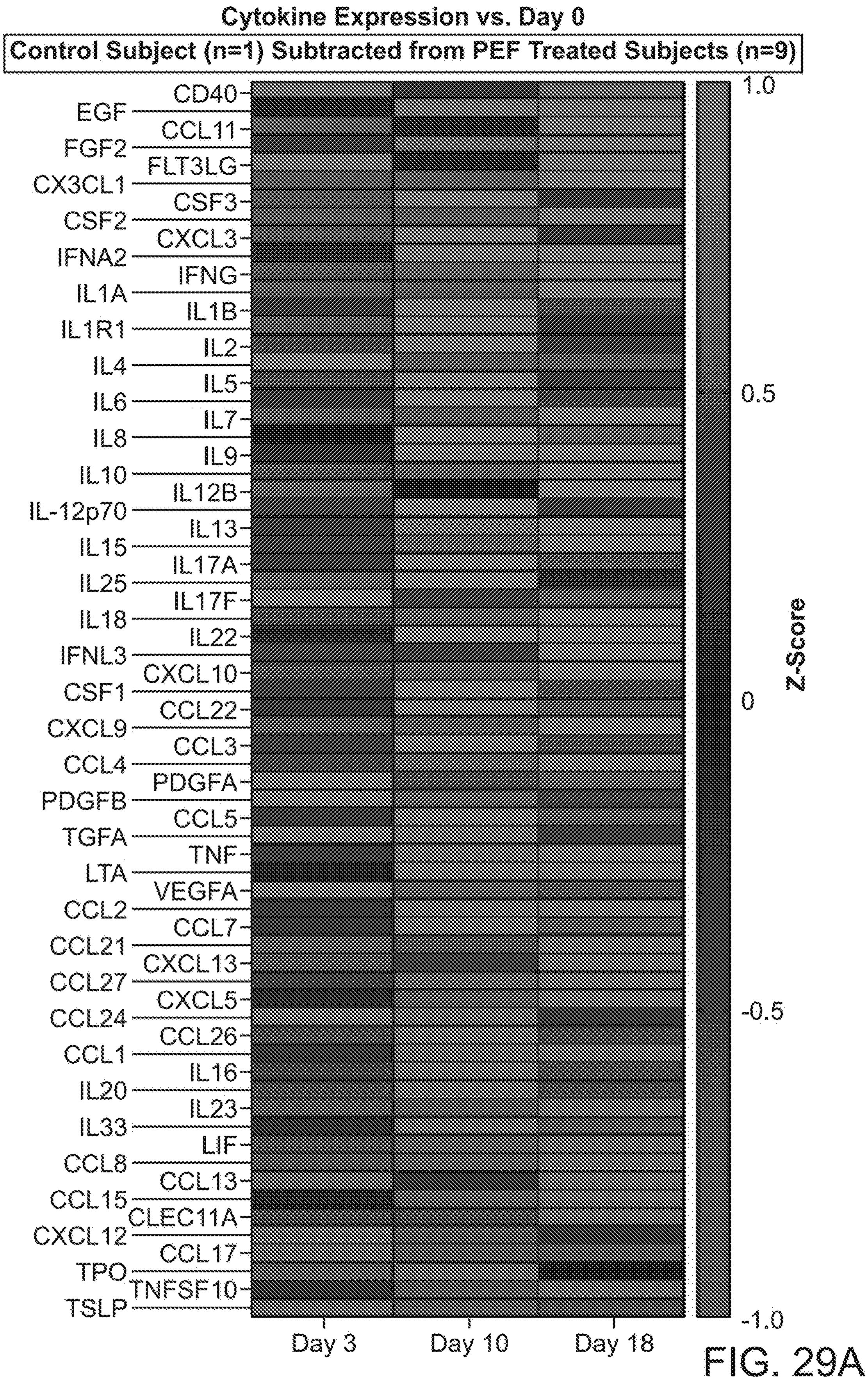
FIGS. 29A-29B illustrate the results of a preliminary serum cytokine analysis.
Figure 29B:
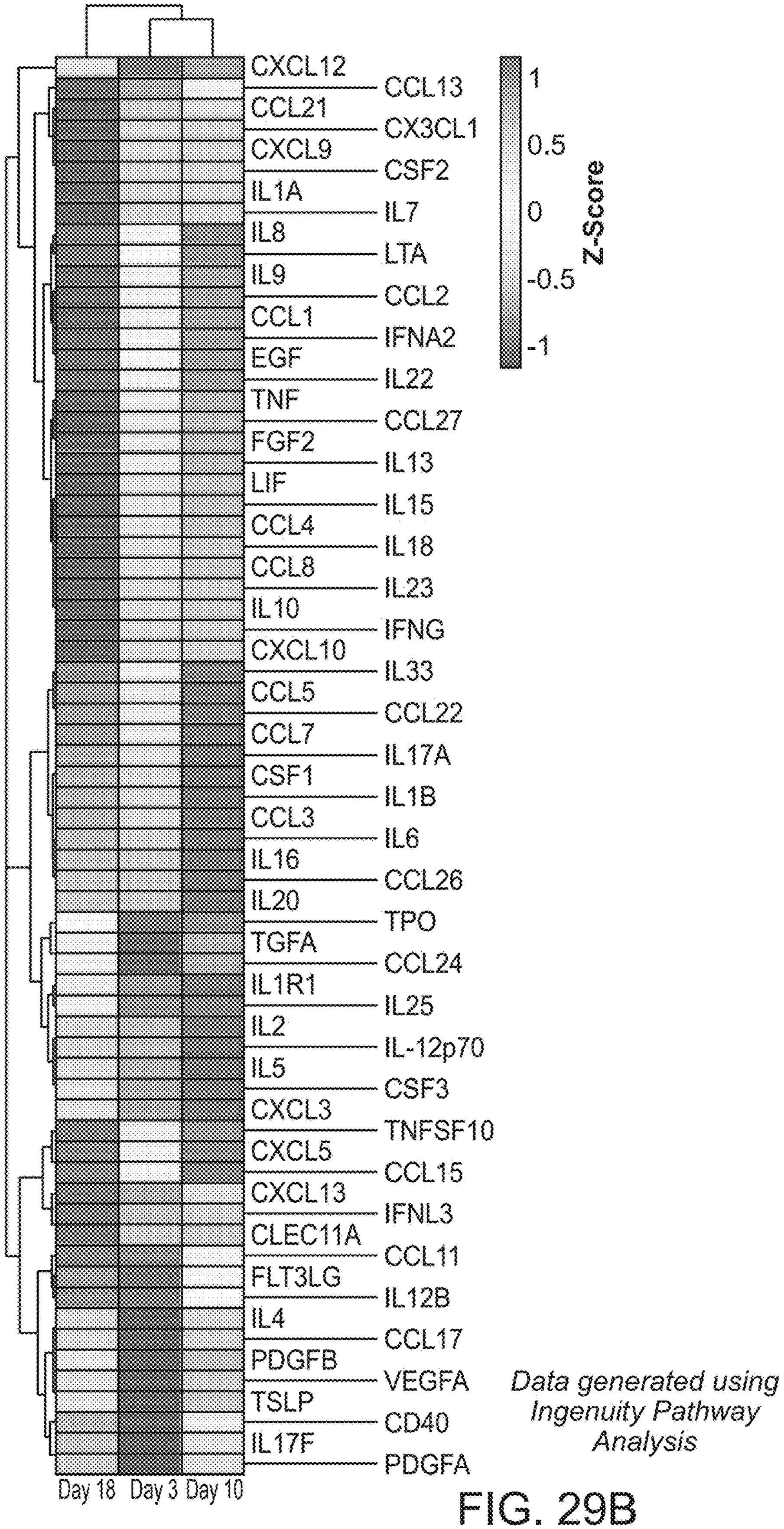

Preliminary Serum Cytokine Analysis (Day 0 to 18) has shown that pathways influenced by PEF include upregulation of lymphoid pathways (e.g., formation and growth of lymphoid organs) and downregulation of regulatory T lymphocytes. FIGS. 29A-29B illustrate the results of the preliminary serum cytokine analysis, namely the expression of various cytokines on Day 03, Day 10, and Day 18.

This initial case series demonstrated the feasibility of delivering the specialized PEF energy with a single electrode in NSCLC tumors. No PEF-related adverse events have been observed, and treatment near adjacent critical structures, including lesions on the pleural surface and major fissure was feasible and without impact on the planned surgical resection. Preliminary analysis of the INCITE ES data illustrates impact of the specialized PEF energy on the immune system (innate and adaptive immune response).

Combination with Immunotherapy

In the last decade, a paradigm shift has occurred in the understanding of the relationship between the immune system, cancer development, and subsequent disease progression. Immunoevasion of malignant cells, escaping detection by the immune system, is now recognized as a cornerstone of tumor development. Tumors invoke a complex network of immune suppression, or immunological pressure, making it difficult for immune effectors to mount a meaningful anti-tumor response. Recently, a tremendous amount of research has investigated the immunosuppressive networks dictated by the tumor microenviroment (TME). One of the most important discoveries in oncology has been understanding the role of immune checkpoints in cancer. Immune checkpoints are inhibitory or stimulatory molecules present on the surface of T cells and antigen-presenting cells (APCs), whose direct interaction modulate the duration and response of a T cell against a foreign body. This is particularly important for maintaining self-tolerance, as it prevents T cells from damaging healthy tissues and creating an autoimmune response.

In the context of cancer, tumor cells may upregulate immune checkpoints to bind to partner receptors on T cells and evade detection. One such immune checkpoint, programmed cell death protein 1 (PD-1) and its ligand PD-L1, has been identified as a significant regulator of immune evasion in numerous cancers. PD1 is a transmembrane protein that is transcriptionally upregulated in activated T cells, B cells and myeloid cells. Therefore, activated T cells that are infiltrating a tumor by an inflammatory response of the immune system often express PD-1 on their surface. PD-L1 is its ligand and it is found on some tumor cells, such as a variety of head and neck carcinomas, lung cancer and melanoma, to name a few. When PD-1 is bound to PD-L1, it prevents the T cells from killing the tumor cell, inducing T cell suppression upon their interaction. Specifically, the PD-1/PD-L1 interaction has been found to mediate T cell immune suppression through the following mechanisms: induce apoptosis in activated T cells, facilitate T cell anergy and exhaustion, enhance the immunosuppression of regulatory T cells (Tregs), limit T cell proliferation, and restrain T cell activation and production of interleukin-2 (IL-2).

Recently, antibodies targeting the PD-1/PD-L1 interaction (Nivolumab, Pembrolizumab, Atezolizumab, Durvalumab) have been FDA approved. For example, Nivolumab is a human immunoglobulin G4 (IgG4) monoclonal antibody that binds to the PD-1 receptor and blocks its interaction with PD-L1, releasing the PD-1 pathway-mediated inhibition of the immune response. This results in decreased tumor growth. Atezolizumab is a fully humanized, engineered monoclonal antibody of IgG1 isotype against PD-L1. Thus, Atezolizumab blocks the interaction of PD-L1 with PD-1. While promising, these drugs have limited efficacy as monotherapies. For example, in non-small-cell-lung-cancer (NSCLC), e.g. any type of epithelial lung cancer other than small cell lung cancer (SCLC), only 20% of patients achieve an objective clinical response to PD-1 blockade. Further, for the patients that do respond, the anti-tumor response is transient, as the tumor develops drug resistance. This low response rate is due to a combination of factors that include PD-L1 expression and the fraction of tumor immune cell infiltrate.

A tumor that is PD-L1 negative and has a low tumor immune cell infiltrate is known as a "cold" tumor. A tumor that is PD-L1 positive and has a high tumor immune cell infiltrate is known as a "hot" tumor. Patients that have cold tumors will be unresponsive to the checkpoint therapy because the PD-1/PD-L1 interaction that it is designed to inhibit is not present. Patients that have hot tumors, as mentioned in the latter, often develop resistance to the therapy over time. This is because the tumor cells that express PD-L1 are eliminated due to blocking of the interaction with PD-1. The remaining tumor cells are a more resistant cancer clone population which are left behind.

Therefore, improved treatments are desired, such as to increase the number of patients that are responsive to immunotherapy and to increase the clinical response of such patients. Such treatments should be safe, effective, and lead to improved outcomes. Combining immunotherapy with the specialized PEF energy described herein meets these objectives.

The devices, systems and methods described herein utilize specialized pulsed electric field energy to treat patients in a manner which utilizes aspects of the immune system, such as aspects of the immune checkpoint system. In some instances, improved outcomes in cancer immunotherapy patients are achieved, particularly for patients that have limited response to some immunotherapy treatments or acquired resistance over time. In some embodiments, the PD-1/PD-L1 interaction is targeted for treatment. In other instances, other pathways of the immune system are involved in the treatment, additionally or independent of PD-1/PD-L1.

Figure 30:
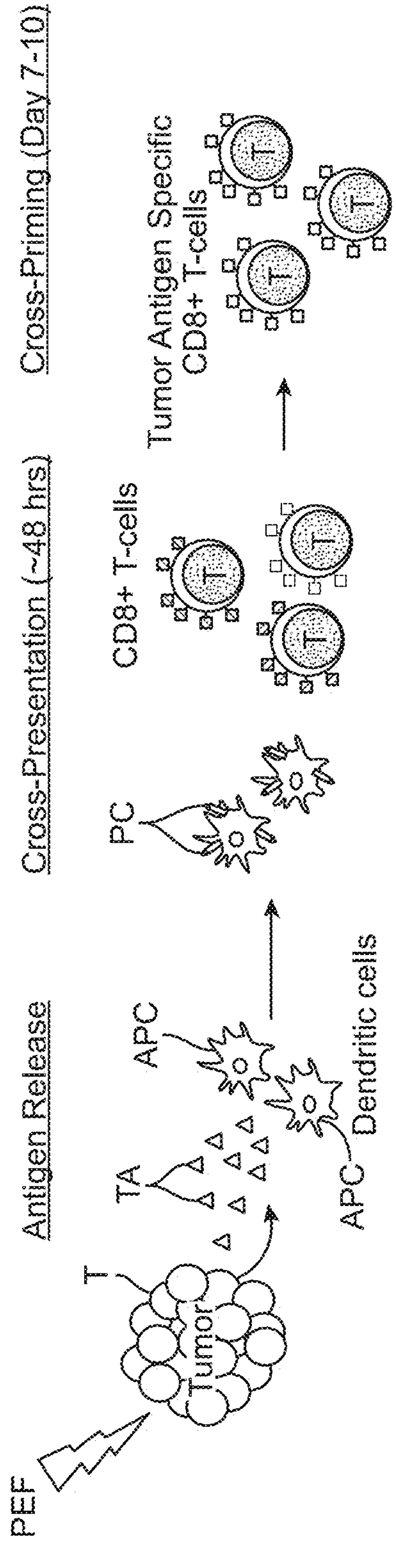
FIG. 30 shows a tumor treated with PEF energy, wherein the energy kills the cells in a way that is meaningful to the immune system.

In some embodiments, specialized pulsed electric field (PEF) energy is delivered to a target treatment area, such as a tumor or malignant tissue, to cause the destruction of the tissue. The specialized PEF energy is an energy directed focal therapy that relies on the application of brief, high-amplitude, pulsed energy ultimately leading to a cascade of local events including cell death, inflammatory signaling, and the generation of viable antigen presentation within the tumor microenvironment. Specifically, in some instances the specialized PEF energy promotes the release of tumor antigen, which when taken up via macropincytosis by dendritic cells (DCs) can process them into a peptide-MHC class I complex for cross-presentation to T cells. Once the antigen is cross-presented, a cytotoxic T cell that has a T cell receptor that recognizes this epitope of the peptide-MHC class I complex will expand to mount an anti-tumor response (cross-priming), as illustrated in FIG. 30. In particular, FIG. 30 shows a tumor T treated with specialized PEF energy, wherein the energy kills the cells in a way that is meaningful to the immune system (e.g. immunogenic cell death). Here, the treatment with specialized PEF energy promotes the release of tumor antigen TA from the tumor T. Antigen Presenting Cells (APCs), such as dendritic cells internalize the antigen and process it into a peptide complex PC that is recognized by the T cell receptor of T cells (e.g. CD8+ T-cells). T cells have unique T cell receptors that recognize a single peptide epitope. Once activated, they clonally expand to mount an immune response against that specific target (cross-priming). Importantly, this feature of PEF therapy increases the fraction of T cells in the tumor immune infiltrate to yield more beneficial outcomes.

Figure 31:
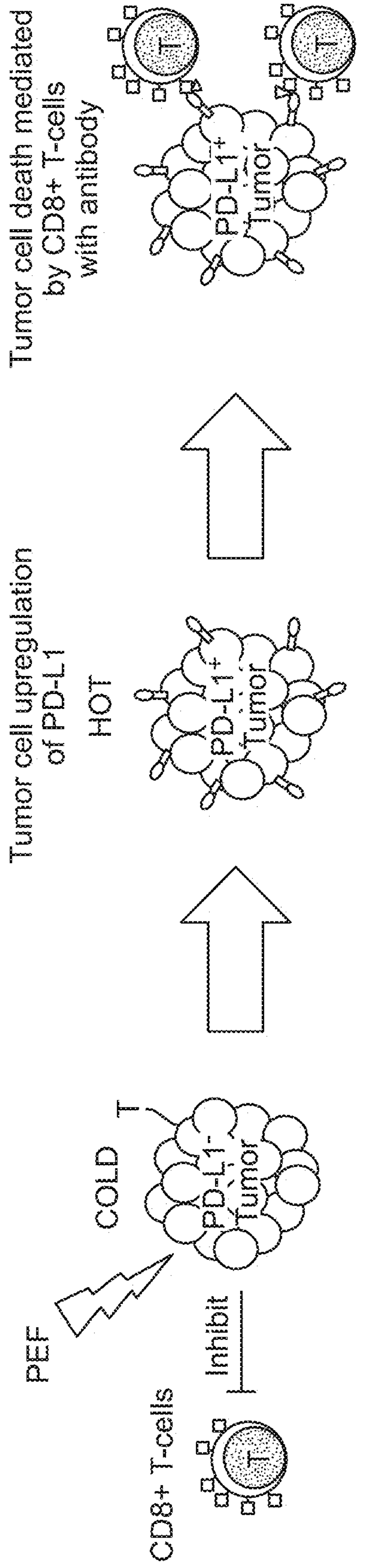
FIG. 31 illustrates PEF energy delivered to a target treatment area, such as including a tumor, in a manner that promotes the upregulation of PD-L1 by the tumor cells.

In some embodiments, the specialized PEF energy is delivered to a target treatment area, such as including a tumor, in a manner that promotes the upregulation of PD-L1 by the tumor cells, as illustrated in FIG. 31. In this embodiment, the tumor T becomes stressed due to the inflammatory insult induced by the PEF energy which transcriptionally activates PD-L1. It may be appreciated that activation of PD-L1 may typically be considered detrimental in the treatment of tumors in that such upregulation of PD-L1 increases the immunosuppressive interaction of PD-1/PD-L1 thereby inhibiting T cells (e.g. CD8+ T cells). However, such upregulation has the capability of making cold tumors (i.e. a tumor that is PD-L1 negative and has a low tumor immune cell infiltrate) PD-L1 positive and thereby hot. A hot tumor is PD-L1 positive and has a high tumor immune cell infiltrate. Patients that have hot tumors will be responsive to checkpoint therapy targeting the PD-1/PD-L1 interaction. Thus, patients that have cold tumors, either originally or by developed resistance, can be transformed into having hot tumors with appropriate treatment by PEF energy.

Thus, in some embodiments, an antibody targeting PD-1 ((αPD-1) is delivered to the patient, either in combination with the PEF energy or at a predetermined time or times in relation to the PEF energy. The αPD-1 interferes with the PD-1/PD-L1 interaction, allowing the tumor cells to be identified and killed by the T cells. Thus, the transformed patient is now responsive to immunotherapy such as αPD-1 therapy.

The effects of the PEF therapy and checkpoint inhibition on tumor growth rate, survival, and the expression of pro/anti-inflammatory cytokines was studied in two syngeneic models of mammary carcinoma: EMT6 and 4T-1 tumor bearing Balb/c mice. Since murine models of cancer have varying levels of immunogenicity (i.e., the ability of the transplanted cancer to invoke an immune response), it was desired to validate therapy across multiple tumor models to accurately determine immunologic outcomes.

In the EMT6 tumor model, a combinatorial therapeutic protocol was undertaken that included both specialized PEF therapy and checkpoint inhibition (delivery of αPD-1), known as "PEF+αPD-1". This was compared to PEF delivery alone and αPD-1 alone. Each cohort had 10-12 subjects. In this tumor model, each female mouse was challenged with EMT6 cells in the 4th/5th mammary fat (left side of the animal). Eight days after the challenge, tumors (e.g. 4-5 mm in length) were directly treated with PEF energy. In one embodiment, the PEF energy waveform was comprised of plurality of biphasic pulses grouped into packets, wherein each packet had 40 cycles (i.e. biphasic pulses) each separated by 1000 microsecond delays. In this embodiment, the treatment included 100 packets, each packet separated by a 3 second inter-packet delay. In this embodiment, the voltage was 2500V and the fundamental frequency was 400 kHz. In some instances, the mouse was administered αPD-1 once a week starting on either the day of initial challenge with EMT6 cells or on the day of specialized PEF energy delivery. In other instances, the mouse was administered αPD-1 multiple times a week starting on the day of initial challenge with EMT6 cells or on the day of PEF energy delivery. Three days after PEF treatment, all animals were challenged with EMT6 cells in the contralateral side (4th/5th mammary fat on the right side of the animal). Tumor sizes were measured multiple times per week and were allowed to grow until a tumor reached a predetermined maximum allowable volume.

Figure 32:
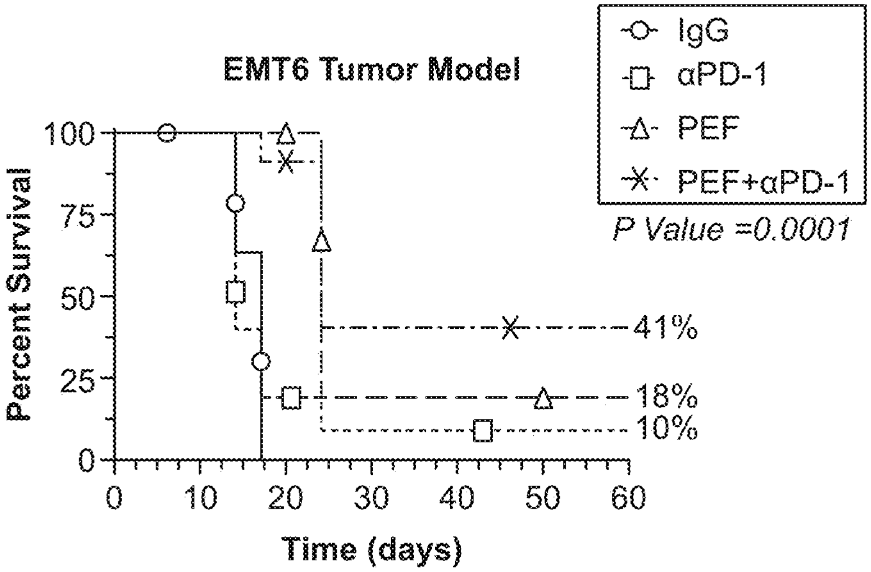
FIG. 32 provides a Kaplan-Myer Plot depicting survival outcomes in an EMT6 tumor model study comparing various treatment protocols.

Directly treated and contralateral tumors in the PEF+αPD-1 cohort experienced significant suppression in tumor growth by 24 days post-treatment compared to all groups. As shown in FIG. 32, in total, 41% of animals treated with PEF+αPD-1 achieved a complete response as compared to 10% of mice for αPD-1 and 18% of mice for PEF monotherapy. Thus, delivery of αPD-1 alone had the lowest response which has similarity to conventional antibody immunotherapy. Delivery of specialized PEF energy alone had an improved response due to the effects of the PEF energy described herein above. The combined delivery of PEF+αPD-1, not only significantly (P value<0.001) improved survival outcomes compared to PEF or αPD-1 monotherapy but the PEF energy and αPD-1 acted together to synergistically create a bolstered anti-tumor response. This outcome was beyond an additive response.

Figure 33:
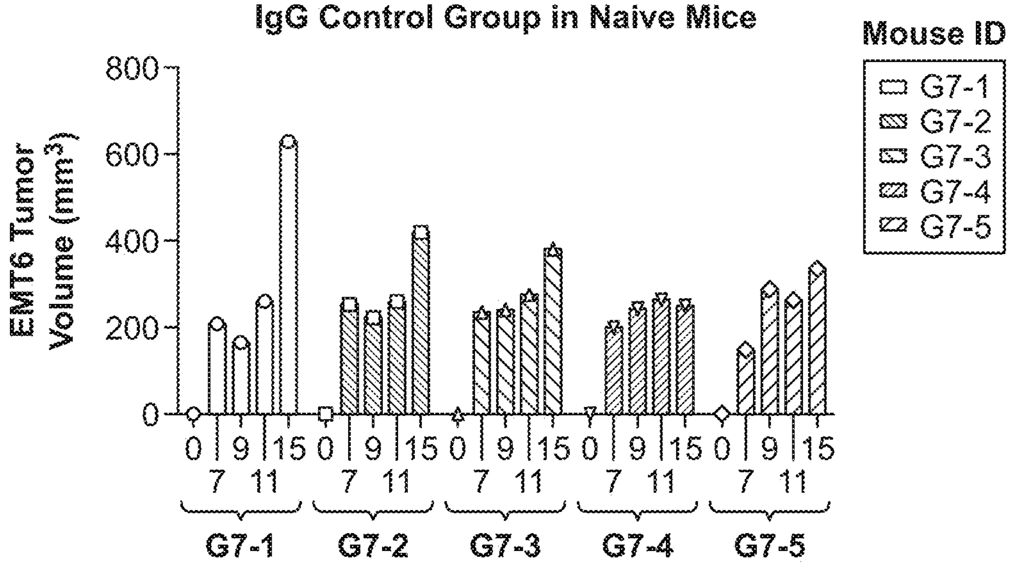
FIG. 33 provides outcome data of a control group for an EMT6 tumor model study.

Mice that achieved complete responses were then re-challenged with EMT6 tumor cells by implanting a new EMT6 tumor. This was to determine if the initial treatment was sufficient to induce longer term immune responses against EMT6 cells in other areas of the body, a phenomenon called the abscopal effect. Assessment of immune system activation was determined by the measurement of lymphocytes (CD8+) in the treated-primary tumor, untreated secondary tumor and peripheral blood. As a control cohort, naïve mice were challenged with EMT6 cells and administered IgG three times per week. FIG. 33 illustrates that all control animals grew tumors. Day 0 marks the day of EMT6 challenge.

Figure 34:
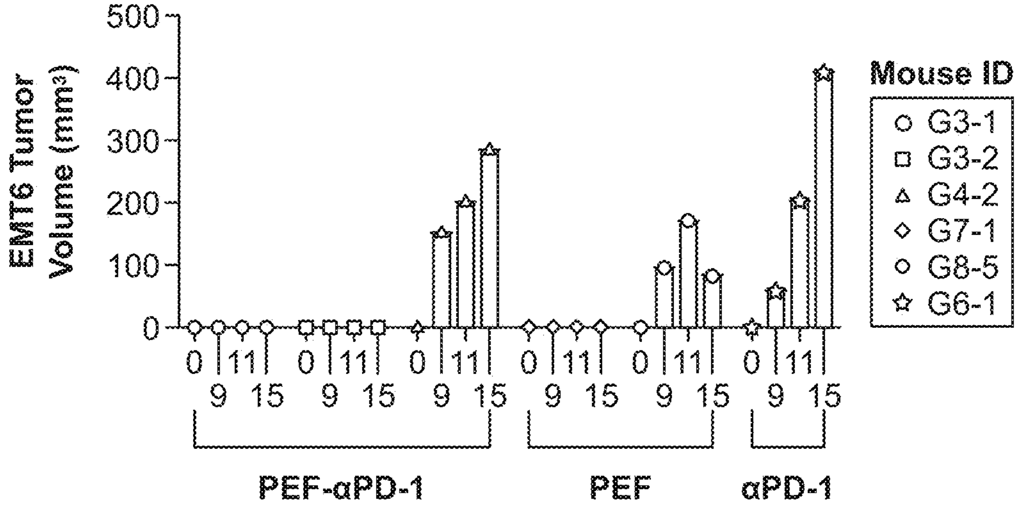
FIG. 34 illustrates the results of three groups (PEF+αPD-1, PEF energy alone and αPD-1 alone) in an EMT6 tumor model rechallenge study.

FIG. 34 illustrates the results of the three groups: PEF+αPD-1, PEF energy alone and αPD-1 alone. The rechallenged mouse that received αPD-1 alone grew a tumor. Of the rechallenged mice that received PEF energy alone, one developed a tumor and one did not. Of the rechallenged mice that received a combination therapy PEF+αPD-1, one grew a tumor and two did not. This data demonstrates that the specialized PEF energy is sufficient to promote long term immunity to a specific cancer subset.

In the 4T-1 tumor model, a more aggressive, metastatic tumor model, a combinatorial therapeutic protocol (PEF+αPD-1) was also utilized. Again, this was compared to specialized PEF delivery alone, αPD-1 alone and a control group. Here, the control group was administered IgG. In this model it was sought to determine the impact of the specialized pulsed electric fields (PEF) and checkpoint inhibition (αPD-1) on directly treated and distant disease and to identify the mechanisms for enhanced response obtained by combinatorial treatment.

Figure 35A:
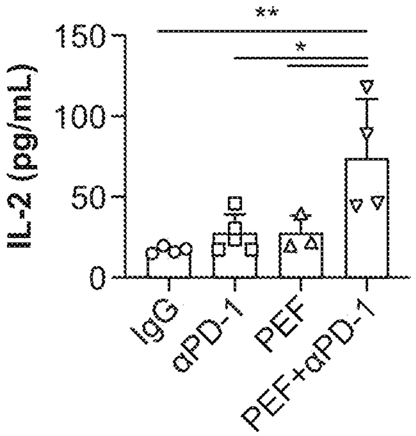
FIGS. 35A-35D illustrate example results of cytokine analysis for a 4T-1 tumor model study.
Figure 35B:
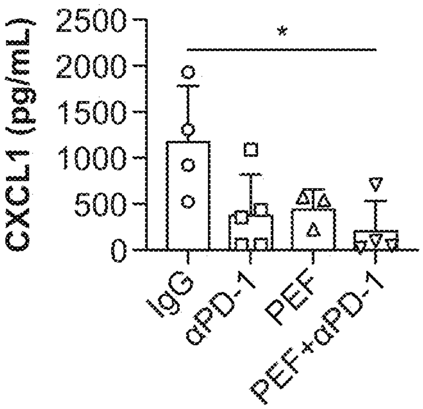
Figure 35C:
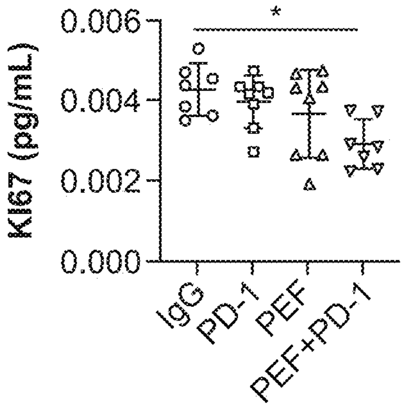
Figure 35D:
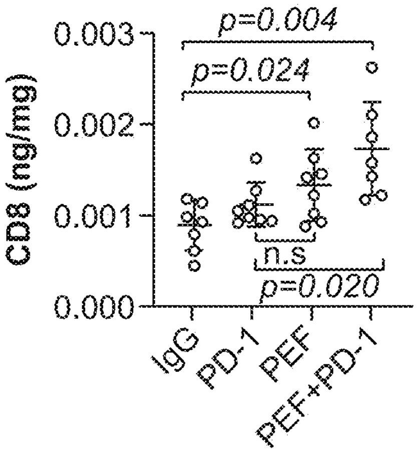

Cytokine analysis was performed on untreated tumors and lung tissue with metastatic disease at 18 days post-treatment. The cytokines analyzed were: A) T-cell activator, IL-2; B) neutrophil recruitment chemokine, CXCL1; C) marker for tumor viability, Ki67; and D) cytotoxic T cells in immune cell infiltrate, CD8. Example results are illustrated in FIGS. 35A-35D. As shown in FIG. 35A, delivery of specialized PEF energy and checkpoint blockade (i.e., PEF+αPD-1) significantly elevated the expression of T-cell activator, IL-2, in untreated tumors, whereas all other biological cohorts (i.e., control, specialized PEF energy only, αPD-1 only) did not. As shown in FIG. 35B, delivery of PEF+αPD-1 significantly decreased the neutrophil recruitment chemokine, CXCL1, in both the tumor and lung compared to IgG control group. As shown in FIG. 35C, a marker for tumor viability (Ki67) was quantified in whole lung tissue via ELISA to characterize the metastatic burden in treated animals. Importantly, only the PEF energy and immunotherapy cohort (i.e., PEF+αPD-1) decreased the total expression of Ki67 in the lungs compared to the IgG control group. As shown in FIG. 35D, cytotoxic T cells in the immune cell infiltrate (CD8) were quantified in whole lung tissue via ELISA. Delivery of PEF energy alone and PEF energy combined with immunotherapy (i.e., PEF+αPD-1) increased the expression of CD8 in the lungs compared to both the IgG control and αPD-1 alone. Taken together, these data suggest the inclusion of specialized PEF into a protocol with a checkpoint inhibitor (PEF+αPD-1) induces a robust systemic anti-tumor response in the 4T-1 "cold" tumor model. Thus, combinatorial treatment alleviated systemic immune suppression.

The devices, systems and methods deliver the specialized PEF energy to the cells with a system that typically includes a specialized energy delivery device, a waveform generator and at least one distinct energy delivery algorithm as described herein above. Additional accessories and equipment may be utilized. The energy delivery device delivers energy provided by the waveform generator according to the at least one distinct energy delivery algorithm. It may be appreciated that, in some embodiments, the energy delivery device also delivers one or more agents, such as antibodies (e.g. αPD-1). However, in other embodiments, the agent(s) are delivered by a separate device, such as by IV, catheter, or needle injection. Optionally, the agent(s) may be delivered both by the energy delivery device and by a separate device. Example embodiments of specialized energy delivery devices are provided herein primarily focused on monopolar energy delivery, however, it may be appreciated that bipolar or multi-polar arrangements may be used.

Figure 36:
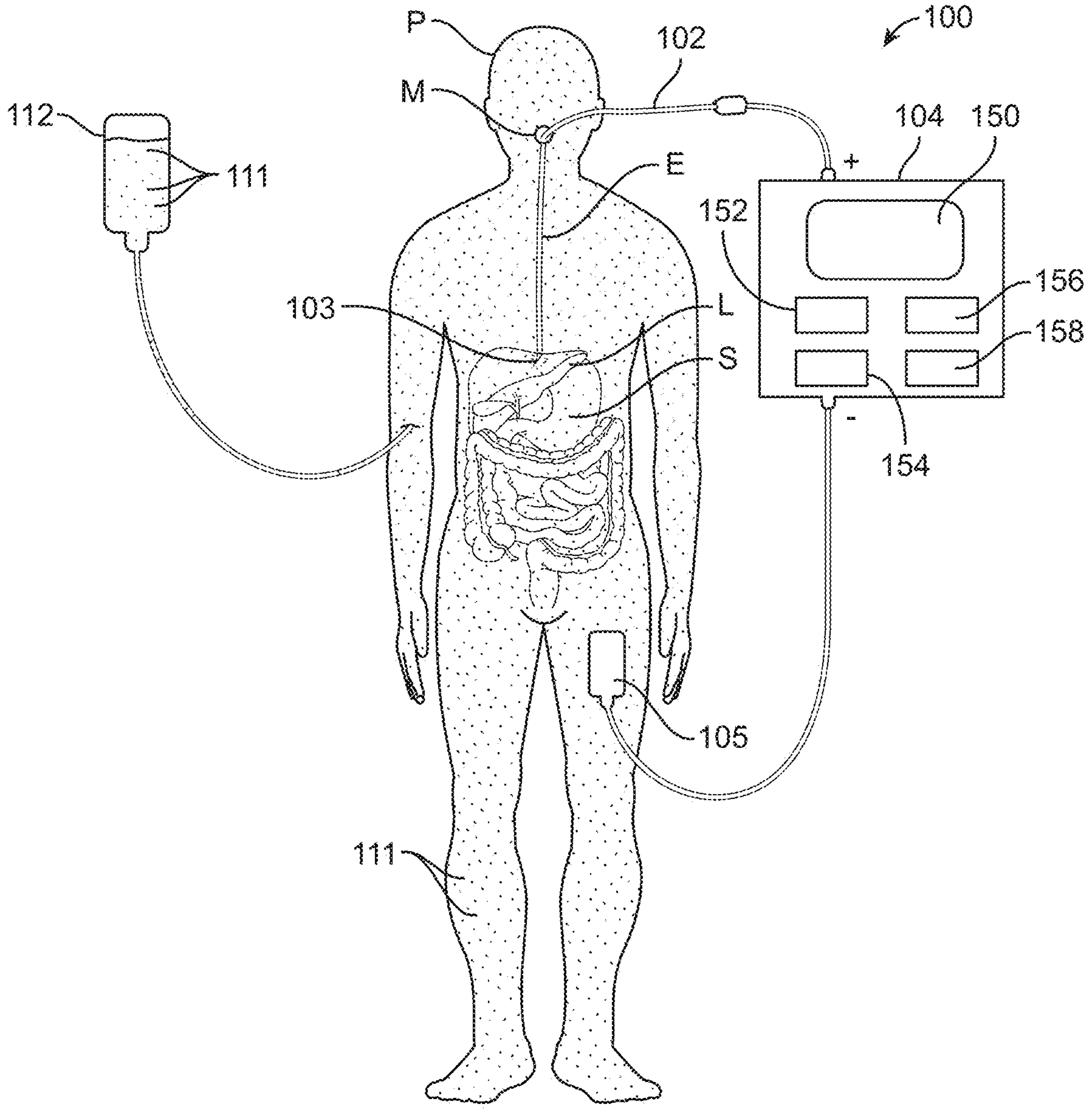
FIG. 36 illustrates an embodiment of a delivery system.

FIG. 36 illustrates an embodiment of an energy delivery system 100 comprising a specialized energy delivery device or instrument 102, a return electrode 140, and a waveform generator 104. In this embodiment, the target tissue is located within a liver L of a patient P. It may be appreciated that target tissue cells may be treated in any location throughout the body, including cells of the digestive system (e.g. mouth, glands, esophagus, stomach, duodenum, jejunum, ileum, intestines, colon, rectum, liver, gall bladder, pancreas, anal canal, etc.), cells of the respiratory system (e.g. nasal cavity, pharynx larynx, trachea, bronchi, lungs, etc.), cells of the urinary system (e.g. kidneys, ureter, bladder, urethra, etc.), cells of the reproductive system (e.g. reproductive organs, ovaries, fallopian tubes, uterus, cervix, vagina, testes, epididymis, vas deferens, seminal vesicles, prostate, glands, penis, scrotum, breasts, etc.), cells of the endocrine system (e.g. pituitary gland, pineal gland, thyroid gland, parathyroid gland, adrenal gland), cells of the circulatory system (e.g heart, arteries, veins, etc.), cells of the lymphatic system (e.g. lymph node, bone marrow, thymus, spleen, etc.), cells of the nervous system (e.g. brain, spinal cord, nerves, ganglia, etc.), cells of the muscular system, and cells of the skin, to name a few.

In this embodiment, the instrument 102 comprises a flexible elongate shaft having a distal end capable of being advanced endoluminally to the target tissue within the liver L. As shown, the distal end of the instrument 102 is advanced through the mouth M, down the esophagus E, into the stomach S wherein it passes through the stomach wall into the liver L. In some embodiments, the distal end has a distal end 103 configured to penetrate the stomach wall and/or the liver L. In other embodiments, a passageway is formed through the stomach wall with the use of a separate instrument which is then removed so that an instrument 102 having an atraumatic tip is able to be passed through the passageway.

In this embodiment, agent 111 is delivered systemically, intravenously with the use of an IV bag 112. This typically disperses the agent throughout the body of the patient P, including to the target tissue within the liver L. It may be appreciated that in other embodiments, the agent 111 is delivered regionally. In such embodiments, the agent 111 may be delivered to the vasculature, upstream of the arterial system that leads to the targeted organ or tissue area. The agent 111 then travel through the downstream arterial circulation into the targeted region. If a bolus injection of the agent 111 is provided, a sudden rush of agent 111 will enter into the targeted tissue. However, if the agent 111 is delivered over time, such as with the use of an infusion pump, a steady, sustained level of agent 111 may be achieved in the targeted tissue. It may be appreciated that in other embodiments, the agent 111 is delivered by direct injection to the targeted tissue. In such embodiments, the injection device is inserted in or near the targeted tissue, such as within the parenchymal tissue of the targeted organ region, and a solution containing the agent is injected. The solution of agent may be permitted a period of time for its distribution through the parenchyma and interstitial spaces to reach an area or volume targeted for transfer. It may be appreciated that any combination of systemic, regional and local delivery may alternatively be used.

The specialized pulsed electric field (PEF) energy is delivered to the target tissue through the distal end of the delivery device 102. The proximal end of the delivery device 102 is electrically connected with the waveform generator 104. In some embodiments, the generator 104 is also connected with an external cardiac monitor (not shown) to allow coordinated delivery of energy with the cardiac signal sensed from the patient P.

In this embodiment, the energy delivery device 102 is designed to be monopolar, wherein the distal end of the instrument 102 has as a delivery electrode and the return electrode 140 is positioned upon the skin outside the body, typically on the thigh (as shown), lower back or back.

The specialized pulsed electric fields (PEFs) are provided by the generator 104 and delivered to the tissue through an energy delivery body 108 placed on, in, or near the targeted tissue area. It may be appreciated that in some embodiments, the energy delivery body 108 is positioned in contact with a conductive substance which is likewise in contact with the targeted tissue. Such solutions may include isotonic or hypertonic solutions. Electric pulses are then delivered through the energy delivery body 108 in the vicinity of the target tissue. These electric pulses are provided by at least one energy delivery algorithm 152. In such embodiments, the algorithm 152 specifies parameters of the signal such as energy amplitude (e.g. voltage) and duration of applied energy, which is comprised of the number of pulses, the pulse widths and the delay between pulses, to name a few. In some embodiments, one or more of the energy delivery bodies are small and tend to dissipate large amount of energy around the electrode. Therefore, an optimal delivery of energy is desired.

In some embodiments, biphasic pulses may be used. In such embodiments, additional parameters may include switch time between polarities in biphasic pulses and dead time between biphasic cycles. A feedback loop based on sensor information and an auto-shutoff specification, and/or the like, may be included. Biphasic waveforms are convenient to reduce muscle stimulation in patients. This is particularly important in the application where slight movement of the energy delivery body can easily result a non-effective therapy. Biphasic waveforms involve rapid change of phases/polarities of the signal to minimize nerve activation during transition between polarity.

The specialized PEF energy may be delivered by a variety of energy delivery devices or instruments 102. Typically, the instrument 102 comprises a flexible elongate shaft having a distal end, capable of being advanced to the target tissue with the body, and at least one energy delivery body 108 disposed near the distal end. The energy delivery body 108 comprises one or more electrodes that delivers the PEF energy to the target tissue. As mentioned previously, in some embodiments the energy delivery device 102 delivers the PEF energy and the agent 111 is delivered by a separate device, such as by IV, catheter, or needle injection. Such delivery of agent 111 may occur at a variety of times in relation to the delivery of PEF energy, such as prior to, during or after. When delivered at a time separate from the PEF energy delivery, such delivery may be separated from the PEF energy delivery by sub-seconds, seconds, minutes, hours, days, weeks, or months.

Figure 37A:
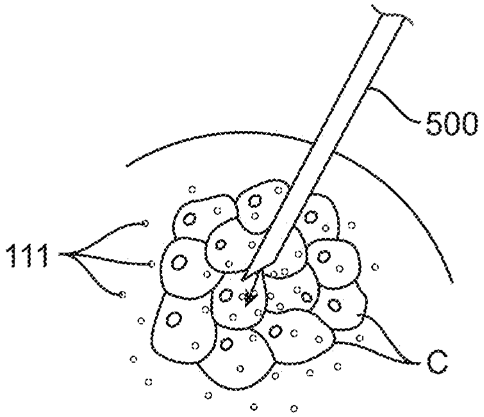
FIG. 37A illustrates direct injection of agent to a target tissue through a needle.
Figure 37B:
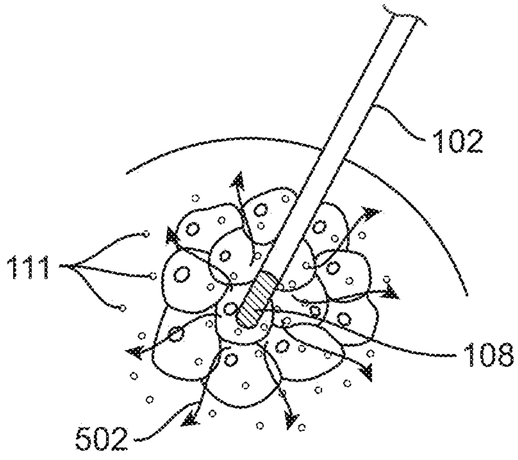
FIG. 37B illustrates delivery of energy from an energy delivery device inserted in place in the needle of FIG. 37A.

FIG. 37A illustrates direct injection of agent 111 to a target tissue through a needle or probe 500. The target tissue is illustrated as cells C (not to scale). The needle or probe 500 is inserted in or near the target tissue so that the injected agent 111 is able to bathe the target tissue. In this embodiment, the probe 500 is then removed and the agent 111 dwells for biodistribution. Referring to FIG. 37B, the distal end of the instrument 102 is then inserted into the target tissue at the desired timepoint so that the energy delivery body 108 is desirably positioned within or near the target tissue. In this embodiment, the energy delivery body 108 is comprised of a single electrode. The specialized PEF energy is then delivered to the target tissue from the energy delivery body 108 as indicated by wavy lines 502. In this embodiment, the PEF energy upregulates PD-L1 in the cells C, among other effects, and the agent 111 comprises αPD-1 which interferes with the PD-1/PD-L1 interaction. This allows T cells within the patient P to identify and kill the targeted cells C in response.

Figure 38A:
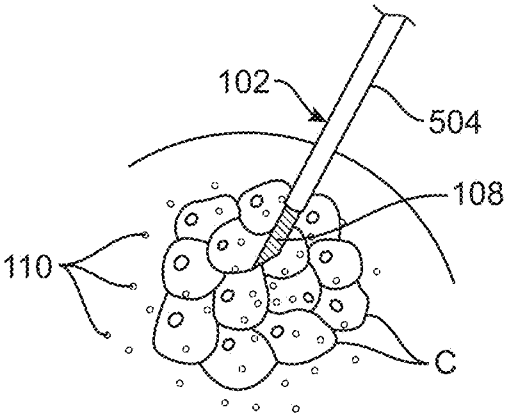
FIG. 38A illustrates direct injection of agent to a target tissue through an energy delivery body.
Figure 38B:
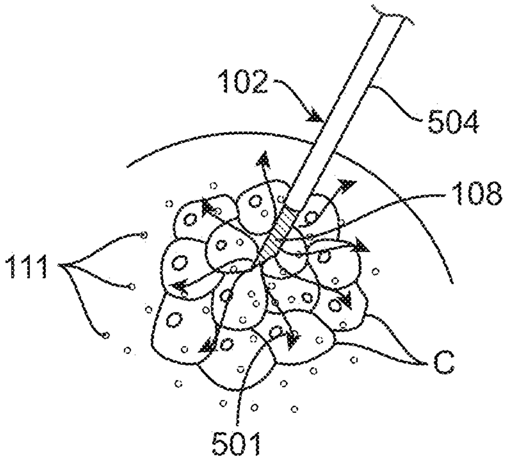
FIG. 38B illustrates delivery of energy from the energy delivery body of FIG. 38A.

In some embodiments, the agent 111 and the energy are delivered close enough in time that the agent 111 is delivered by the energy delivery device or instrument 102. FIGS. 38A-38B illustrate an energy delivery device or instrument 102 having an energy delivery body 108 having a needle shape. The tip of the needle shape is able to penetrate similarly to a needle and deliver agent 111 through its internal lumen. In addition, the energy delivery body 108 is electrically insulated with an insulation layer 504 except for the tip of the needle shape which acts as an electrode. FIG. 38A illustrates direct injection of agent 111 to a target tissue through the energy delivery body 108. Again, the target tissue is illustrated as cells C (not to scale). The tip is inserted in or near the target tissue so that the injected agent 111 is able to bathe the target tissue and optionally dwells for biodistribution. Referring to FIG. 38B, PEF energy is then delivered to the target tissue from the energy delivery body 108 as indicated by wavy lines 501. In this embodiment, the PEF energy upregulates PD-L1 in the cells C, among other effects, and the agent 111 comprises αPD-1 which interferes with the PD-1/PD-L1 interaction. This allows T cells within the patient P to identify and kill the targeted cells C in response.

Figure 39:
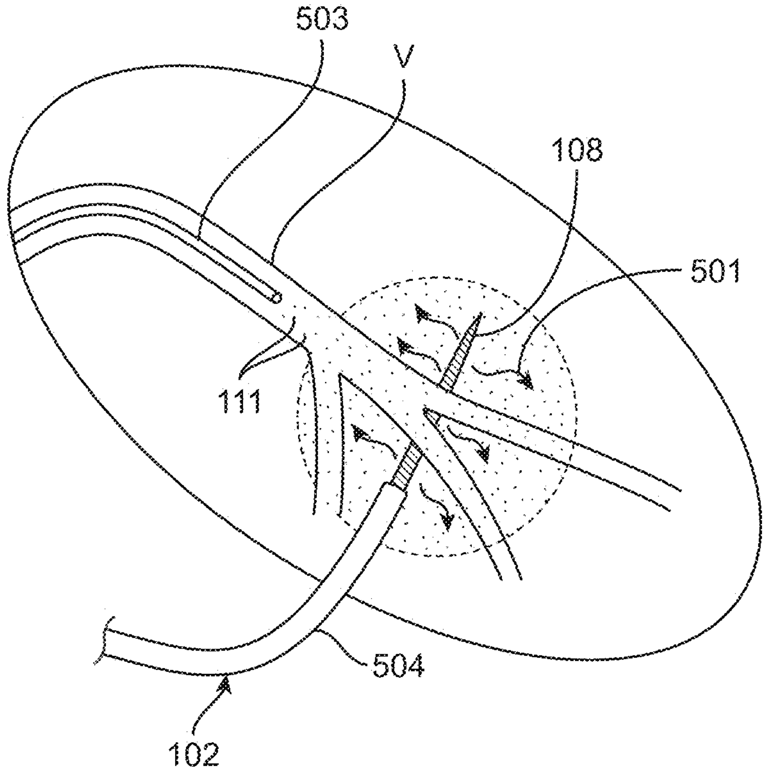
FIG. 39 illustrates agent delivered regionally while energy is delivered locally, and optionally agent is delivered locally as well.

FIG. 39 illustrates agent 111 delivered regionally while energy is delivered locally (and optionally agent 111 is additionally delivered locally). Here, agent 111 is delivered by a separate device, such as a catheter 503 positioned within the vasculature V that feeds the target tissue area. Thus, agent 111 is delivered regionally to the target tissue area. The energy delivery device or instrument 102 is inserted into the target tissue area from a different approach. Here, the instrument 102 comprises an energy delivery body 108 having a needle shape. The tip of the needle shape is able to penetrate similarly to a needle. In some embodiments, agent 111 is able to be delivered through its internal lumen. In this embodiment, the energy delivery body 108 is electrically insulated with an insulation layer 504 except for the tip of the needle shape which acts as an electrode. The tip is inserted in or near the target tissue and PEF energy is then delivered to the target tissue from the energy delivery body 108 as indicated by wavy lines 501. In this embodiment, the PEF energy upregulates PD-L1 in the cells C, among other effects, and the agent 111 comprises αPD-1 which interferes with the PD-1/PD-L1 interaction. This allows T cells within the patient P to identify and kill the targeted cells C in response.

Figure 40:
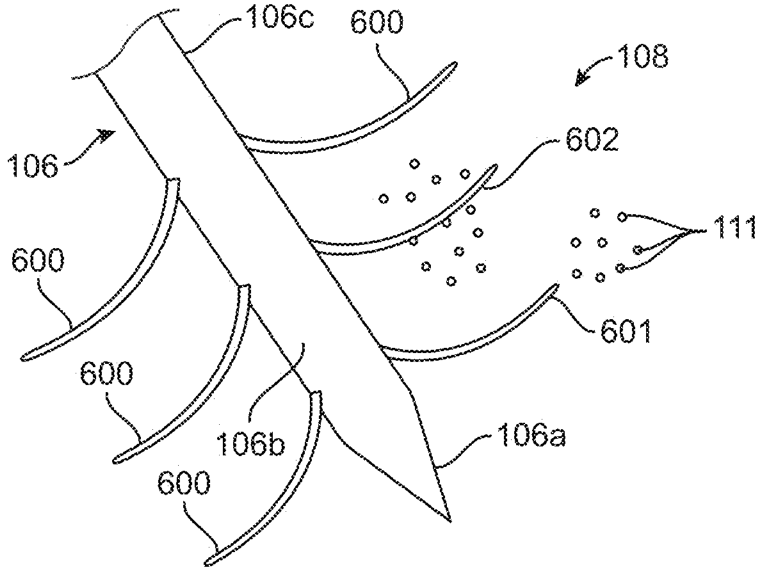
FIG. 40 illustrates an energy delivery device comprising a shaft having an energy delivery body near its distal end, wherein the energy delivery body comprises a plurality of tines.

FIG. 40 illustrates an energy delivery device or instrument 102 comprising a shaft 106 having an energy delivery body 108 near its distal end, wherein the energy delivery body 108 comprises a plurality of tines 600. Typically, the tines 600 have a pointed shape so as to penetrate tissue. Likewise, the tines 600 typically extend laterally outward from the shaft 106, such as at an oblique angle to or perpendicular to the shaft. In some embodiments the tines 600 are deployed circumferentially around the shaft 106 and in other embodiments the tines 600 are deployed from a side of the shaft 106, such as aligned in a row. In some embodiments, the tines 600 extend the same distance from the shaft 106 and in other embodiments the tines 600 extend a varied distance. It may be appreciated that in some embodiments, the extension of at least some of the tines 600 from the shaft 106 is adjustable. It may also be appreciated that in some embodiments the tines 600 extend from a distal tip of the shaft 106, such as through a central lumen.

Typically, each tine 600 delivers agent 111 and/or energy therefrom. In some embodiments, agent 111 is delivered from the tip 601 of the tine 600 and in other embodiments agent 111 is delivered from delivery ports 602 along the tine 600. In some embodiments, the tines 600 are energizable together (e.g. so as to act as a single electrode) or at least some of the tines 600 are individually energizable (e.g. so as to act in bipolar pairs or so as to act as selectable single electrodes including acting in groups). In some embodiments, one or more tines 600 deliver different energy (e.g. generated from different energy delivery algorithms 152) and/or different types of agent 111.

In this embodiment, the shaft 106 has three sections, a first section 106*a*, a second section 106*b* and a third section 106*c*. As illustrated in FIG. 40, the first section 106*a* is distal to the second section 106*b* which is distal to the third section 106*c*. Each section 106*a*, 106*b*, 106*c* may be insulated or non-insulated so as to create a variety of different electrode combinations. This may allow various electric field shapes and/or direct the electric field in desired directions. It may also be appreciated that in some embodiments, at least a portion of at least one tine 600 is insulated so as to direct the energy emanating therefrom. Overall, the tines 600 are often able to deliver agent 111 and/or energy to a larger volume of target tissue with a single placement of the instrument 102 than with an instrument 102 having an energy delivery device 108 comprising a single needle.

In some embodiments, the first section 106*a* acts as an energy delivery body 108 and one or more tines 600 act as energy delivery bodies 108. Each of the different energy delivery bodies 108 may deliver the same or different types of energy; likewise, the energy delivery bodies 108 may act in groups. In some embodiments, the tines 600 extend past the first section 106*a*. In some embodiments, the tines 600 extend the same distance (relative to the first section 106*a*) from the shaft 106 and in other embodiments the tines 600 extend a varied distance (relative to the first section 106*a*). In some embodiments, the first section 106*a* acts as an energy delivery body 108 and one or more tines 600 act as a conduit for delivery of agent 111.

It may be appreciated that in some embodiments, PEF energy is delivered to a conductive fluid (e.g. blood, saline, etc.) in contact with the target tissue. Thus, the energy is able to pass through the conductive fluid to the target tissue for the effects described herein above.

In summary, specialized PEF treatments described herein invoke an adaptive immune response that benefits treatment outcomes. To verify that inclusion of checkpoint blockade (CPB) into a PEF treatment protocol improves outcomes beyond PEF-alone, two syngeneic, orthotopic models of triple-negative breast cancer (EMT6 and 4T-1 murine tumor models) were employed in studies. To verify that the inclusion of checkpoint blockade into a PEF therapeutic protocol with PEF treatment could improve outcomes beyond PEF-alone, a syngeneic, orthotopic model of triple-negative breast cancer (the EMT6 tumor model) was employed in studies. Next, to verify that combination therapy cohorts provided long term, tumor specific immunity, the animals that achieved a CR with a EMT6 tumor cell injection 60 days post treatment were rechallenged. To verify how combination therapy synergizes to generate an anti-tumor immune response, a pathway analysis on systemic changes to cytokine expression in the blood before and after treatment was performed. Next, tumor suppression mediated by PEF treatment combined with checkpoint blockade in a syngeneic model of metastatic breast cancer was assessed. To determine that combination therapy improved the anti-tumor immune response in lung metastases, cytokine analysis was performed and quantified a nuclear proliferation factor (Ki67) in 4T-1 lung tissue at 18 days post-treatment.

It may be appreciated that in some embodiments described herein, PEF energy delivery and CPB synergize to accomplish the following: immunogenic cell death, release of tumor antigen and DAMPs, proinflammatory TME driving by innate arm, Skew Th1/Th17, DC Activation, NK Activation, TLR signaling, cytotoxic T-cell activation, and wound healing response, to name a few.

Example 3

Immunogenicity of Specialized Pulsed Electric Fields is Enhanced with the Inclusion of Checkpoint Inhibitor Therapy Background: Checkpoint inhibition monotherapy has generated impressive clinical results across several cancer subsets; however, the response remains limited in patients whose tumors lack a robust T-cell infiltrate. Further, for patients that do achieve a clinically meaningful response, these anti-tumor effects are commonly transient as the tumor moves to a more immune suppressive phenotype. As such, there is growing interest to improve disease outcomes by combining checkpoint blockade with a local therapy. Local therapies have the potential to rapidly promote immunogenic cell death and the subsequent release of tumor antigen to drive a systemic anti-tumor response. PEF treatment is a non-thermal, needle-guided, locoregional therapy that employs high frequency biphasic electric pulses to destabilize the cell membrane and drive cellular death. Importantly, PEF preserves the extracellular matrix (ECM) and allows for regeneration of blood and lymphatic vessels. Here, we set out to determine if the combination of PEF and programmed cell death receptor-1 (anti-PD-1) blockade would bolster a systemic anti-tumor response in a murine model of triple negative breast cancer.

Objectives: This preclinical study evaluated the immune response to specialized Pulsed Electric Field (PEF) tumor treatment with inclusion of checkpoint inhibition with αPD-1. Where appropriate PEF treatment doses do not denature proteins, tumor-specific and tumor-associated antigens remain intact and available for antigen-presenting cells to interact with them during the treatment resolution and reparative processes, including an abscopal effect. This study identified the immunogenic mechanisms underlying the abscopal effect and enhanced response obtained by combinatorial treatment.

Methods: Immunocompetent female Balb/c mice were orthotopically inoculated with 1200, 000 4T1 breast cancer cells (representing "cold" tumor microenvironments) in the 5th mammary fat pad (primary tumor). Mice were distributed into 4 groups: IgG controls, anti-PD1-only, PEF-only, and anti-PD1+PEF. The anti-PD1 dosing was 200 μg given three times per week starting the day of tumor inoculation. Once reaching 5 mm in diameter (8-10 days), tumors in the PEF groups were treated with a single application of specialized PEF delivered through a single needle placed in the center of the tumor. PEF dosing was established to target approximately 80% of the tumor volume. The specialized PEF dose was 2500V, 400 kHz, 40 cycles, 100 packets. Three days following PEF treatment delivery day, a second 4T-1 tumor was challenged into the contralateral side of the fifth mammary fat pad (secondary tumor). Eighteen days after treatment, contralateral tumors and lungs were harvested for analysis. Enzyme-linked immunosorbent analysis (ELISA) was used to identify and characterize the biological immune response to the different treatment cohorts.

Figure 41:
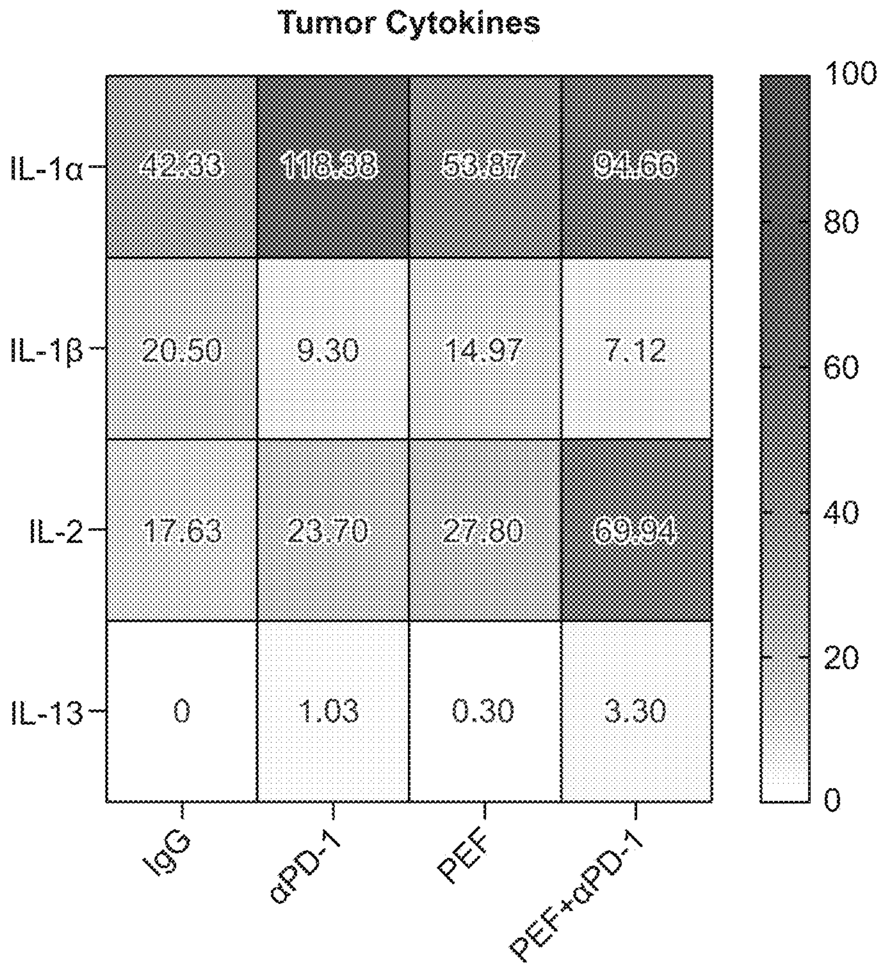
FIG. 41 provides a heat map depicting cytokine expression from the contralateral whole tumor lysate 18 days after treatment.
Figure 42A:
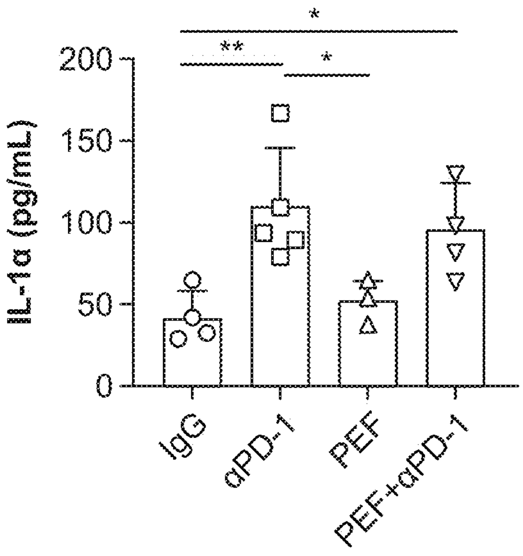
FIGS. 42A-42D refer to cytokine presence in a secondary (untreated) tumor.
Figure 42B:
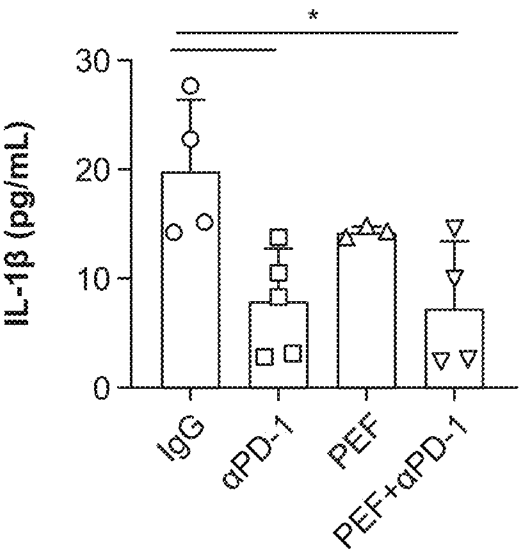
Figure 42C:
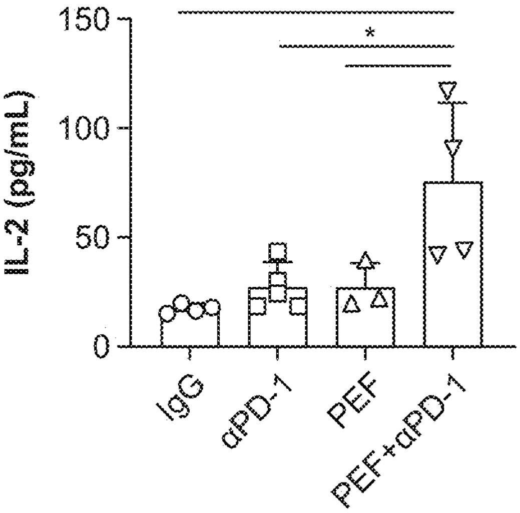
Figure 42D:
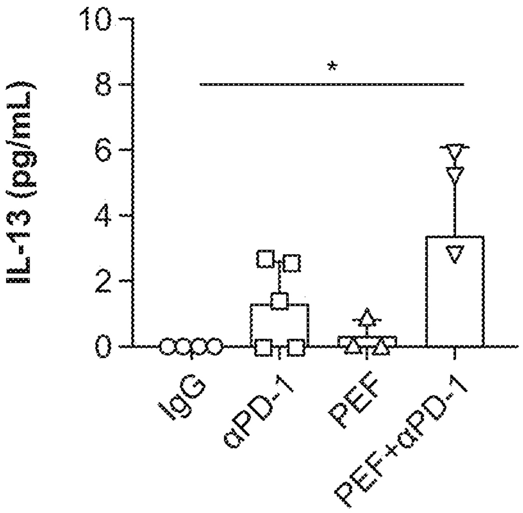

Results: Cytokine analysis performed in untreated tumors and lung tissue with metastatic disease at 18 days post-treatment confirmed that combinatorial treatment alleviated systemic immune suppression. The cytokine panel included GM-CSF, IL-la, IL-1, IL-2, IL-4, IL-5, IL-6, IL-7, IL-10, IL-12, IL-13, IL-17, CXCL1, CXCL2, CXCL5, CCL2, TGF-a. The PEF and checkpoint blockade significantly elevated the expression of T-cell activator, IL-2, in the secondary untreated tumors, whereas all other study cohorts did not FIG. 41 provides a heat map depicting cytokine expression from the contralateral whole tumor lysate 18 days after treatment. Biological groups included the following: Control (IgG, n=4) anti-PD-1 checkpoint monotherapy ((αPD-1, n=4), direct treatment with pulsed fields (PEF, n=3), and combination therapy (PEF+αPD-1, n=4). The heat map represents the average concentration (pg/mL) of cytokine for each biological group. Multiplex cytokine quantification for IL-a (FIG. 42A), IL-β (FIG. 42B), IL-2 (FIG. 42C), IL-13 (FIG. 42D) were used to construct the heat map in FIG. 41. *p<0.05, p<0.01 (ANOVA with Fisher's test). All data are plotted mean±standard deviation. FIGS. 42A-42**D refer to cytokine presence in the secondary (untreated) tumor.

Figure 43A:
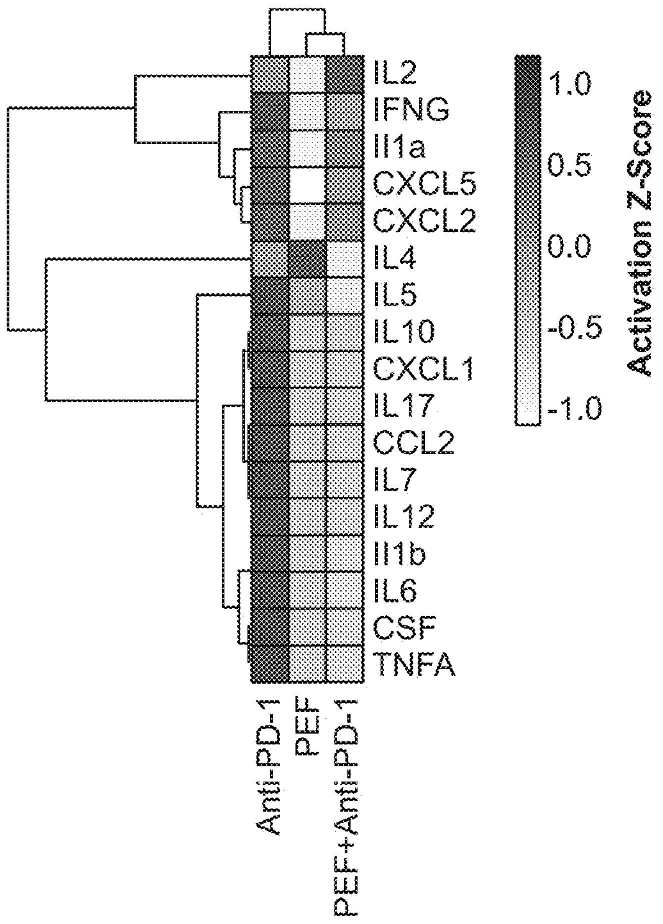
FIG. 43A provides a heat map depicting cytokine expression from the contralateral whole tumor lysate 18 days after treatment.
Figure 43B:
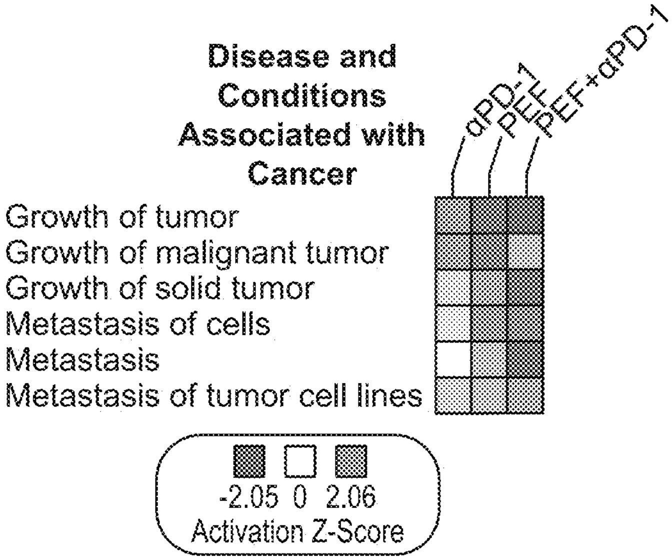
FIG. 43B illustrates analysis of how cytokine expression from lung tissue impacts pathways associated with cancer as determined by Ingenuity Pathway Analysis (IPA) software.

Further, treatment with PEF and immunotherapy significantly decreased the neutrophil recruitment chemokine, CXCL1, in both the secondary untreated tumor and lung compared to IgG control group. Thus, immune therapy combined with PEF induced anti-tumor immune response in lung metastases. FIG. 43A provides a heat map depicting cytokine expression from the contralateral whole tumor lysate 18 days after treatment. FIG. 43B illustrates analysis of how cytokine expression from lung tissue impacts pathways associated with cancer as determined by Ingenuity Pathway Analysis (IPA) software.

Figure 44A:
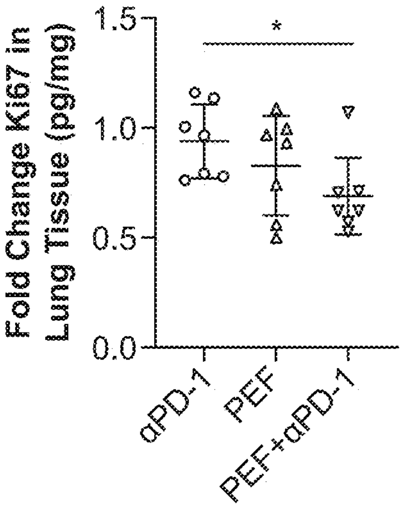
FIGS. 44A-44B provides an ELISA quantification of Ki-67 from whole lung tissue lysate 18 days after treatment.
Figure 44B:
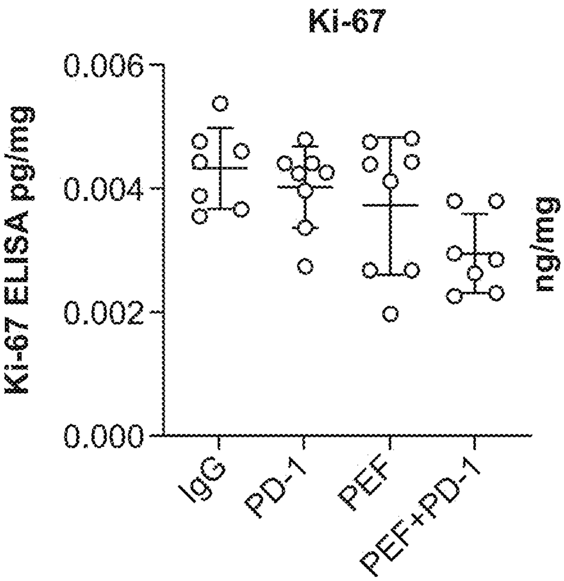
Figure 44C:
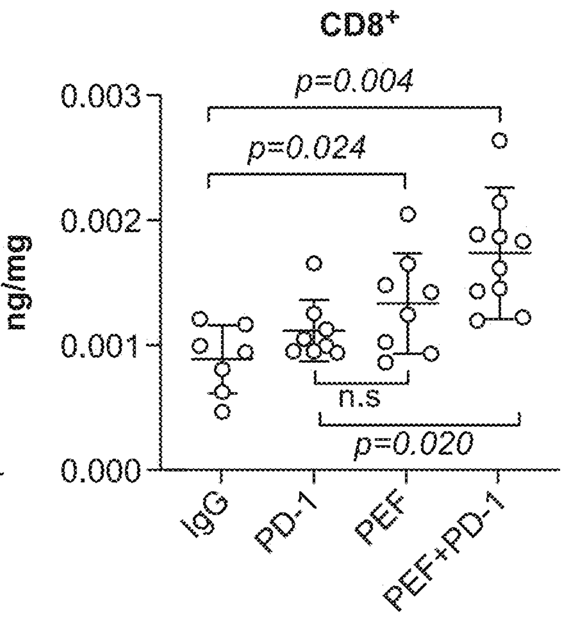
FIG. 44C provides an ELISA quantification of CD8 from whole lung tissue lysate 18 days after treatment.

To characterize the metastatic burden in treated animals, a marker for tumor viability (Ki67) and cytotoxic T-cells in the immune cell infiltrate (CD8) were quantified in whole lung tissue via ELISA. PEF monotherapy and PEF combined with immunotherapy increased the expression CD8 in the lungs compared to both the IgG control and checkpoint monotherapy cohorts. FIGS. 44A-44B provides an ELISA quantification of Ki-67 from whole lung tissue lysate 18 days after treatment. Biological groups included the following: Control (IgG, n=7), anti-PD-1 checkpoint monotherapy (αPD-1, n=8), direct treatment with pulsed fields (PEF n=3) and combination therapy (PEF+αPD-1, n=7) *p<0.05, p<0.01, *p<0.001 (ANOVA with Fisher's test). All data are plotted mean±standard deviation. Importantly, only the PEF and immunotherapy cohort decreased the total expression of Ki67 in the lungs compared to the IgG control group. FIG. 44C provides an ELISA quantification of CD8 from whole lung tissue lysate 18 days after treatment. Biological groups included the following: Control (IgG, n=7), anti-PD-1 checkpoint monotherapy (αPD-1, n=8), direct treatment with pulsed fields (PEF n=3) and combination therapy (PEF+αPD-1, n=7) *p<0.05, p<0.01, *p<0.001 (ANOVA with Fisher's test). All data are plotted mean±standard deviation.

Summary: Cytokine analysis performed in untreated tumors and lung tissue with metastatic disease of 18 days post-treatment confirmed that combinatorial treatment alleviated systemic immune suppression. PEF and checkpoint blockade significantly elevated the expression of T-cell activator, IL-2, n the secondary untreated tumors, whereas all other study cohorts did not. Further, treatment with PEF and immunotherapy significantly decreased the neutrophil recruitment chemokine, CSCL-1, in both the secondary untreated tumor and lung compared to IgG control group. To characterized PEF mediated changes to metastatic burden in the lung, we first employed Ingenuity Pathway Analysis (IPA) software to identify biological functions and gene networks impacted by treatment. Combination therapy led to significant decreases in pathways associated with cancer including growth of tumors and metastasis. Next, we assessed a marker for tumor viability (K167) and cytotoxic T-cells in the immune cell infiltrate (CD8) were quantified in whole lung tissue via ELISA. PEF monotherapy increased the expression CD8 in the lungs compared to both the IgG control and checkpoint monotherapy cohorts. Importantly, only the PEF and immunotherapy cohort decreased the total expression of K167 in the lungs compared to IgG control group.

Conclusions: Combining PEF with αPD-1 checkpoint inhibition induces a robust local and systemic anti-tumor immune response in the immunosuppressive 4T-1 tumor model.

Example 4

Primary and Secondary Tumor Response to Combined Delivery of Specialized PEF and αPD-1 within 4T-1 and EMT-6 Orthotopic Tumor Models Background: While treatment options for cancer patients have improved for many forms of cancer, the occurrence of acquired drug resistance, a high incidence of tumor recurrence, and systemic spread are unrelenting negative outcomes. However, recent efforts have demonstrated that the combination of immunotherapies (i.e., checkpoint inhibitors, such as αPD-1) in concert with pulsed electric fields (PEF) may improve overall outcomes. PEF is an energy directed focal therapy that relies on the application of brief, high-amplitude, pulsed energy to elicit a cascade of local events including cell death, inflammatory signaling, and the generation of viable antigen presentation within the tumor microenvironment resulting in a measurable systemic response.

Objective: The objective of this preclinical study was to assess the overall synergistic effects of combining specialized PEF with checkpoint blockade (CPB).

Methods: Immunocompetent female Balbc mice were anesthetized and inoculated orthotopically with 200,000 cells (EMT-6 or 4T-1, representing immune "hot" and "cold" tumor microenvironments, respectively) in the 5th mammary fat pad (primary tumor). Mice were distributed into 4 groups: IgG controls, αPD1 monotherapy, PEF monotherapy, and αPD-1+PEF. The αPD-1 dosing was 200 μg given three times per week starting the day of tumor inoculation. Once reaching 5 mm in diameter (8-10 days), tumors in the PEF groups were treated with a single application of PEF delivered through a single needle placed in the center of the tumor. PEF dosing was established to target approximately 80% of the tumor volume. Three days following PEF treatment delivery day, a second inoculation was performed in the contralateral fat pad (secondary tumor). Mice were monitored for health and tumor size three times a week. Mice were euthanized at experimental time-points or at end of the study or if considered clinically moribund.

Figure 45:
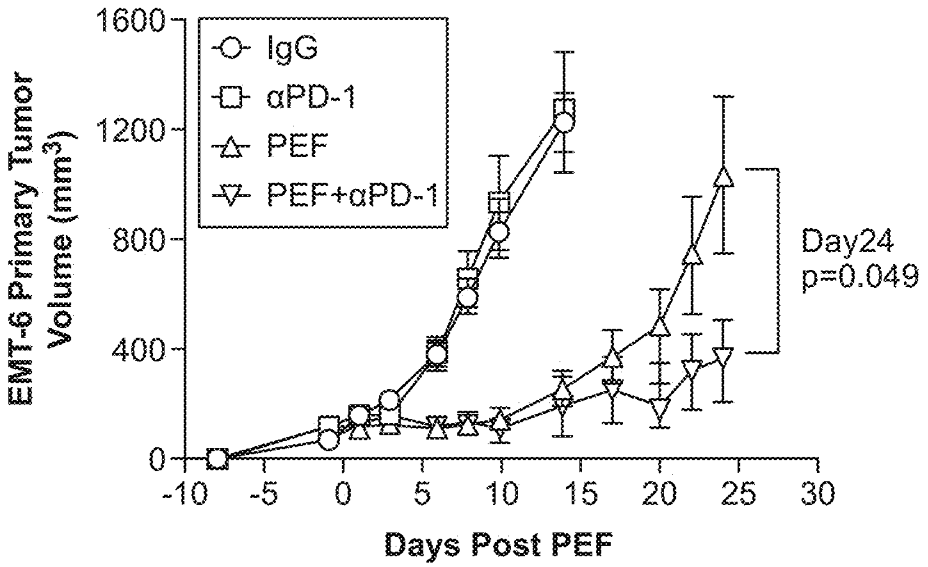
FIG. 45 illustrates a primary tumor growth curve 14 days post PEF for the EMT-6 mouse tumor model.
Figure 46:
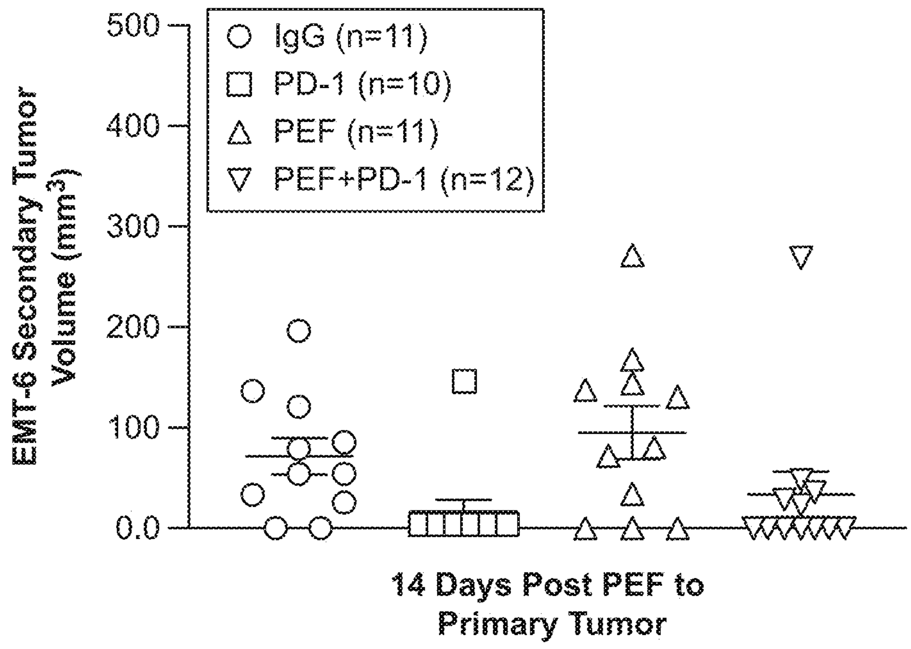
FIG. 46 illustrates a secondary tumor growth curve 14 days post PEF for the EMT-6 mouse tumor model
Figure 47:
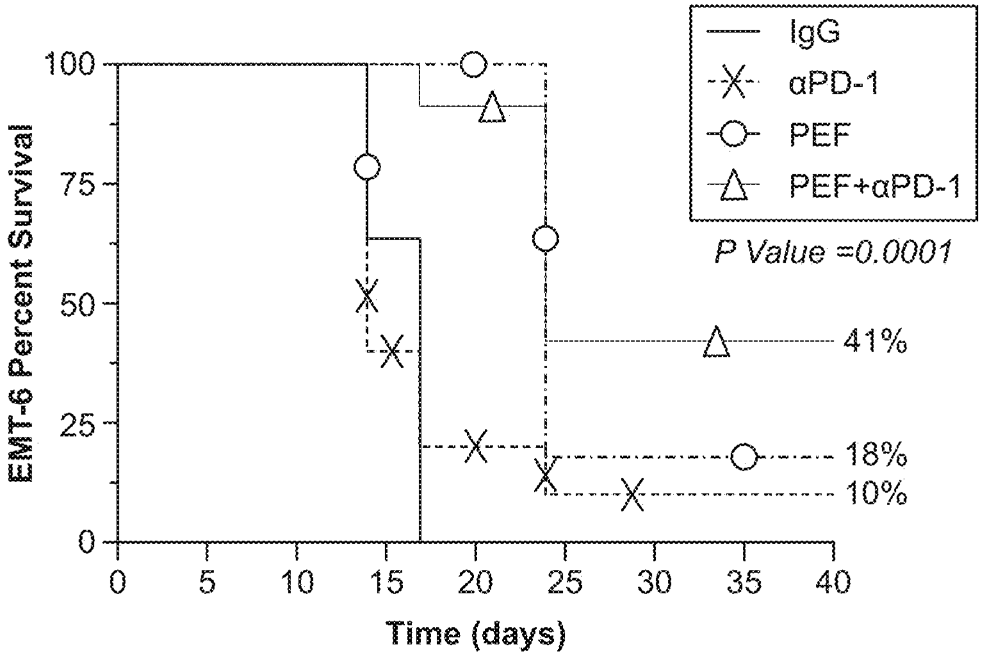
FIG. 47 illustrates a survival plot over 24-day period.

Results: Directly treated and contralateral tumors in the PEF+αPD-1 cohort experienced significant suppression in tumor growth by 24 days post-treatment compared to all groups within the EMT-6 mouse tumor model (FIG. 45). Further, 58% of the PEF+αPD-1 cohort did not grow a contralateral tumor (FIG. 45). Overall, the combinatorial therapeutic protocol significantly (P value<0.001) improved survival outcomes in comparison to PEF or αPD-1 mono-therapy. More specifically, 41% of animals treated with PEF+αPD-1 achieved a complete response as compared to 10% and 18% of animals αPD-1 and PEF monotherapy, respectively (FIG. 46). FIG. 45 depicts the tumor growth curve of EMT6 tumors treated with PEF, with anti-PD1 and with both therapies in comparison to untreated tumors (IgG). The PEF treated groups showed a significant growth delay compared to IgG and αPD1. The combination of PEF with anti PD1 is further inhibiting tumor growth. FIG. 45 shows the tumor growth of contralateral untreated tumors. The contralateral tumor of mice that received systemic anti PD1 and local PEF on the primary tumors failed to grow the satellite tumor in 7/12 mice. FIG. 46 shows that mice treated with PEF on the primary tumor and systemic anti PD1 therapy had a survival rate of 41% compared to PEF alone (18%), anti PD1 alone (10%) and no treatment (0%) Thus, referring to FIGS. 44-46, the primary tumor growth curve (FIG. 45) and secondary tumor growth curve (FIG. 46) at 14 days post PEF for the EMT-6 mouse tumor model are shown along with a survival plot over 24-day period (FIG. 47).

Figure 48A:
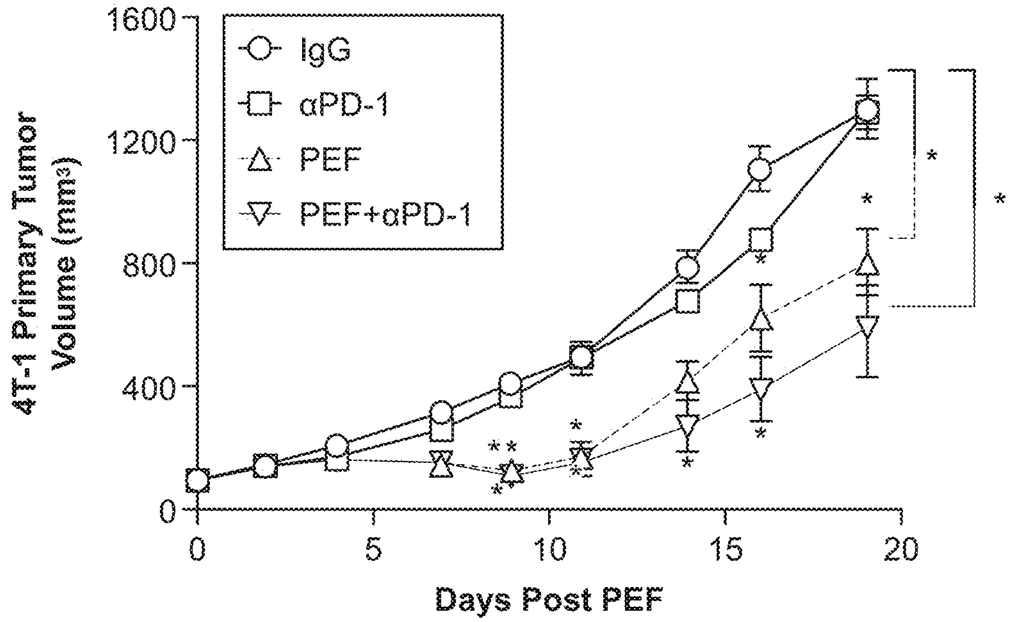
FIGS. 48A-48B illustrates a primary tumor growth curve (FIG. 48A) and secondary tumor growth curve (FIG. 48B).
Figure 48B:
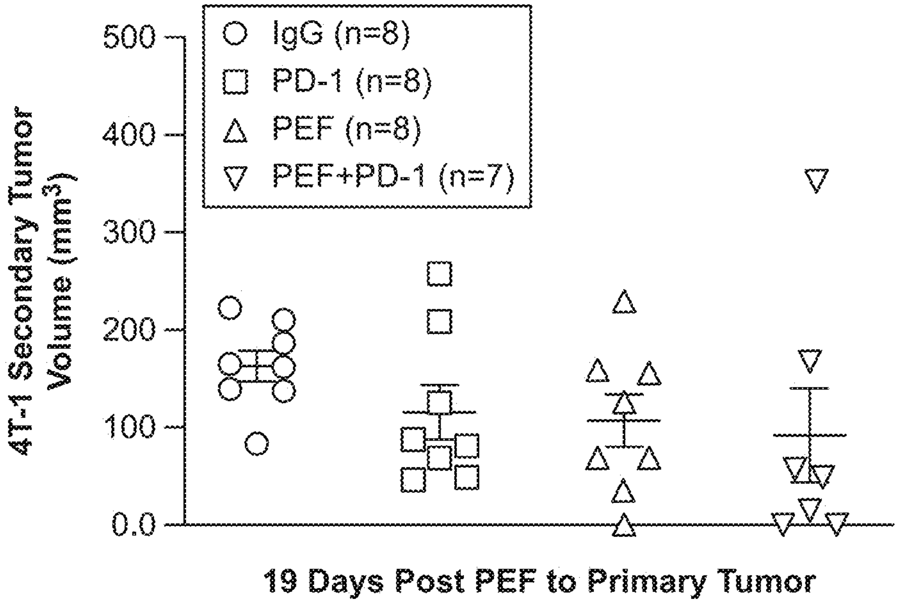

Similarly, the 4T-1 tumor model illustrated a significant reduction (P value<0.05) in the primary and contralateral tumor growth for both the PEF monotherapy and the PEF+αPD-1 groups in comparison to the IgG and αPD-1 mono-therapy at 19 days post PEF (FIG. 48A). Referring to FIGS. 48A-48B, the primary tumor growth curve (FIG. 48A) and secondary tumor growth curve (FIG. 48B) are shown 19 days post PEF for the 4T-1 mouse tumor model. No contralateral tumor growth was achieved in 29% of the mice that received the combinatorial therapy and 13% of the mice that received PEF monotherapy.

Conclusions: This data suggest that checkpoint inhibition (αPD-1) and focal PEF therapy act synergistically to create a bolstered anti-tumor response within both an immunogenic (EMT-6) and immunosuppressive (4T-1) mouse tumor models.

Example 5

Figure 49A:
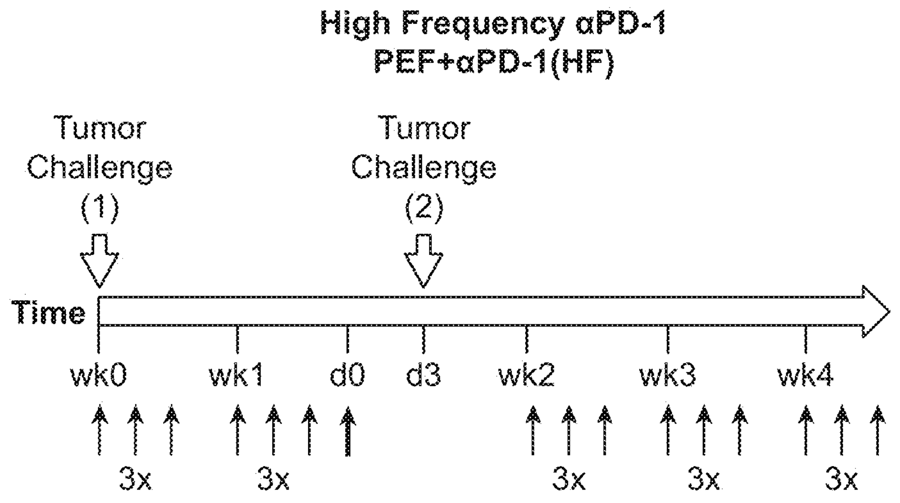
FIG. 49A illustrates a high frequency anti-PD-1 dosing scheme initiated at the time of primary tumor inoculation.
Figure 49B:
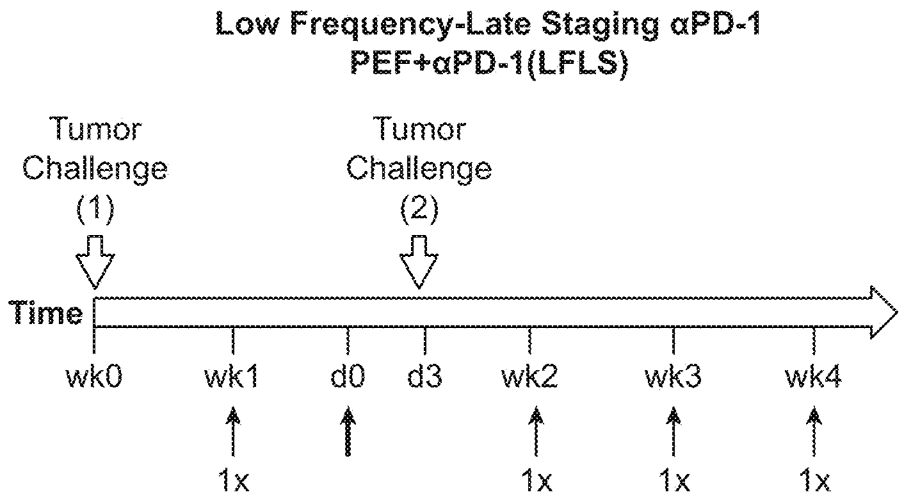
FIG. 49B illustrates a low frequency-late stage anti-PD-1 dosing scheme where CPB was initiated at the time of the PEF treatment.
Figure 50:
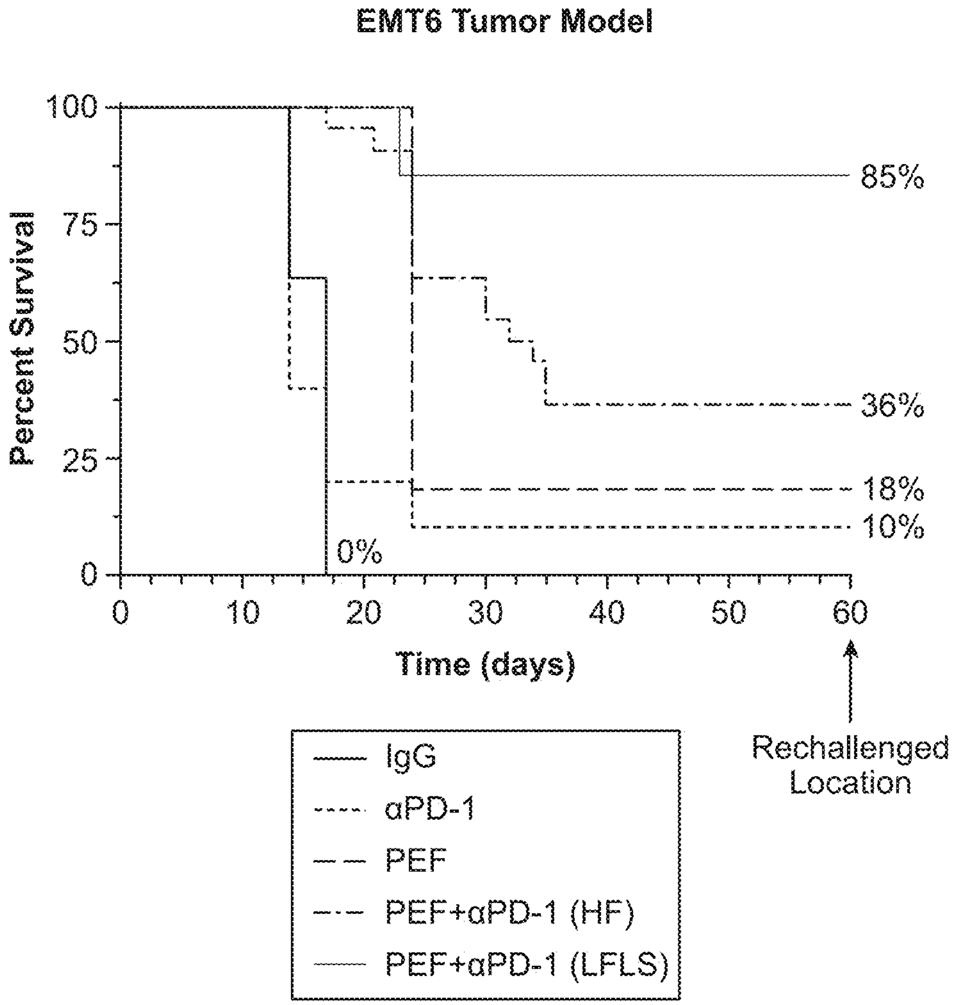
FIG. 50 is a Kaplan-Meier Curve depicting survival at 60 days post treatment.
Figure 51A:
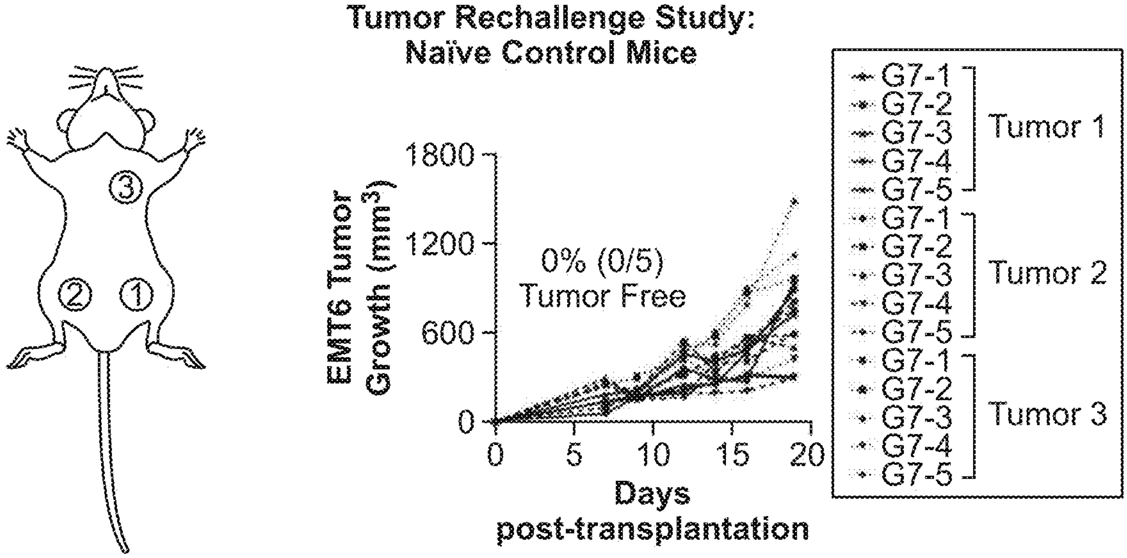
FIGS. 51A-51B illustrates EMT6 tumor growth in native control mice that had not previously been challenged with EMT6 tumor cell injection and animals from the PEF and CPB combination that had previously achieved a complete response.
Figure 51B:
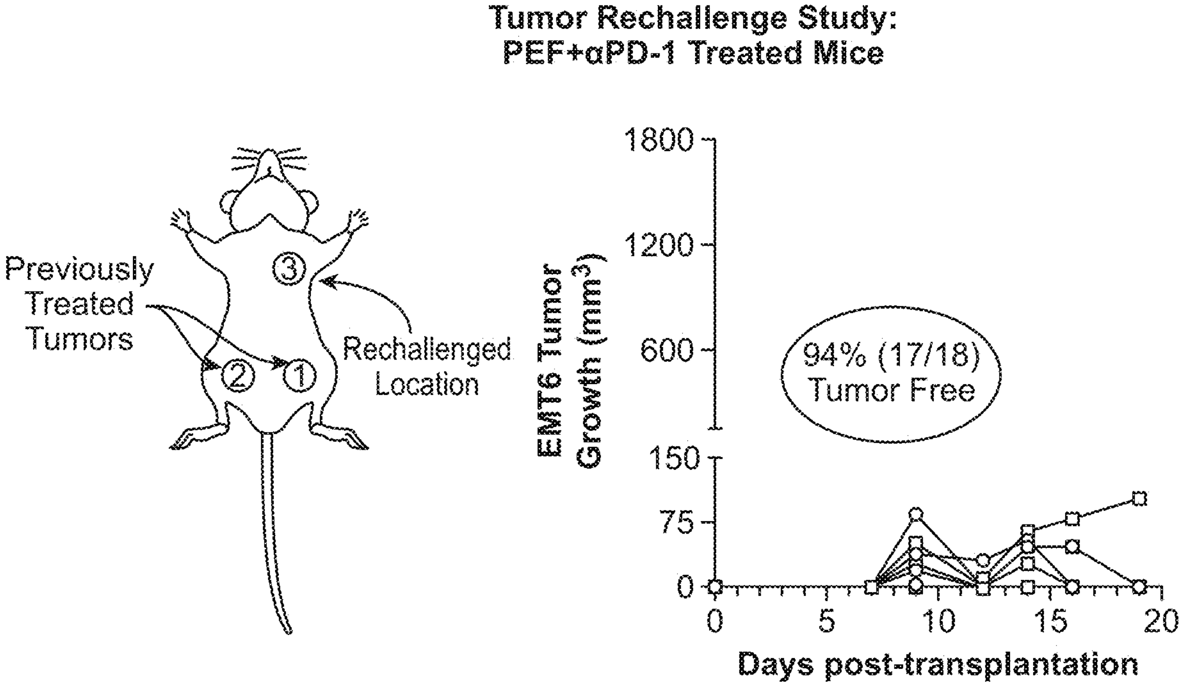

A similar study was undertaken that compared two different dosing schedules. Two individual CPB dosing schemes were evaluated via survival impact, to optimize the improvement of combining CPB with PEF therapy compared to CPB alone. These dosing schemes included a high frequency anti-PD-1 dosing schedule initiated at the time of primary tumor inoculation (FIG. 49A), and a low frequency-late stage anti-PD-1 dosing schedule, where CPB was initiated at the time of the PEF treatment (FIG. 49B). Each of the combinatorial therapeutic dosing scheme significantly (p<0.001) improved survival outcomes in comparison to PEF or anti-PD1 monotherapy. Complete response (CR) was obtained in 36% and 85% of combinatorial PEF+anti-PD-1 mice in the high frequency and low-frequency late state anti-PD-1 dosing groups, respectively. This compares to 10% and 18% of animals anti-PD1 and PEF monotherapy, respectively (FIG. 50). FIG. 50 is a Kaplan-Meier Curve depicting survival at 60 days post treatment. Biological groups included Control (IgG, n=11), anti-PD-1 checkpoint monotherapy (αPD-1, n=11), direct treatment with pulsed fields (PEF, n=11), high frequency CPB+PEF (PEF+αPD-1) (HF), n=22), low frequency late staging CPB+PEF (PEF+αPD-1) (LFLS), n=7), Next, to identify combination therapy cohorts which provided long term, tumor specific immunity, we rechallenged the animals that achieved a CR with an EMT6 tumor cell injection 60 days post treatment into a native tumor site, the second mammary fat pad (FIGS. 51A-51B). FIG. 51A depicts native control mice those that had not previously been challenged with EMT6 tumor cell injection. FIG. 51B depict animals from the PEF and CPB combination groups that had previously achieved a complete response. For native control mice, tumors were inoculated into the $5^{th}$ (left and right side) and $2^{nd}$ mammary fat pad (left side only). For PEF+anti-PD-1 mice, a tumor was challenged into the second mammary fat pad only. All tumors readily grew in a control cohort. Collectively, 94% of (17/18) animals treated with combination therapy did not exhibit tumors by 20 days post-inoculation.

Figure 52:
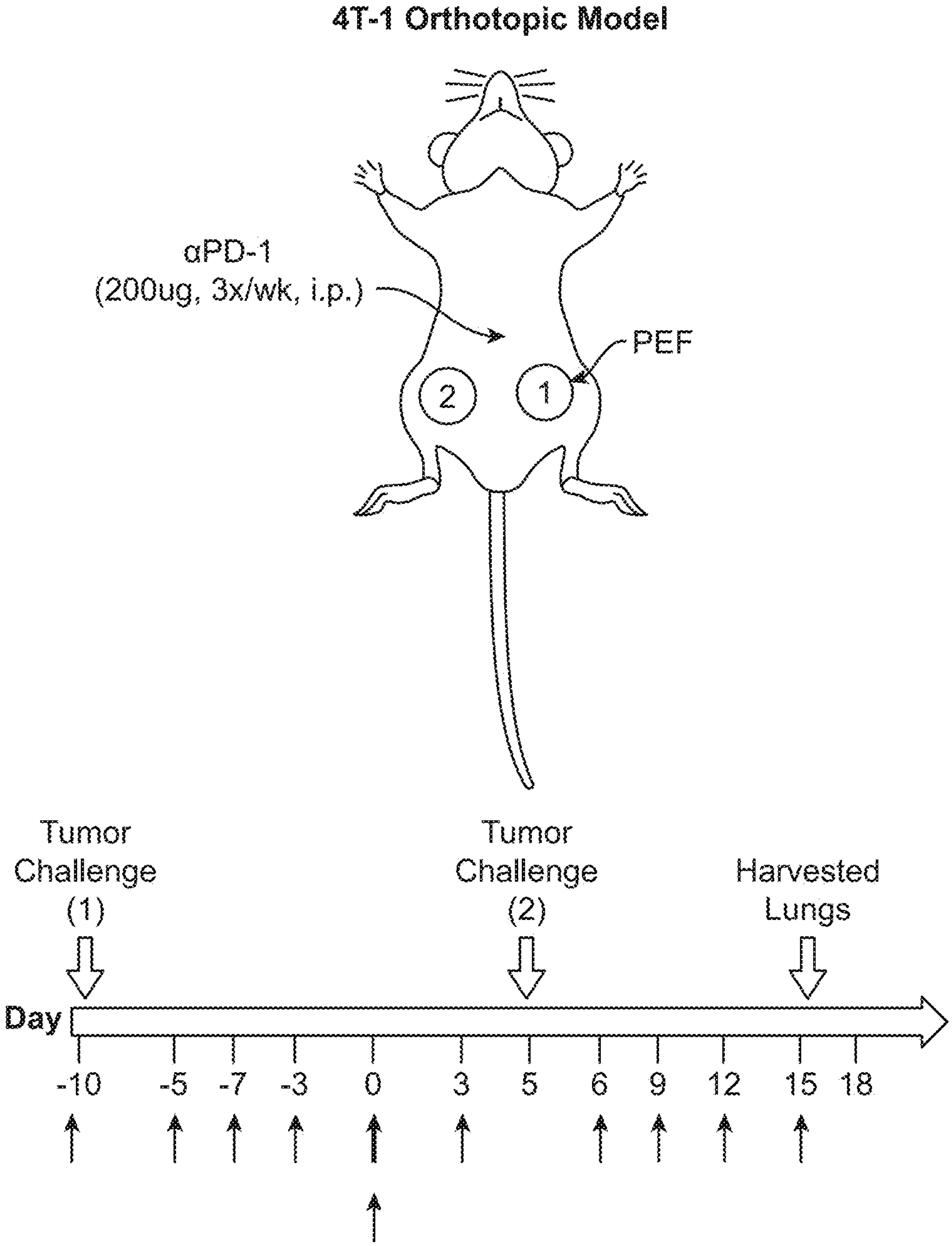
FIG. 52 is a dosing schedule of Balb/c mice that were orthotopically challenged with 200,000 cells (4T-1) in the $5^{th}$ mammary fat pad (both left and right side, bilateral tumor model).

Regarding FIG. 52, Balb/c mice were orthotopically challenged with 200,000 cells (4T-1) in the $5^{th}$ mammary fat pad (both left and right side, bilateral tumor model). Mice were distributed into 4 groups: Control (IgG, n=8), anti-PD-1 checkpoint monotherapy (αPD-1, n=8), direct treatment with pulsed fields (PEF, n=8), and combination therapy (PEF+αPD-1, n=7), Once reaching 5 mm in diameter (10 days) tumors in the PEF groups were treated with a single application of PEF delivered through a single needle placed into the center of the tumor.

Figure 53:
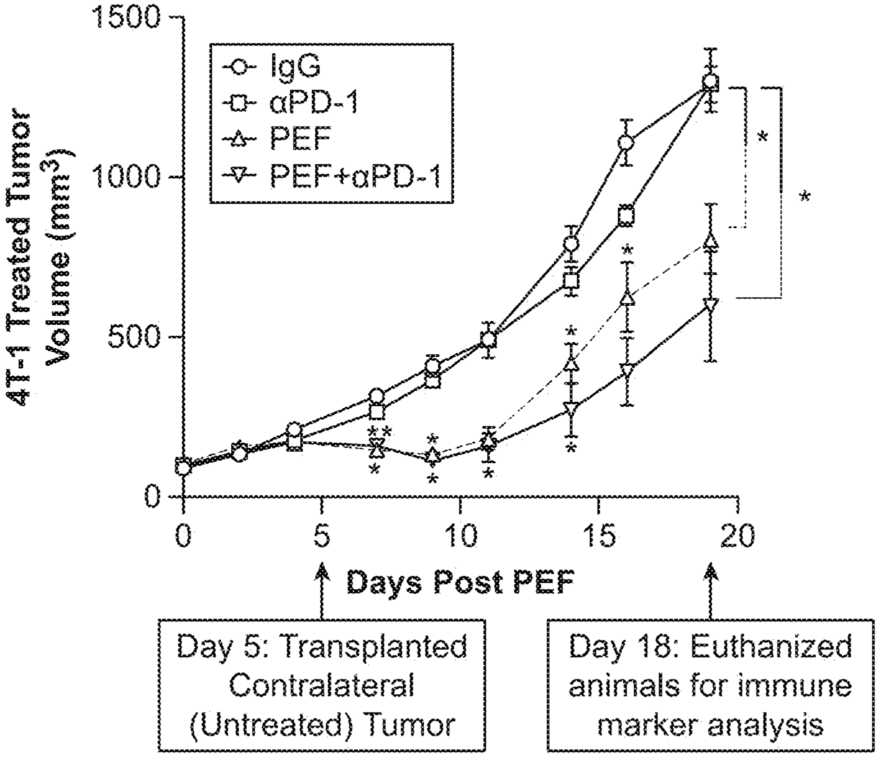
FIG. 53 is a growth plot of the primary, or directly treated, 4T-1 tumors.

Similarly, the 4T1 tumor model illustrated a significant reduction (p<0.05) in the primary and contralateral tumor growth for both the PEF monotherapy and the PEF+anti-PD-1 groups in comparison to IgG and PD-1 monotherapy at 19 days post PEF. The contralateral tumors were significantly smaller in the PEF+anti-PD-1 group (FIG. 53). No contralateral tumor growth was achieved in 43% of the mice that received the combinatorial therapy and 12% of mice that received the monotherapy (PEF alone).

FIG. 53 is a growth plot of the primary, or directly treated, 4T-1 tumors. Biological groups included the following: Control (IgG, n=8), anti-PD-1 checkpoint monotherapy (αPD-1, n=8), direct treatment with pulsed fields (PEF, n=8), and combination therapy (PEF+αPD-1) (LFLS), n=7. *p<0.05 (Repeated Measures ANOVA with Tukey test). All data plotted mean±SEM.

Figure 54:
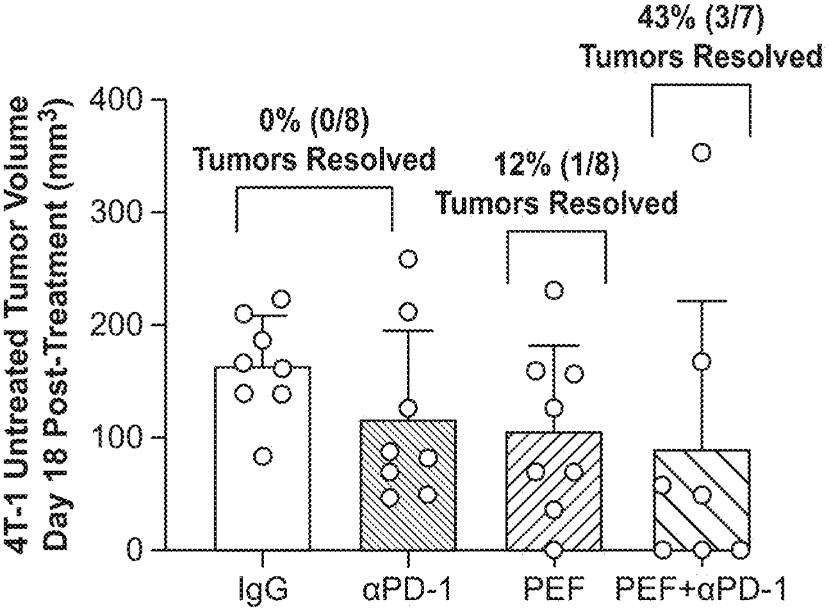
FIG. 54 illustrates a comparison between biological groups of the contralateral or untreated 4T-1 tumor volume 18 days post PEF, or 13 days after inoculation.

FIG. 54 is a comparison between biological groups of the contralateral or untreated 4T-1 tumor volume 18 days post PEF, or 13 days after inoculation. All data are plotted mean±standard deviation.

Conclusion: This data suggests that checkpoint inhibition (αPD-1) and focal PEF therapy act synergistically to create an enhanced, durable, anti-tumor response within both an immunogenic (EMT-6) and immunosuppressive (4T-1) mouse tumor models.

Altered PEF Dosing

As stated previously, the specialized treatment dose is provided by a waveform that is produced from a combination of parameter values that includes the following: voltage=3000V, fundamental frequency=400 kHz, number of biphasic pulses (i.e., cycles) per packet=40 cycles, inter-cycle delay=1000 microseconds, number of packets=100 packets and inter-packet delay=3 seconds. It may be appreciated that deviations from this specialized dose typically generate different results.

Referring back to FIG. 28, a variety of tissue samples having Tertiary Lymphoid Structures (TLS) are shown wherein the presence of TLS in tumors correlate with better prognosis and clinical outcome. Lymphoid aggregates and TLS have been consistently observed near the periphery of the PEF treated tumors when treated with the specialized treatment dose. However, when the dose is altered (tissue samples T1, T2, T3 of FIG. 28), the number of TLS are dramatically reduced or non-existent. The tumor in tissue sample T1 received the specialized dose, however the energy delivery was asynchronous with the heartbeat with a brief interruption in energy delivery. The tumor in tissue sample T2 received the energy in two doses that each had 50 packets rather than a single dose that had 100 packets. The tumor in tissue sample T3 also received the energy in two doses that each had 50 packets rather than a single dose that had 100 packets so as to generate a CT scan to assess needle placement and packet delivery. For these cases, the energy delivery was interrupted halfway through, with a pause sufficiently long to prevent further accumulation of treatment effect, and thus had a functionally different dose than the later samples. The average number of TLS in the tissues of FIG. 28 (T1, T2, T3, T4, T5, T6, T7, T8, T9, T10, T11, T12) is 54.8 whereas the average number of TLS in the tissues receiving the altered dose (T1, T2, T3) is only 4. The number of TLS is made up of mature TLS (which have germinal centers containing mature CD20-B cells exhibiting the characteristic morphology of proliferating centroblasts, often with tingible body macrophages and follicular dendritic cells within the germinal center) and immature TLS (without germinal centers). The average of mature TLS in the tissues of FIG. 28 (T1, T2, T3, T4, T5, T6, T7, T8, T9, T10, T11, T12) is 5.6 whereas the average number of TLS in the tissues receiving the altered dose (T1, T2, T3) is 0. The average of immature TLS in the tissues of FIG. 28 (T1, T2, T3, T4, T5, T6, T7, T8, T9, T10, T11, T12) is 49.2 whereas the average number of TLS in the tissues receiving the altered dose (T1, T2, T3) is 4. It may be appreciated that the averages of the tissues of FIG. 28 include T1, T2, T3, therefore the average when excluding these three tumors would be even higher. Thus, the difference in effect of the altered dose is higher than calculated. This indicates that alterations in the specialized dose may lead to a lower immunological response, decreased efficacy and less desirable clinical outcome.

Nonetheless, it may be appreciated that different parameters may be used, typically with different outcomes. The different outcomes may be different in some aspects and similar in other aspects. Likewise, the different outcomes may be preferred in some situations and not in others. The following further describe the parameters of the energy waveform.

A. Voltage

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 416 is between about 500 V to 10,000 V, particularly about 3000V to 3300V, 3000V to 3500V, 3300 to 3500V, 3500 V to 4000 V, about 3500 V to 5000 V, about 3500 V to 6000 V, including all values and subranges in between including about 3000 V, 3300V, 3500 V, 4000 V, 4500 V, 5000 V, 5500 V, 6000 V to name a few. Voltages delivered to the tissue may be based on the setpoint on the generator 104 while either taking in to account the electrical losses along the length of the instrument 102 due to inherent impedance of the instrument 102 or not taking in to account the losses along the length, i.e., delivered voltages can be measured at the generator or at the tip of the instrument.

It may be appreciated that the set voltage 416 may vary depending on whether the energy is delivered in a monopolar or bipolar fashion. In bipolar delivery, a lower voltage may be used due to the smaller, more directed electric field. The bipolar voltage selected for use in therapy is dependent on the separation distance of the electrodes, whereas the monopolar electrode configurations that use one or more distant dispersive pad electrodes may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at a desired tissue depth (1.3 mm), if the separation distance is changed from 1 mm to 1.2 mm, this would result in a necessary increase in treatment voltage from 300 to about 360 V, a change of 20%.

B. Frequency

It may be appreciated that the number of biphasic cycles per second of time is the fundamental frequency when a signal is continuous. Since the specialized PEF waveforms are not continuous throughout the dose (e.g. the waveform includes packets and delays), the fundamental frequency is used as a method of describing the pulse width of the biphasic pulses of the specialized PEF waveform. It may be appreciated that the pulse width is the measure of the elapsed time between the leading and trailing edges of a single biphasic cycle and can be derived from a value of a fundamental frequency. For example, a waveform having a fundamental frequency of 400 Hz has a biphasic pulse width of 2.5 microseconds.

In some embodiments, biphasic pulses are utilized to reduce undesired muscle stimulation, particularly cardiac muscle stimulation. In other embodiments, the pulse waveform is monophasic and there is no clear inherent frequency. Instead, a fundamental frequency may be considered by doubling the monophasic pulse length to derive the frequency. In some embodiments, the signal has a frequency in the range 100 kHz-1 MHz, more particularly 100 kHz-1000 kHz, including 100 kHz, 200 kHz, 300 kHz, 400 kHz, 500 kHz, 100-500 kHz, etc. In some embodiments, the signal has a frequency in the range of approximately 100-600 kHz which typically penetrates a lumen wall so as to treat or affect particular cells somewhat deeply positioned, such as submucosal cells or smooth muscle cells. In some embodiments, the signal has a frequency in range of approximately 600 kHz-1000 kHz or 600 kHz-1 MHz which typically penetrates a lumen wall so as to treat or affect particular cells somewhat shallowly, such as epithelial or endothelial cells. It may be appreciated that at some voltages, frequencies at or below 100-250 kHz may cause undesired muscle stimulation. Therefore, in some embodiments, the signal has a frequency in the range of 400-800 kHz or 500-800 kHz, such as 400 kHz, 450 kHz, 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

C. Voltage-Frequency Balancing

The frequency of the waveform delivered may vary relative to the treatment voltage in synchrony to retain adequate treatment effect. Such synergistic changes would include the decrease in frequency, which evokes a stronger effect, combined with a decrease in voltage, which evokes a weaker effect. For instance, in some cases the treatment may be delivered using 3000 V in a monopolar fashion with a waveform frequency of 800 kHz, while in other cases the treatment may be delivered using 2000 V with a waveform frequency of 400 kHz.

When used in opposing directions, the treatment parameters may be manipulated in a way that makes it too effective, which may increase muscle contraction likelihood or risk effects to undesirable tissues, such as cartilage for airway treatments. For instance, if the frequency is increased and the voltage is decreased, such as the use of 2000 V at 800 kHz, the treatment may not have sufficient clinical therapeutic benefit. Opposingly, if the voltage was increased to 3000 V and frequency decreased to 400 kHz, there may be undesirable treatment effect extent to collateral sensitive tissues. In some cases, the over-treatment of these undesired tissues could result in morbidity or safety concerns for the patient, such as destruction of cartilaginous tissue in the airways sufficient to cause airway collapse, or destruction of smooth muscle in the GI tract sufficient to cause interruption of normal peristaltic motion. In other cases, the overtreatment of the untargeted or undesirable tissues may have benign clinical outcomes and not affect patient response or morbidity if they are overtreated.

D. Cycles and Packets

As mentioned, the algorithm 152 prescribes a signal having a waveform comprising a series of energy packets wherein each energy packet comprises a series of high voltage pulses. Typically, the pulses are biphasic so they are referred to as cycles. Referring to FIG. 4, the first packet 402 has a cycle count 420 of two. In some embodiments, the cycle count 420 is set from 1 to 100 per packet, including all values and subranges in between, such as 5 cycles, 10 cycles, 20 cycles, 30 cycles, 40 cycles, 50 cycles, 60 cycles, 70 cycles, 80 cycles, 90 cycles, 100 cycles, etc. In some embodiments, the cycle count 420 is 1 to 5 cycles, 1 to 10 cycles, 1 to 25 cycles, 10 to 20 cycles, 1 to 40 cycles, 40 to 50 cycles, 1 to 60 cycles, 50 to 60 cycles, 1 to 80 cycles, 1 to 100 cycles, 50 to 100 cycles, 1 to 1,000 cycles or 1 to 2,000 cycles, including all values and subranges in between.

The packet duration is determined by the cycle count, among other factors. Typically, the higher the cycle count, the longer the packet duration and the larger the quantity of energy delivered. In some embodiments, packet durations are in the range of approximately 50 to 1000 microseconds, such as 50 µs, 60 µs, 70 µs, 80 µs, 90 µs, 100 µs, 125 µs, 150 µs, 175 µs, 200 µs, 250 µs, 100 to 250 µs, 150 to 250 µs, 200 to 250 µs, 500 to 1000 µs to name a few. In other embodiments, the packet durations are in the range of approximately 100 to 1000 microseconds, such as 150 µs, 200 µs, 250 µs, 500 µs, or 1000 µs.

In some embodiments, the number of packets delivered during treatment, or packet count, may include 50 to 280 packets including all values and subranges in between, such as 50, 60, 70, 80, 90, 100, 50-100, 80-100, 100-110, 110, 120, 130, 140, 150, 100-150, 160, 170, 180, 190, 200, 210, 220, 230, 240, 250, 260, 270, and 280 packets.

TABLE 5

Example parameter combinations include:

| Voltage | Frequency | Packet duration | Minimum # of Packets | Penetration |
|---|---|---|---|---|
| 3500 V | 500 kHz | 250 µs | 200 | 0.1-1 cm |
| 5000 V | 5 kHz | 200 µs | 10-20 | 0.5-2 cm |
| 6000 V | 300 kHz | 500 µs | 100 | 3-5 cm |
| 3000 V | 500 kHz | 250 µs | 25-50 | 0.5-2 cm |
| 2500 V | 300 kHz | 150 µs | 100 | 0.5-2 cm |
| 2500 V | 500 kHz | 100 µs | 50 | 0.5 cm |
| 2500 V | 600 kHz | 100 µs | 20 | 0.05-0.1 cm |

E. Rest Period/Inter-Packet Delay

In some embodiments, the time between packets, referred to as the rest period or interpacket delay 406, is set between about 0.1 seconds and about 5 seconds, including all values and subranges in between. In other embodiments, the rest period 406 ranges from about 0.001 seconds to about 10 seconds, including all values and subranges in between, such as 1 second, 2 seconds, 3 seconds, 4 seconds, 5 seconds, 6 seconds, 7 seconds, 8 seconds, 9 seconds, 10 seconds, etc. In some embodiments, the rest period 406 is approximately 3-5 seconds. In particular, in some embodiments the signal is synced with the cardiac rhythm so that each packet is delivered synchronously within a designated period relative to the heartbeats, thus the rest periods coincide with the heartbeats. In other embodiments wherein cardiac synchronization is utilized, the rest period 406 may vary, as the rest period between the packets can be influenced by cardiac synchronization, as will be described in later sections.

F. Switch Time and Dead Time/Inter-Cycle Delay

A switch time is a delay or period of no energy that is delivered between the positive and negative peaks of a biphasic pulse. In some embodiments, the switch time ranges between about 0 to about 1 microsecond, including all values and subranges in between. In other embodiments, the switch time ranges between 1 and 20 microseconds, including all values and subranges in between. In other embodiments, the switch time ranges between about 2 to about 8 microsecond, including all values and subranges in between.

Delays may also be interjected between each cycle of the biphasic pulses, referred as "dead-time" or inter-cycle delays. Inter-cycle delays occur within a packet, but between cycles or biphasic pulses. This is in contrast to rest periods or inter-packet delays which occur between packets. In other embodiments, the inter-cycle delay 412 is in a range of 0.01 to 0.5 microseconds, 1 to 10 microseconds, 2 to 5 microseconds, 10 to 20 microseconds, 50 to 100 microseconds, 1000 microseconds, 1000 to 1500 microseconds or 1000 microseconds to 100 milliseconds, including all values and subranges in between. In some embodiments, the inter-cycle delay 412 is in the range of 0.2 to 0.3 microseconds. Inter-cycle delays may also be used to define a period between separate, monophasic, pulses within a packet.

Delays of this sort are typically introduced to a packet to reduce the effects of biphasic cancellation within the waveform. Biphasic cancellation is a term used to refer to the reduced induction of cellular modulation in response to biphasic waveforms versus monophasic waveforms, particularly when switch times and dead times are small, such as below 10 µs. In some embodiments, the influence of biphasic cancellation is reduced by introducing switch time delays and dead time. In some instances, the switch time and dead time are both increased together to strengthen the effect. In other instances, only switch time or only dead time are increased to induce this effect.

In some embodiments, the switch time duration is adjusted such that the degree of therapy effect relative to distant cell effects is optimized for the target of the therapy. In some embodiments, the switch time duration or dead time duration is minimized to decrease distant muscle cell contractions, with lesser local therapy effect. In other embodiments, the switch time duration is extended to increase the local therapy effect, with potential additional distant muscle cell contractions. In some embodiments, the switch time or dead time duration are extended to increase the local therapy effect, and the use of neuromuscular paralytics are employed to control the resulting increase in muscle contraction. In some embodiments, switch time duration is 10 ns to 2 μs, while in other embodiments, the switch time duration is 2 μs to 20 μs. In some instances, when cell modulation is targeted in a way where transmembrane potential manipulation is not the primary mechanism needed to evoke the targeted treatment effects, the switch time and dead time delays are minimized to less than 0.1p s or to 0 μs. This elimination of delays minimizes the peripheral, non-targeted treatment effects such as skeletal muscle contraction or cardiac muscle action potential and contraction.

Another benefit of utilizing switch time and the dead time delays to increase treatment effects for biphasic waveforms is a reduction in generator demands, whereby the introduction of pauses will enable stronger treatment effects without requiring asymmetric/unbalanced pulse waveforms. In this case, unbalanced waveforms are described as those that are monophasic, or have an unbalanced duration or voltage or combination in one polarity relative to the other. In some cases, unbalanced means that the integral of the positive portions of the waveform are not equal to the integral of the negative portions of the waveform. Generators capable of delivering unbalanced waveforms have a separate set of design considerations that are accounted for thereby increasing potential generator complexity.

G. Waveforms

In some embodiments, the waveform has symmetric pulses, such that the voltage and duration of pulse in one direction (i.e., positive or negative) is equal to the voltage and duration of pulse in the other direction. In some embodiments, the waveform has pulses of unbalanced voltages. An unbalanced waveform may result in a more pronounced treatment effect as the dominant positive or negative amplitude leads to a longer duration of same charge cell membrane charge potential. In some embodiments, imbalance includes pulses having pulse widths of unequal duration. In some embodiments, the biphasic waveform is unbalanced, such that the voltage in one direction is equal to the voltage in the other direction, but the duration of one direction (i.e., positive or negative) is greater than the duration of the other direction, so that the area under the curve of the positive portion of the waveform does not equal the area under the negative portion of the waveform. In some embodiments, an unbalanced waveform is achieved by delivering more than one pulse in one polarity before reversing to an unequal number of pulses in the opposite polarity.

H. Waveform Shapes

Rather than square waves, pulses are sinusoidal in shape in some embodiments. One benefit of a sinusoidal shape is that it is balanced or symmetrical, whereby each phase is equal in shape. Balancing may assist in reducing undesired muscle stimulation. It may be appreciated that in other embodiments the pulses have decay-shaped waveforms.

It may be appreciated that generating larger lesions (e.g. larger than approximately 1×1×1 $cm^3$) may involve different parameter values to obtain the same or similar lesion characteristics and/or immune response. In some embodiments, a lesion having a size of approximately 1.8×1.8×2.4 $cm^3$ may be achieved by a waveform that is produced from a combination of parameter values that includes the following: voltage=3300V, fundamental frequency=100 kHz, number of biphasic pulses (i.e., cycles) per packet=10 cycles, inter-cycle delay=1000 microseconds, number of packets=100 packets and inter-packet delay=3 seconds. In some embodiments, a lesion having a size of approximately 3×3×4 $cm^3$ may be achieved by a waveform that is produced from a combination of parameter values that includes the following: voltage=6000V, fundamental frequency=100 kHz, number of biphasic pulses (i.e., cycles) per packet=10 cycles, inter-cycle delay=1000 or 2000 microseconds, number of packets=100 packets and inter-packet delay=1, 3, 5 or 10 seconds.

It may be appreciated that in some embodiments, the waveform is generated as a function of electric current rather than voltage. For example, doses generated using 3000V or 3300V are delivered into environments of 150-300 ohm (generating 10-20 A for 3000V and 11-22 A for 3300V). In some embodiments, the electric current is 10 A, 15 A, 20 A, 25 A, 30 A, 35 A, 40 A, 45 A, 50 A, 55 A, 60 A, 65 A, 70 A, etc, and all ranges in between. It may be appreciated that in some instances, such as when using 100 kHz treatments that can be delivered with paralytic, 70 A may be the upper limit.

Energy delivery may be actuated by a variety of mechanisms, such as with the use of an actuator 132 on the instrument 102 or a foot switch operatively connected to the generator 104. Such actuation typically provides a single energy dose. The energy dose is defined by the number of packets delivered and the voltage of the packets. Each energy dose delivered to the target tissue maintains the temperature at or in the target tissue below a threshold for thermal ablation, particularly thermal ablation or denaturing of stromal proteins in the basement membrane or deeper submucosal extracellular protein matrices. In addition, the doses may be titrated or moderated over time so as to further reduce or eliminate thermal build up during the treatment procedure. Instead of inducing thermal damage, defined as protein coagulation at sites of danger to therapy, the energy dose provides energy at a level which induces treatment of the condition, such as cancer, without damaging sensitive tissues.

It may be appreciated that although the examples described herein are in relation to tumors such as in the treatment of cancer, the devices, systems and methods are not so limited. For example, signaling regulated by the PD-1/PD-L pathway is also associated with substantial inflammatory effects that can resemble those in autoimmune responses, chronic infection, and sepsis, consistent with the role of this pathway in balancing protective immunity and immunopathology, as well as in homeostasis and tolerance. Therefore, the devices, systems and methods may be used to target this pathway in autoimmune and inflammatory disorders, chronic infections, and sepsis. Other conditions and disorders that may be treated include ischemia-reperfusion injury (IRI), stroke, Alzheimer's disease (AD), and pain due to the immunoregulatory role of the PD-1/PD-L pathway in these disorders. Similarly, post-stroke inflammation may be treated due to the involvement of the PD-1/PD-L.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within 10% of the recited value. For example, in some instances, "about 100 [units]" can mean within ±10% of 100 (e.g., from 90 to 110). The terms "about" and "approximately" can be used interchangeably.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for treating tissue within a body of a patient comprising:

an instrument having at least one energy delivery electrode at a distal end of a shaft, wherein the at least one energy delivery electrode is configured to be positioned so as to direct pulsed electric field energy in a monopolar fashion to the tissue creating a lesion with the use of a dispersive return electrode configured to be positioned remote from the energy delivery electrode; and a generator in electrical communication with the at least one energy delivery electrode, the generator comprising a user interface, a processor, and a plurality of selectable energy delivery algorithms programmed in a memory, wherein the user interface is configured to receive a user selection corresponding to the selected energy delivery algorithm, wherein the processor is configured to execute the selected energy delivery algorithm to prescribe output instructions comprising waveform parameters for generating the pulsed electric field energy, and wherein the generator is configured to generate, according to the output instructions, a waveform delivered by the energy delivery electrode to create a plurality of zones within the lesion which elicits an increase in an adaptive immune response of the patient, wherein the waveform parameters are programmed in the memory to manipulate a tissue effect and a size of one or more zones of the plurality of zones, and wherein the waveform comprises biphasic pulse cycles at the waveform parameters comprising a voltage of 3,000 V to 5,000 V having a fundamental frequency of 100 kHz to 500 kHz, and a switch time of less than 0.1 microseconds for the pulsed electric field energy delivered by the energy delivery electrode.

2. The system of claim 1, wherein the plurality of zones has a bulls-eye arrangement.

3. The system of claim 1, wherein the plurality of zones includes at least a pulsed electric field zone and one or more of an immune response zone an inflammatory zone.

4. The system of claim 1, wherein the plurality of zones includes at least a pulsed electric field zone and a thermal zone.

5. The system of claim 4, wherein the waveform parameters of the plurality of selectable energy delivery algorithms include inter-cycle delays, wherein the inter-cycle delays are configured to control the size of the thermal zone.

6. The system of claim 5, wherein the inter-cycle delays are at least 10 microseconds.

7. The system of claim 5, wherein the inter-cycle delays are configured to inhibit or eliminate a cavitation zone.

8. The system of claim 4, wherein the biphasic pulse cycles are arranged in packets and wherein the waveform parameters of the plurality of selectable energy delivery algorithms include inter-packet delays, wherein the inter-packet delays are configured to control the size of the thermal zone.

9. The system of claim 8, wherein the inter-packet delays are 3-5 seconds.

10. The system of claim 1, wherein the waveform parameters are programmed in the memory so that the pulsed electric field energy delivered by the energy delivery electrode creates the lesion by a single dose within 5-6 minutes.

11. The system of claim 1, wherein the waveform parameters are programmed in the memory so that the pulsed electric field energy delivered by the energy delivery electrode causes the adaptive immune response comprising an increase in a ratio of CD8+/CD4+ T-cells.

12. The system of claim 1, wherein the waveform parameters are programmed in the memory so that the pulsed electric field energy delivered by the energy delivery electrode causes the adaptive immune response comprising an increase in PD-L1 expression.

13. The system of claim 1, wherein the waveform parameters are programmed in the memory so that the pulsed electric field energy delivered by the energy delivery electrode causes the adaptive immune response comprising an upregulation of lymphoid pathways.

14. The system of claim 1, wherein the waveform parameters are programmed in the memory so that the pulsed electric field energy delivered by the energy delivery electrode causes the adaptive immune response comprising a generation of tumor antigen release.

15. The system of claim 1, wherein the waveform parameters are programmed in the memory so that the pulsed electric field energy delivered by the energy delivery electrode causes the adaptive immune response comprising a downregulation of regulatory T-cells.

16. The system of claim 1, wherein the waveform parameters are programmed in the memory so that the pulsed electric field energy delivered by the energy delivery electrode causes the adaptive immune response comprising a generation or increase in generation of Tertiary Lymphoid Structures within the tissue.

17. The system of claim 1, wherein the plurality of selectable energy delivery algorithms are programmed in the memory to so that the pulsed electric field energy delivered by the energy delivery electrode creates a synergistic effect when the pulsed electric field energy is combined with an immune checkpoint inhibitor.

18. The system of claim 17, wherein the synergistic effect increases an abscopal effect.

19. The system of claim 17, wherein the immune checkpoint inhibitor comprises anti-PD1 therapy and wherein the synergistic effect increases PD-L1 expression.

20. The system of claim 1, wherein the waveform comprises packets of the biphasic pulse cycles.

21. The system of claim 20, wherein each packet has 40 biphasic pulse cycles.

22. The system of claim 20, wherein an inter-cycle delay of 1000 microseconds is disposed between each biphasic pulse cycle within a packet.

23. The system of claim 20, wherein the waveform comprises 100 packets in a single dose.

24. The system of claim 20, wherein an inter-packet delay of 3 seconds is disposed between each packet of the dose.

25. The system of claim 1, wherein the biphasic pulse cycles are arranged in packets wherein each packet has a 100 microsecond on time.

* * * * *